US009499606B2

(12) United States Patent
Shapiro

(10) Patent No.: US 9,499,606 B2
(45) Date of Patent: Nov. 22, 2016

(54) COMPOSITIONS OF, AND METHODS FOR, ALPHA-1 ANTI TRYPSIN FC FUSION MOLECULES

(71) Applicant: THE REGENTS OF THE UNIVERSITY OF COLORADO, A BODY CORPORATE, Boulder, CO (US)

(72) Inventor: Leland Shapiro, Denver, CO (US)

(73) Assignee: The Regents of the University of Colorado, a body corporate, Boulder, CO (US)

( * ) Notice: Subject to any disclaimer, the term of this patent is extended or adjusted under 35 U.S.C. 154(b) by 127 days.

(21) Appl. No.: 13/958,443

(22) Filed: Aug. 2, 2013

(65) Prior Publication Data

US 2014/0234310 A1   Aug. 21, 2014

Related U.S. Application Data

(60) Continuation of application No. 13/297,095, filed on Nov. 15, 2011, now Pat. No. 8,633,305, and a division of application No. 10/926,051, filed on Aug. 26, 2004, now Pat. No. 7,850,970, and a continuation of application No. 12/555,895, filed on Sep. 9, 2009, now abandoned.

(60) Provisional application No. 60/497,703, filed on Aug. 26, 2003.

(51) Int. Cl.
| | |
|---|---|
| *A61K 39/00* | (2006.01) |
| *A61K 45/00* | (2006.01) |
| *A61K 47/00* | (2006.01) |
| *A61K 39/42* | (2006.01) |
| *A61K 39/395* | (2006.01) |
| *A61K 39/38* | (2006.01) |
| *C07K 1/00* | (2006.01) |
| *C07K 14/00* | (2006.01) |
| *C07K 17/00* | (2006.01) |
| *C07K 14/81* | (2006.01) |
| *A61K 31/519* | (2006.01) |
| *A61K 45/06* | (2006.01) |
| *A61K 38/57* | (2006.01) |
| *C07K 14/47* | (2006.01) |
| *C07K 16/00* | (2006.01) |

(52) U.S. Cl.
CPC ......... *C07K 14/8125* (2013.01); *A61K 31/519* (2013.01); *A61K 38/57* (2013.01); *A61K 45/06* (2013.01); *C07K 14/473* (2013.01); *C07K 14/811* (2013.01); *C07K 16/00* (2013.01); *C07K 2319/00* (2013.01); *C07K 2319/21* (2013.01); *C07K 2319/23* (2013.01); *C07K 2319/30* (2013.01); *C07K 2319/43* (2013.01); *C07K 2319/50* (2013.01)

(58) Field of Classification Search
CPC .......... C07K 2317/52; C07K 2317/24; A61K 2039/505; A61K 38/00; A61K 39/395
See application file for complete search history.

(56) References Cited

U.S. PATENT DOCUMENTS

| | | | |
|---|---|---|---|
| 4,021,472 A | 5/1977 | Fujii et al. | |
| 4,224,342 A | 9/1980 | Fujii et al. | |
| 4,283,418 A | 8/1981 | Fujii et al. | |
| 4,522,811 A | 6/1985 | Eppstein et al. | |
| 4,629,567 A | 12/1986 | Bollen et al. | |
| 4,711,848 A | 12/1987 | Insley et al. | |
| 4,829,052 A | 5/1989 | Glover et al. | |
| 4,829,054 A | 5/1989 | Emerson, Jr. et al. | |
| 4,857,538 A | 8/1989 | Kashman et al. | |
| 4,963,654 A | 10/1990 | Katunuma | |
| 5,008,242 A | 4/1991 | Lezdey et al. | |
| 5,093,316 A | 3/1992 | Lezdey et al. | |
| 5,116,964 A | 5/1992 | Capon et al. | |
| 5,134,119 A | 7/1992 | Lezdey et al. | |
| 5,157,019 A | 10/1992 | Glover et al. | |
| 5,175,253 A | 12/1992 | Fallon et al. | |
| 5,216,022 A | 6/1993 | Oleksyszyn et al. | |
| 5,346,886 A | 9/1994 | Lezdey et al. | |
| 5,420,110 A | 5/1995 | Miller | |

(Continued)

FOREIGN PATENT DOCUMENTS

| | | |
|---|---|---|
| EP | 511188 | 6/1997 |
| WO | 9318794 | 9/1993 |

(Continued)

OTHER PUBLICATIONS

Langner KD, Niedrig M, Fultz P, Anderson D, Reiner G, Repke H, Gelderblom H, Seed B, Hilfenhaus J, Zettlmeissl G. Antiviral effects of different CD4-immunoglobulin constructs against HIV-1 and SIV: immunological characterization, pharmacokinetic data and in vivo experiments. Arch Virol. 1993;130(1-2):157-70.

(Continued)

*Primary Examiner* — Gary Nickol
*Assistant Examiner* — Lakia Tongue
(74) *Attorney, Agent, or Firm* — Faegre Baker Daniels LLP

(57) ABSTRACT

A novel method of treating and preventing bacterial diseases is provided. In particular, the present invention relates to compositions and methods for inhibition of Gram negative, Gram positive and acid fast bacilli in general and tuberculosis (TB), *mycobacterium avium* complex (MAC), and anthrax in particular. Thus, the invention relates to modulation of cellular activities, including macrophage activity, and the like. More particularly, the present invention relates to the inhibitory compounds comprising naturally occurring and man-made inhibitors of serine protease.

9 Claims, 10 Drawing Sheets

(56) References Cited

U.S. PATENT DOCUMENTS

| | | | |
|---|---|---|---|
| 5,455,165 | A | 10/1995 | Capon et al. |
| 5,514,582 | A | 5/1996 | Capon et al. |
| 5,514,653 | A | 5/1996 | Perlmutter |
| 5,604,201 | A | 2/1997 | Thomas et al. |
| 5,610,285 | A | 3/1997 | Lebing et al. |
| 5,612,194 | A | 3/1997 | Rubin et al. |
| 5,616,693 | A | 4/1997 | Hwang et al. |
| 5,710,026 | A | 1/1998 | Sprecher |
| 5,714,140 | A | 2/1998 | Strassmann |
| 5,714,147 | A | 2/1998 | Capon et al. |
| 5,734,014 | A | 3/1998 | Ishima et al. |
| 5,780,440 | A | 7/1998 | Lezdey et al. |
| 5,861,380 | A | 1/1999 | Gyorkos et al. |
| 5,869,455 | A | 2/1999 | Gyorkos et al. |
| 5,874,424 | A | 2/1999 | Batchelor et al. |
| 5,905,023 | A | 5/1999 | Sager et al. |
| 5,985,279 | A | 11/1999 | Waldmann et al. |
| 6,022,855 | A | 2/2000 | Thomas et al. |
| 6,124,257 | A | 9/2000 | Lezdey |
| 6,136,834 | A | 10/2000 | Ohmoto et al. |
| 6,174,859 | B1 | 1/2001 | Lezdey et al. |
| 6,287,817 | B1 | 9/2001 | Davis et al. |
| 6,489,308 | B1 | 12/2002 | Shapiro |
| 6,849,605 | B1 | 2/2005 | Shapiro |
| 6,924,267 | B2 | 8/2005 | Daemen et al. |
| 7,034,033 | B2 | 4/2006 | Boyce et al. |
| 2002/0081607 | A1 | 6/2002 | Ruben et al. |
| 2003/0040097 | A1* | 2/2003 | Ruben et al. ............... 435/226 |
| 2003/0069395 | A1 | 4/2003 | Sato et al. |
| 2003/0073217 | A1 | 4/2003 | Barr et al. |
| 2003/0190311 | A1 | 10/2003 | Dall'Acqua et al. |
| 2004/0220239 | A1 | 11/2004 | Shapiro |
| 2004/0220242 | A1 | 11/2004 | Shapiro |
| 2004/0254349 | A1 | 12/2004 | James et al. |
| 2008/0085854 | A1 | 4/2008 | Barr et al. |
| 2009/0298747 | A1 | 12/2009 | Shapiro |
| 2010/0111940 | A1 | 5/2010 | Flier et al. |

FOREIGN PATENT DOCUMENTS

| | | |
|---|---|---|
| WO | 9528422 | 10/1995 |
| WO | 9534538 | 12/1995 |
| WO | 9721690 | 6/1997 |
| WO | 9733996 | 9/1997 |
| WO | 9823645 | 6/1998 |
| WO | 9824806 | 6/1998 |
| WO | 0044390 | 8/2000 |
| WO | 0051623 | 9/2000 |
| WO | 0051624 | 9/2000 |
| WO | 0051625 | 9/2000 |
| WO | 0052034 | 9/2000 |
| WO | 0103737 | 1/2001 |
| WO | 02053092 | 7/2002 |
| WO | 02060919 | 8/2002 |
| WO | 02068455 | 9/2002 |
| WO | 02949864 | 11/2002 |
| WO | 02102318 | 12/2002 |
| WO | 2003021273 A2 | 3/2003 |
| WO | 03059935 | 7/2003 |
| WO | 2005019434 A2 | 3/2005 |
| WO | 2005046454 A2 | 5/2005 |
| WO | 2005112970 A2 | 12/2005 |
| WO | 2007079312 A2 | 7/2007 |

OTHER PUBLICATIONS

Mohler KM, Torrance DS, Smith CA, Goodwin RG, Stremler KE, Fung VP, Madani H, Widmer MB. Soluble tumor necrosis factor (TNF) receptors are effective therapeutic agents in lethal endotoxemia and function simultaneously as both TNF carriers and TNF antagonists. J Immunol. 1993; 151(3):1548-61.

Novak EJ, Blosch CM, Perkins JD, Davis CL, Barr D, McVicar JP, Griffin RS, Farrand AL, Wener M, Marsh CL. Recombinant human tumor necrosis factor receptor Fc fusion protein therapy in kidney transplant recipients undergoing OKT3 induction therapy. Transplantation. 1998; 66(12):1732-5.

Jones TD, Hanlon M, Smith BJ, Heise CT, Nayee PD, Sanders DA, Hamilton A, Sweet C, Unitt E, Alexander G, Lo KM, Gillies SD, Carr FJ, Baker MP. The development of a modified human IFN-alpha2b linked to the Fc portion of human IgG1 as a novel potential therapeutic for the treatment of hepatitis C virus infection. J Interferon Cytokine Res. 2004; 24(9):560-72.

Alex Bollen, Albert Herzog, Alfredo Cravador, Pascal Hérion, Paul Chuchana, Ariane Vander Straten, Rosette Loriau, Paul Jacobs, and Ary Van Elsen. Cloning and Expression in *Escherichia coli* of Full-Length Complementary DNA Coding for Human cv,-Antitrypsin DNA. Dec. 1983, 2(4): 255-264. doi:10.1089/dna.1983. 2.255.

Anderson et., "Inhibition of HIV-1 gp160-dependent membrane fusion by a furin-directed alpha 1-antitrypsin variant," J. Biol. Chem 1993, 268(33):24887-91.

Dermer, "Another Anniversary for the War on Cancer," Bio/Technology 1994, 12:320.

Dong, V.M., et al, Ped/Transplant, 161:118-189, 1999.

Freshney "Culture of Animal Cells, A Manual of Basic Technique," A.R. Liss, Inc., NY, 1983, p. 4.

Gaur et al., "Effect of nasal immunization with protective antigen of *Bacillus anthracis* on protective immune response against anthrax toxin," Vaccine 2002, 20:2836-39.

Goodnow, C., Lancet, 357: (9274):2115-2121, Jun. 30, 2001.

Greenspan et al., "Defining epitopes: It's not as easy as it seems," Nature Biotechnology 1999, 17(1):936-37.

Ihse, I., et al. 1876 "Oral trypsin-inhibitor-induced improvement of the exocrine and endocrine pancreatic functions in alloxan diabetic rats," Scandinavian Journal of Gastroenterology, vol. 11, pp. 363-368.

Ikeda, T., et al., 1996, "An inhibition of urinary albumin excretion by protease inhibitor in streptozotocin-diabetic rats," Nephron, vol. 74, No. 4, pp. 709-712.

Katsura, M. et al., "Effect of long-term oral administration of trypsin inhibitor on pancreatic exocrine dysfunction in non-insulin dependent diabetes mellitus (NIDDM)", Journal of Pancreas, vol. 7, No. 2, pp. 1-8, 1992.

Katsura, M., et al., Journal of Pancreas, English Translation, 23 pages, 1992.

Leppla et al., "Development of an improved vaccine for anthrax," J Clin Invest 2002, 109:141-44.

Lieberman, "Augmentation therapy reduces frequency of lung infections in antitrypsin deficiency: A new hypothesis with supporting data." Chest 2000, 118(5):1480-1485.

Lomas et al., "Commercial plasma alpha 1-antitrypsin (Prolastin) contains a conformationally inactive, latent component," Eur Respir J. 1997, 10(3):672-675.

Lomas et al., "Preparation and Characterization of Latent alpha-1 antitrypsin," J Biol Chem 1995, 270:5282-5288.

Musson, J. et al., "Differential Processing of CD4 T-cell epitopes from the protective antigen of *Bacillus anthracis*, " J Biol Chem 2003, 278(52): 52425-52431.

Panasiuk, A.V., et al., Disseminated pulmonary tuberculosis, diabetes mellitus and amyloidosis in a patient with hereditary alpha 1-antitrypsin deficiency, Probl Tuberk, 1988, No. 1, pp. 72-74.

Rothe et al (J. Immunol, 1999, 163: 1230-1236).

Shapiro et al., "Alpha-1-antitrypsin inhibits human immunodeficiency virus type 1," FASEB J 2001, 15(1):115-122.

Simpson et al., "Adenoviral augmentation of elafin protects the lung against acute injury mediated by activated neutrophils and bacterial infection," J Immunol , 2001, 167:1778-86.

Song et al (Gene Therapy 2004, 11: 181-186).

Yang et al (J. Am. Soc. Nephrol. 2003, 14:214-225).

Bollen A. Herzog A, Cravador, A, Herion P., Chuchana P., Vander Straten A, Loriau R, Jacobs P, van Elsen, A., "Cloning and expression *Escherichia coli* of full-lengtth complementary DNA coding for human alpha 1-antitrypsin" DNA Dec. 1983, 2(4):255-264. doi:10.1089/dna. 1983.2.255.

(56) References Cited

OTHER PUBLICATIONS

Baecher, Allan et al. Human regulatory T cells and their role in autoimmune disease, Immunology Reviews, vol. 212, (2006), pp. 203-216.
Bell, J.J. et al. In Trans T Cell Tolerance Diminishes Autoantibody Responses and Exacerbates Experimental Allergic Encephalomyelitis, The Journal of Immunology, vol. 180 (2008), pp. 1508-1516.
Chaiet, Pamela Pam Chaiet Reveals the Latest Tech in the Struggle to Cure Diabetes, The Potomac, Issue 10, (Dec. 14, 2010).
Chan, et al., Alpha-1-antitrypsin (AAT) anomalies are associated with lung disease due to rapidly growing mycobacteria and AAT inhibits Mycobacterium abscessus infection of macrophages, Scandinavian Journal of Infectious Diseases, vol. 39 (2007), pp. 690-696.
eMedicineHealth, Anthrax, Apr. 25, 2007, found at http://www.emedicinehealth.com/script/main/art.asp?articlekey=59372&pf=3&page=7.
International Search Report and Written Opinion, Application No. PCT/US04/27711, Jul. 19, 2005.
International Search Report and Written Opinion, Application No. PCT/US06/22436.
Date mailed Jul. 12, 2007, International Search Report and Written Opinion, Application No. PCT/US06/61577, Dec. 7, 2007.
International Search Report and Written Opinion, Application No. PCT/US08/60848, Dec. 22, 2008.
Kraus, T.A. et al., Oral tolerance and inflammatory bowel disease, Current Opinion in Gastroenterology, vol. 21 (2005), pp. 692-696.
Lewis, Eli C et al., a1-Antitrypsin monotherapy prolongs islet allograft survival in mice, PNAS, vol. 102, No. 34 (Aug. 23, 2005), pp. 12153-12158.
Market Letter, Sep. 13, 2009, 2 Pages.
Nakamura, N. et al., Effect of trypsin inhibitor on blood sugar, insulin, and glucagon levfels in normal and streptozotocin rats, Journal of the Kyoto Prefecture University of Medicine, vol. 89, No. 6 (1980) pp. 465-470.
O'Riordan et al. a1-Antitrypsin Deficiency-Associated Panniculitis, Departments of Medicine, Pathology, and Transplantation Surgery, Northwestern University Medical School, vol. 63, No. 3, (1996) pp. 1052-1055.
Palomino, Juan Carlos, New Anti-Tuberculosis Drugs: Strategies, Sources and New Molecules, Current Medicinal Chemistry, vol. 16 (2009) pp. 1898-1904.
Pozzilli, P. et al., No effect of oral insulin on residual beta-cell function in recent-onset Type 1 diabetes (the IMDIABVII), Diabetologia, vol. 43, (2000) pp. 1000-1004.
Schroeder, Rebecca A. et al., Tolerance and the "Holy Grail" of Transplantation, Journal of Surgical Research, vol. 111, (2003) pp. 109-119.
Shimoda, Izumi et al., Physiological Characteristics of Spontaneously Developed Diabetes in Male WBGN/Kob Rat and Prevention of Development of Diabetes by Chronic Oral Administration of Synthetic Trypsin Inhibitor (FOY-305), Pancreas, vol. 8, No. 2, (1993) pp. 196-203.
Skyler, Jay S. et al., Use of Inhaled Insulin in a Basal/Bolus Insulin Regimen in Type 1 Diabetic Subjects, Diabetes Care vol. 28, (2005) pp. 1630-1635.
Strom, Terry B., Saving islets from allograft rejection, PNAS, vol. 102, No. 36 (2005) pp. 12651-12652.
Supplementary European Search Report, Application No. EP/04801916.0, Aug. 17, 2009.
Schwaiblmair M, Vogelmeier C. Alpha 1-antitrypsin. Hope on the horizon for emphysema sufferers? Drugs Aging. 1998; 12(6):429-40.
Karnaukhova E, Ophir Y, Golding B. Recombinant human alpha-1 proteinase inhibitor: towards therapeutic use. Amino Acids. 2006; 30(4):317-32.
Powell LM, Pain RH.Effects of glycosylation on the folding and stability of human, recombinant and cleaved alpha 1-antitrypsin. J Mol Biol. 1992 ;224(1):241-52.
Zamora NP, Pla RV, Del Rio PG, Margaleff RJ, Frias FR, Ronsano JB. Intravenous human plasma-derived augmentation therapy in alpha 1-antitrypsin deficiency: from pharmacokinetic analysis to individualizing therapy. Ann Pharmacother. 2008; 42(5):640-6.
Mast AE, Salvesen G, Schnebli HP, Pizzo SV. Evaluation of the rapid plasma elimination of recombinant alpha 1-proteinase inhibitor: synthesis of polyethylene glycol conjugates with improved therapeutic potential. J Lab Clin Med. 1990; 116(1):58-65.
Zettlmeissl G, Gregersen JP, Duport JM, Mehdi S, Reiner G, Seed B. Expression and characterization of human CD4: immunoglobulin fusion proteins. DNA Cell Biol. 1990; 9(5):347-53.
Kurachi et al., "Cloning and sequence of cDNA coding for a1-antitrypsin," Proc. Natl. Acad. Sci. USA, vol. 78 (11):6826-6830 (1981).
Eckman et al., "In Vitro Transport of Active a1-Antitrypsin to the Apical Surface of Epithelia by Targeting the Polymeric Immunoglobulin Receptor," Am. J. Respir. Cell Mol. Bioi., vol. 21:246-52 (1999).
Rutishauser et al., "Amino Acid Sequence of the Fe Region of a Human yG Immunoglobulin," Proc. Natl. Acad. Sci. USA, vol. 61(4):1414-1421 (1968).
Request for Ex Parte Reexamination filed Sep. 19, 2014 in connection with U.S. Pat. No. 8,633,305, 79 pages.
Office Action in Ex Parte Reexamination mailed Feb. 6, 2015 in connection with U.S. Pat. No. 8,633,305, 15 pages.
Extended European search report and search opinion dated Jul. 16, 2015 for EP 12804863.4.
Final Office Action issued in U.S. Appl. No. 14/084,132 mailed Mar. 6, 2015, 11 pages.
Libert et al. Alpha1-Antitrypsin Inhibits the Lethal Response to TNF in Mice; The Journal of Immunology, 1996, 157: 5123-5129.
Vaerman et al. Complexes of albumin and alpha1-antitrypsin with Fc-fragment of IgA monomer are disulfide-bound to penultimate C-terminal cysteine in the Calpha3-domain. Immunology Letters, 1987, 15, pp. 67-72.

\* cited by examiner

Transport of lethal factor and/or edema factor into the cell

FIG. 4 F

COMPOSITIONS OF, AND METHODS FOR, ALPHA-1 ANTI TRYPSIN FC FUSION MOLECULES

PRIORITY

This is a continuation application of a continuation application, U.S. patent application Ser. No. 13,297,095 filed Nov. 15, 2011 that claims priority to U.S. patent application Ser. No. 12/555,895, filed Sep. 9, 2009, now abandoned, which claims priority to U.S. patent application Ser. No. 10/926,051, filed Aug. 26, 2004 now U.S. Pat. No. 7,850,970, issued on Dec. 14, 2010, which claims priority to U.S. Provisional Application No. 60/497,703, filed Aug. 26, 2003. These applications are incorporated herein by reference in their entirety for all purposes.

FIELD OF THE INVENTION

The present invention relates to compositions and methods for inhibition of bacterial infections comprising Gram negative, Gram positive, and acid fast bacilli in general and *mycobacterium tuberculosis* (TB), *mycobacterium avium* complex (MAC), and anthrax in particular, as well as to therapeutic treatment of diseases or disorders that involve infection of macrophages. Thus, the invention relates to modulation of cellular activities, including macrophage activity, inhibition of toxin, and the like. More particularly, the present invention also relates to inhibitory compounds comprising naturally occurring and man-made serine protease inhibitors and antagonists.

BACKGROUND OF THE INVENTION

Serine Proteases

Serine proteases serve an important role in human physiology by mediating the activation of vital functions. In addition to their normal physiological function, serine proteases have been implicated in a number of pathological conditions in humans. Serine proteases are characterized by a catalytic triad consisting of aspartic acid, histidine and serine at the active site.

The naturally occurring serine protease inhibitors are usually, but not always, polypeptides and proteins which have been classified into families primarily on the basis of the disulfide bonding pattern and the sequence homology of the reactive site. Serine protease inhibitors, including the group known as serpins, have been found in microbes, in the tissues and fluids of plants, animals, insects and other organisms. Protease inhibitor activities were first discovered in human plasma by Fermi and Pemossi in 1894. At least nine separate, well-characterized proteins are now identified, which share the ability to inhibit the activity of various proteases. Several of the inhibitors have been grouped together, namely α1-antitrypsin-proteinase inhibitor, antithrombin III, antichymotrypsin, C1-inhibitor, and α2-antiplasmin, which are directed against various serine proteases, i.e., leukocyte elastase, thrombin, cathepsin G, chymotrypsin, plasminogen activators, and plasmin. These inhibitors are members of the α1-antitrypsin-proteinase inhibitor class. The protein α2-macroglobulin inhibits members of all four catalytic classes: serine, cysteine, aspartic, and metalloproteases. However, other types of protease inhibitors are class specific. For example, the α1-antitrypsin-proteinase inhibitor (also known as (α1-antitrypsin or AAT) and inter-α-trypsin inhibitor inhibit only serine proteases, α1-cysteine protease inhibitor inhibits cysteine proteases, and α1-anticollagenase inhibits collagenolytic enzymes of the metalloenzyme class.

Human neutrophil elastase (NE) is a proteolytic enzyme secreted by polymorphonuclear leukocytes in response to a variety of inflammatory stimuli. The degradative capacity of NE, under normal circumstances, is modulated by relatively high plasma concentrations of α1-antitrypsin. However, stimulated neutrophils produce a burst of active oxygen metabolites, some of which (hypochlorous acid for example) are capable of oxidizing a critical methionine residue in α1-antitrypsin. Oxidized α1-antitrypsin has been shown to have a limited potency as a NE inhibitor and it has been proposed that alteration of this protease/antiprotease balance permits NE to perform its degradative functions in localized and controlled environments.

α1-antitrypsin is a glycoprotein of MW 51,000 with 417 amino acids and 3 oligosaccharide side chains. Human α1-antitrypsin was named anti-trypsin because of its initially discovered ability to inactivate pancreatic trypsin. Human α1-antitrypsin is a single polypeptide chain with no internal disulfide bonds and only a single cysteine residue normally intermolecularly disulfide-linked to either cysteine or glutathione. The reactive site of α1-antitrypsin contains a methionine residue, which is labile to oxidation upon exposure to tobacco smoke or other oxidizing pollutants. Such oxidation reduces the biological activity of α1-antitrypsin; therefore substitution of another amino acid at that position, i.e. alanine, valine, glycine, phenylalanine, arginine or lysine, produces a form of α1-antitrypsin which is more stable. α1-antitrypsin can be represented by the following formula, SEQ ID NO. 63:

```
1          01         01         01         01         0
MPSSVSWGIL LAGLCCLVPV SLAEDPQGDA AQKTDTSHHD QDHPTFNKIT

PNLAEFAFSL YRQLAHQSNS TNIFFSPVSI ATAFANLSLG TKADTHDEIL 100

EGLNFNLTEI PEAQIHEGFQ ELLRTLNQPD SQLQLTTGNG LFLSEGLKLV

DKFLEDVKKL YHSEAFTVNF GDHEEAKKQI NDYVEKGTQG KIVDLVKELD 200

RDTVFALVNY IFFKGKWERP FEVKDTEDED HVDQVTTVK  VPMMKRLGMF

NIQHCKKLSS WVLLMKYLGN ATAIFFLPDE GKLQHLENEL THDIITKFLE 300

NEDRRSASLH LPKLSITGTY DLKSVLGQLG ITKVFSNGAD LSGVTEEAPL

KLSKAVHKAV LTIDEKGTEA AGAMFLEAIP MSIPPEVKFN KPFVFLMIEQ 400

NTKSPLFMGK VVNPTQK                                    417
```

Ciliberto, et al. in Cell 1985, 41, 531-540. The critical amino acid sequence near the carboxyterminal end of α1-antitrypsin is shown in bold and underlined and is pertinent to this invention (details of the sequence can be found for example in U.S. Pat. No. 5,470,970 as incorporated by reference).

The normal plasma concentration of ATT ranges from 1.3 to 3.5 mg/ml although it can behave as an acute phase reactant and increases 3-4-fold during host response to inflammation and/or tissue injury such as with pregnancy, acute infection, and tumors. It easily diffuses into tissue spaces and forms a 1:1 complex with a target protease, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen. Humans with circulating levels of α1-antitrypsin less than 15% of normal are susceptible to the development of lung disease, e.g., familial emphysema, at an early age. Familial emphysema is associated with low ratios of α1-antitrypsin to serine proteases, particularly elastase. Therefore, it appears that this inhibitor represents an important part of the defense mechanism against attack by serine proteases.

α1-antitrypsin is one of few naturally occurring mammalian serine protease inhibitors currently approved for the clinical therapy of protease imbalance. Therapeutic α1-antitrypsin has been commercially available since the mid 80s and is prepared by various purification methods (see for example Bollen et al., U.S. Pat. No. 4,629,567; Thompson et al., U.S. Pat. Nos. 4,760,130; 5,616,693; WO 98/56821). Prolastin is a trademark for a purified variant of α1-antitrypsin and is currently sold by Bayer Company (U.S. Pat. No. 5,610,285 Lebing et al., Mar. 11, 1997). Recombinant unmodified and mutant variants of α1-antitrypsin produced by genetic engineering methods are also known (U.S. Pat. No. 4,711,848); methods of use are also known, e.g., (α1-antitrypsin gene therapy/delivery (U.S. Pat. No. 5,399,346 to French Anderson et al.).

The two known cellular mechanisms of action of serine proteases are by direct degradative effects and by activation of G-protein-coupled proteinase-activated receptors (PARs). The PAR is activated by the binding of the protease followed by hydrolysis of specific peptide bonds, with the result that the new N-terminal sequences stimulate the receptor. The consequences of PAR activation depend on the PAR type that is stimulated and on the cell or tissue affected and may include activation of phospholipase C.beta., activation of protein kinase C and inhibition of adenylate kinase (Dery, O. and Bunnett, N. W. Biochem Soc Trans 1999, 27,246-254; Altieri, D. C. J. Leukoc Biol 1995, 58, 120-127; Dery, O. et al. Am J. Physiol 1998, 274, C1429-C1452).

TB and MAC

*Mycobacterium* is a genus of bacteria which are aerobic, mostly slow growing, slightly curved or straight rods, sometimes branching and filamentous, and distinguished by acid-fast staining. Typically, mycobacteria are gram-positive obligate aerobes. The genus *mycobacterium* includes the highly pathogenic organisms that cause tuberculosis (*M. tuberculosis* and sometimes *M. bovis*) and leprosy (*M. leprae*). There are, however, many other species of *mycobacterium* such as *M. avium-intracellulare, M. chelonei* (also known as borstelense and abscessus), *M. africanum, M. marinium* (also known as balnei and platypoecilus), *M. buruli* (also known as ulcerans), *M. fortuitum* (also known as giae, minetti, and ranae), *M. haemophilum, M. intracellulare, M. kansasii* (also known as luciflavum), *M. littorale* (also known as xenopi), *M. malmoense, M. marianum* (also known as scrofulaceum and paraffinicum), *M. simiae, M. szulgai,* and *M. ulcerans.*

Mycobacteria which are pathogenic for animals but not believed to be pathogenic for humans include the following: *M. avium-intracellulare* (also known as brunense), *M. flavascens, M. lepraemurium, M. microti,* and *M. paratuberculosis* (which is the causative agent for Johne's Disease, and perhaps Crohn's disease). The following species of the genus *mycobacterium* are believed to be non-pathogenic: *M. gordonae* (also known as aquae), *M. gastri, M. phlei* (also known as moelleri and as timothy *bacillus*), *M. nonchromogenicum, M. smegmatis, M. terrae, M. triviale,* and *M. vaccae.*

Additionally, certain mycobacteria other than *M. tuberculosis* and *M. bovis* are alternatively known as non-tuberculosis mycobacteria. They are divided into four groups, also known as Runyon groups, based on pigmentation and growth rate. Each group includes several species. Group I refers to slow-growing photochromogens; Group II refers to slow-growing scotochromogens; Group III refers to slow-growing nonphotochromogens; and Group IV refers to rapidly-growing mycobacteria. The non-tuberculosis mycobacteria are also called atypical or anonymous mycobacteria.

Tuberculosis is an acute or chronic infectious disease caused by infection with *M. tuberculosis*. Tuberculosis is a major disease in developing countries, as well as an increasing problem in developed areas of the world, with approximately 8 million new cases and 3 million deaths each year (See Styblo et al., Bull. Int. Union Tuberc. 56:118-125 (1981). Although the infection may be asymptomatic for a considerable period of time, the disease is most commonly manifested as an acute inflammation of the lungs, resulting in fever and a nonproductive cough. If left untreated, serious complications and death typically result.

Although it is known that tuberculosis can generally be controlled using extended antibiotic therapy, such treatment is not sufficient to prevent the spread of the disease. Infected individuals may be asymptomatic, but contagious, for some time. In addition, although compliance with the specific treatment regimen is critical, patient behavior is often difficult to monitor. Treatment regimens often require six to twelve months of uniterrurpted therapy. As a result, some patients do not complete the course of treatment, thus leading to ineffective treatment and development of antibiotic resistance. Effective vaccination and accurate, early diagnosis of the disease are needed in order to inhibit the spread of tuberculosis. Vaccination with live bacteria remains the most efficient method for inducing protective immunity. The most common *Mycobacterium* employed in the live vaccine is *Bacillus* Calmette-Guerin (BCG), an avirulent strain of *Mycobacterium bovis*. Some countries, such as the United States, however, do not vaccinate the general public because of concerns regarding the safety and efficacy of BCG.

*M. tuberculosis* is an intracellular pathogen that infects macrophages and is able to survive within the harsh environment of the phagolysosome in macrophages. Most inhaled bacilli are destroyed by activated alveolar macrophages. However, the surviving bacilli multiply in macrophages and are released upon cell death, which signals the infiltration of lymphocytes, monocytes and macrophages to the site. Antigenic stimulation of T cells requires presentation by MHC molecules. Lysis of the bacilli-laden macrophages is mediated by the delayed-type hypersensitivity (DTH) cell-mediated immune response and results in the development of a solid caseous tubercle surrounding the area of infected cells. Tuberculosis bacilli possess many potential T-cell antigens and several have now been identified [Andersen 1994, Dan. Med. Bull. 41, 205]. Some of these antigens are secreted by the bacteria. Continued DTH liquefies the tubercle, thereby releasing entrapped tuberculosis bacilli. The large dose of extracellular tuberculosis bacilli triggers further DTH, causing damage to the bronchi and dissemination by lymphatic, hematogenous and bronchial routes, and eventually allowing infectious bacilli to be spread by respiration.

Cell-mediated immunity to tuberculosis involves several types of immune effector cells. Activation of macrophages by cytokines, such as interferon-.gamma., represents an effective means of minimizing macrophage-based intracellular mycobacterial multiplication. However, this does not lead to complete eradication of the bacilli. Acquisition of protection against tuberculosis additionally requires T lymphocytes. Among these, T cells of both the CD8+ and CD4+ lineage appear to be particularly important [Orme et al, 1993, J. Infect. Dis. 167, 1481]. These T-cells secrete interferon-.gamma. in response to mycobacteria, indicative of a T.sub.h 1 immune response, and possess cytotoxic activity to mycobacteria-pulsed target cells. In recent studies using .beta.-2 microglobulin- and CD8-deficient mice, cytotoxic T lymphocyte (CTL) responses have been shown to be critical in providing protection against *M. tuberculosis* [Flynn et al, 1992, Proc. Natl. Acad. Sci. USA 89, 12013; Flynn et al, 1993, J. Exp. Med. 178, 2249; Cooper et al, 1993, J. Exp. Med. 178, 2243]. In contrast, B lymphocytes do not appear to be involved, and passive transfer of anti-mycobacterial antibodies does not provide any protective immunity. Thus, an effective vaccine regimen against tuberculosis must trigger cell-mediated immune responses.

Although commonly thought of only as a pulmonary infection, TB is well known to afflict many parts of the body. In addition to pulmonary TB, examples of other foci of tubercular infection include miliary TB (generalized hematogenous or lymphohematogenous TB), central nervous system TB, pleural TB, TB pericarditis, genitourinary TB, TB of the gastrointestinal tract, TB peritonitis, TB of the adrenals, TB of the liver, TB of the bones and joints (for example, TB spondylitis or Pott's Disease), TB lymphadenitis, and TB of the mouth, middle ear, larynx, and bronchial tree.

Conventional therapy for TB includes treatment with regimens containing pyrazinamide, isoniazid, ethambutol, streptomycin, rifampin, rifabutin, clarithromycin, ciprofloxacin, clofazamine, azithromycin, ethionamide, amikacin and resorcinomycin A. To treat latent (inactive) TB infection, isoniazid may be used alone. However, the usual initial treatment for pulmonary tuberculosis includes isoniazid in combination with at least one other drug, such as ethambutol, streptomycin, rifampin or ethionamide. Retreatment of pulmonary tuberculosis typically involves drug combinations including rifampin and other drugs as noted above. Development of resistance of the causative agent to anti-TB drugs, especially isoniazid, is well known. Extrapulmonary tuberculosis is also usually treated with a combination including rifampin and at least one of the other three drugs mentioned.

*Mycobacterium Avium* Complex (MAC)

*M. avium* and *M. intracellulare* are members of the *Mycobacterium avium* complex (MAC). *M. paratuberculosis* is a subspecies of *M. avium* and is also generally included in the MAC. These species have become increasingly important in recent years because of the high prevalence of disseminated MAC infection in AIDS patients. The *Mycobacterium avium* complex is comprised of 28 serovars which are distinguishable on the basis of their biochemical and seroagglutination characteristics (see review by Inderlied, et al. 1993. Clin. Microbial. Rev. 6, 266-310). Depending on the method of classification, 10-12 of the 28 serovars are classified as belonging to the species *Mycobacterium avium*, and 10-12 belong to the species *Mycobacterium intracellulare*. Six of the MAC serovars have not yet been definitively classified. MAC infections currently account for approximately 50% of the pathogenic isolates identified by mycobacteriology labs and are most common among AIDS and other immuno-compromised patients. Early diagnosis and treatment of MAC infections can improve and prolong the lives of infected individuals.

Anthrax and Anthrax Toxin

Anthrax toxin, produced by the gram positive rod-shaped aerobic, spore-forming bacterium *Bacillus anthracis*, is the toxic virulence factor secreted by this organism. *B. anthraxis* is often considered for use as a biological weapon due to the potency of the secreted exotoxin, and to the capacity of the bacterium to form dormant spores which resist harsh environmental conditions. Sporulation enables ready transport and distribution of large quantities of toxin-producing bacteria. The toxin is actually a composite consisting of 3 separate secreted proteins from the bacterium. The 3 proteins are protective antigen (PA), lethal factor (LF), and edema factor (EF). While LF and EF directly damage cells and cause disease, the PA is the focus of this disclosure. PA is crucial to the virulence of anthrax toxin, since the PA molecule is designed to import both LF and EF inside the membranes of cells. In the absence of PA-induced intracellular transport, anthrax toxin is unable to effect tissue destruction, since LF and EF only function from within the cell. The importance of PA in the function of anthrax toxin is underscored by the effective use of PA as the immunogen in anthrax vaccine. By generating an immune response against PA, the vaccine confers protection against full (3 component) anthrax toxin.

A closer examination of the interaction between PA and the host cells attacked by anthrax toxin is instructive. PA is first secreted as an 83 kDa monomeric polypeptide by *B. anthracis* in a large and functionally inactive form. This inactive PA binds to a mammalian receptor on the surface of host cells. The PA receptor has recently been isolated and sequenced, and found to possess von Willebrand Factor-like regions. After docking on the surface of host cells, PA interacts with a protease present on the cell surface. The protease processes the large and inactive PA molecule into a smaller and active 63 kDa fragment. The C-terminal 63 kDa fragment (PA63) remains bound to the cell and the N-terminal 20 kDa (PA20) dissociates from PA63. The identity of the protease has been the focus of scant research effort, and it is poorly characterized. However, prior studies have shown that the protease has characteristics that suggest it is a host-derived serine protease. A possible serine protease candidate noted in the literature is related to furine (itself a serine protease), but other serine proteases, such as elastase, proteinase-3, clostripain, or trypsin are possible alternatives (Molloy, S. S. et al. J Biol Chem 267, 16396-16402 (1992)). This proteolytic cleavage and subsequent dissociation of PA20 confer two new properties on PA63: (1) the ability to oligomerize into a ring-shaped heptameric SDS-dissociable structure termed prepore and (2) the ability to bind EF and LF. Oligomers containing PA63-EF, PA63-LF, or a combination of PA63-EF and PA63-LF are endocytosed and trafficked to an acidic compartment, where the PA63 prepore inserts into the membrane and forms a pore. During or after pore formation, EF and LF are translocated across the endosomal membrane into the cytoplasm. EF is a calmodulin-dependent adenylate cyclase which may protect the bacteria from destruction by phagocytes. LF is a metalloprotease that can kill macrophages or, at lower concentrations, induce macrophages to overproduce cytokines, possibly resulting in death of the host. These heptamers function as the transport vehicle to deliver LF and EF inside of the cell. Once inside the cell, LF and EF initiate abnormalities in cell function.

Because of some of the difficulties and inadequacies of conventional therapy for tuburculosis, other mycobacterial infections, and anthrax, new therapeutic modalities are desirable.

The inventor discloses a novel method of use for serine protease inhibitors as therapeutic agents to treat infections caused by tuberculosis (TB) and *mycobacterium avium* complex (MAC). These are intracellular human pathogens that establish infection and prolonged latency by infecting and surviving within human macrophages. Therefore, blocking the internalization of TB or MAC within macrophages is a novel approach to therapy vs these infectious agents. In an infectivity assay, the inventors have shown that α1-antitrypsin significantly inhibited both TB and MAC infection of human monocyte-derived-macrophages (MDM).

A novel approach to nullify the action of anthrax toxin is to block access of the toxin to the interior of the cell by interfering with the action of the host-derived serine protease that resides on the cell surface.

This invention thus addresses a long-felt need for safe and effective methods of treatment of tuburculosis, other mycobacterial infections, other Gram negative and Gram positive bacterial infections, and anthrax.

SUMMARY OF THE INVENTION

The present invention provides methods for treating bacterial infections in a mammal comprising administering to a subject in need thereof of a therapeutically effective amount of a composition comprising a substance exhibiting mammalian α1-antitrypsin or inhibitor of serine protease activity or a functional derivative thereof; and a pharmaceutically acceptable excipient.

In one embodiment, the bacterial infections that may be treated or ameliorated using the compositions and methods of the invention are those infections caused by Gram negative bacterial organisms comprising *N. gonorrhoeae, N. meningitidis, M catarrhalis, H. influenzae, E. coli*, all *Klebsiela* spp., all *Enterobacter* spp., all *Serratia* spp., all *Salmonella* spp., all *Shigella* spp., *Proteus mirabilis, Proteus vulgaris*, all *Providencia* spp., all *Morganella* spp., all *Citrobacter* spp., all *Aeromonas* spp., all *Acinetobacter* spp., *Pseudomonas aeruginosa*, all *Pasteurella* spp., *Pseudomonas cepacia, Stenotrophomonas maltophilia, Y. enterocolitica* and other *Yersinoiiosis*, all *Legionella* spp., *P. multocida, H. ducreyeii*, all *Chlamyidia* spp., *Mycoplasma pneumoniae, Mycoplasma hominis, Bacteroides fragilis, P. melaminogenica*, all *Moraxella* spp., all *Bortedella* spp., or any combination thereof.

In another embodiment, the bacterial infections that may be treated or ameliorated using the compositions and methods of the invention are those infections caused by Gram positive bacterial organisms comprising *C. tetani, C. botulinum, C. difficile*, Group A, B C, and G *Streptococcus, Streptococcus pneumoniae, Streptococcus milleri* group, *Viridans streptococcus*, all *Listeria* spp., all *Staphylococcus* spp., *S. aureus* (MSSA), *S. aureus* (MRSA), *S. epidermidis, Enterococcus faecalis, Enterococcus faecium*, all *Clostridium* spp. including *C. diptheriea, C. jeikium*, all *Rhodococcus* spp., all *Leukonostoc* spp. or any combination thereof.

In yet another embodiment, the bacterial infections that may be treated or ameliorated using the compositions and methods of the invention are those infections caused by acid fast bacilli comprising *Mycobacterium tuberculosis*, and atypical *Mycobacteria* (*M. Avium, M. Intracellulare, M. Kansasii, M. Chelonei, M. fortuitum, M. scrofulaceum, M. ulceranis, M. leprae, M. xenopi, M. bovis, M. gordonae, M. haemophilum, M. marinum, M. genavense, M. avium* and *intracellulari*, and *M. simiae*), or any combination thereof.

The present invention provides methods for treating mycobacterial infections in a mammal comprising administering to a subject in need thereof a therapeutically effective amount of a composition comprising a substance exhibiting mammalian α1-antitrypsin or inhibitor of serine protease activity or a functional derivative thereof; and a pharmaceutically acceptable excipient.

In one embodiment, the *mycobacterium* inhibited from infecting macrophages comprises a *mycobacterium* from the genus *mycobacterium* that includes *M. tuberculosis M. bovis, M. leprae, M. avium-intracellulare, M. chelonei* (also known as borstelense and abscessus), *M. africanum, M. marinium* (also known as balnei and platypoeculis), *M. buruli* (also known as ulcerans), *M. fortuitum* (also known as giae, minetti, and ranae), *M. haemophilum, M. intracellulare, M. kansasii* (also known as luciflavum), *M. littorals* (also known as xenopi), *M. malmoense, M. marianum* (also known as scrofulaceum and paraffinicum), *M. simiae, M. szulgai, M. ulcerans, M. avium* (also known as brunense), *M. flavascens, M. lepraemurium, M. microti*, and *M. paratuberculosis* (which is the causative agent for Johne's Disease), *M. gordonae* (also known as aquae), *M. gastri, M. phlei* (also known as moelleri and as timothy *bacillus*), *M. nonchromogenicum, M. smegmatis, M. terrae, M. triviale*, and *M. vaccae*, or any combination thereof.

In another embodiment, the *mycobacterium* inhibited from infecting macrophages comprises a *mycobacterium* from the genus *mycobacterium* that includes non-tuberculosis mycobacteria that are divided into four groups comprising Runyon groups, selected from the group consisting of Group I (slow-growing photochromogens), Group II (slow-growing scotochromogens), Group III (slow-growing nonphotochromogens), and Group IV (rapidly-growing mycobacteria), or any combination thereof.

Therefore, in one aspect, the present invention provides methods of treating mycobacterial diseases dependent on the infection of macrophages.

Also provided is a method of inhibiting mycobacterial infection of macrophages, which comprises administering to a mammal susceptible to mycobacterial infection of macrophages an effective amount of a substance exhibiting mammalian α1-antitrypsin or inhibitor of serine protease activity. Without limiting to α1-antitrypsin, the substance may be a compound that inhibits proteinase-3, cathepsin G, elastase, or any other serine protease.

In a preferred embodiment the agent that inhibits mycobacterial infection of human monocyte-derived-macrophages comprises α1-antitrypsin. In addition, peptides of interest are homologous and analogous peptides. While homologues are natural peptides with sequence homology, analogues will be peptidyl derivatives, e.g., aldehyde or ketone derivatives of such peptides. Typical examples of analogues are TLCK or TPCK. Without limiting to α1-antitrypsin and peptide derivatives of α1-antitrypsin, compounds like oxadiazole, thiadiazole, CE-2072, UT-77, and triazole peptoids are preferred.

The agent that inhibits mycobacterial infection of human monocyte-derived-macrophages can also be an inhibitor of serine protease activity, an inhibitor of elastase, or an inhibitor of proteinase-3. The inhibitor of serine protease activity can include, but is not limited to, small organic molecules including naturally-occurring, synthetic, and biosynthetic molecules, small inorganic molecules including naturally-occurring and synthetic molecules, natural products including those produced by plants and fungi, peptides, variants of α1-antitrypsin, chemically modified peptides, and proteins. An inhibitor of serine protease activity has the capability of inhibiting the proteolytic activity of trypsin, elastase, kallikrein, and/or other serine proteases.

Also contemplated within the scope of the present invention is a method of preventing a deficiency of functional endogenous α1-antitrypsin levels in a patient susceptible to a mycobacterial infection of macrophages that is mediated by endogenous host serine protease or serine protease-like activity, by treating with a pharmaceutical composition in a pharmaceutically acceptable carrier comprising effective amounts of a substance exhibiting mammalian α1-antitrypsin or inhibitor of serine protease activity. The pharmaceutical composition can be a peptide or a small molecule, which exhibits α1-antitrypsin or inhibitor of serine protease activity.

In yet another aspect, the present invention provides a method for preventing a symptom of anthrax in a subject thought to be at risk for exposure to *Bacillus anthracis* comprising administering to the subject a pharmaceutically effective amount of a substance exhibiting mammalian "1-antitrypsin or inhibitor of serine protease activity, wherein said mammalian "1-antitrypsin or inhibitor of serine protease activity substance inhibits the endogenous host protease cell-surface processing of inactive large PA into the active smaller PA molecule, and wherein if the subject is exposed to *Bacillus anthracis*, a symptom of said exposure is prevented.

In another aspect, the present invention provides a method for preventing a symptom of anthrax in a subject suspected of having been exposed to *Bacillus anthracis* comprising administering to the subject a pharmaceutically effective amount of a substance exhibiting mammalian α1-antitrypsin or inhibitor of serine protease activity, wherein said mammalian α1-antitrypsin or inhibitor of serine protease activity substance inhibits the endogenous host protease cell-surface processing of inactive large PA into the active smaller PA molecule, and wherein if the subject is exposed to *Bacillus anthracis*, a symptom of said exposure is prevented.

In another aspect, the present invention provides a method for ameliorating a symptom of anthrax in a subject in need of said amelioration comprising administering to the subject a pharmaceutically effective amount of a substance exhibiting mammalian α1-antitrypsin or inhibitor of serine protease activity, wherein said mammalian α1-antitrypsin or inhibitor of serine protease activity substance inhibits the endogenous host protease cell-surface processing of inactive large PA into the active smaller PA molecule.

In the above-recited methods, the symptom of anthrax that is inhibited or prevented is selected from the group consisting of cutaneous ulceration, edema, and escar formation, or any combination thereof.

In one embodiment, the methods of the present invention are used to prevent or ameliorate a symptom of cutaneous, gastrointestinal, and/or inhalation anthrax. In one embodiment, the methods of the present invention are used to prevent or ameliorate a symptom of anthrax selected from the group consisting of malaise, fever, dry cough, myalgias, and chest pains, ventilatory compromise, sweating, widening of the mediastinum on radiographic studies, edema of the neck and chest, necrotizing mediastinal lymphadenitis, non-pitting edema, eschar, nausea, vomiting, fever, abdominal pain, bloody diarrhea, mucosal ulcerations, hemorrhagic mesenteric lymphadenitis, or any combination thereof.

In yet another aspect, the present invention is directed to a method of relieving or ameliorating the pain or symptoms associated with any one or more of the above-identified bacterial diseases or indications, mycobacterial diseases or indications, or anthrax infection in a mammal suffering from any one or more of the above-identified bacterial diseases or indications, mycobacterial diseases or indications, or anthrax infection which comprises administering to the mammal in need thereof a therapeutically effective pain or symptom-reducing amount of a pharmaceutical composition comprising effective amounts of a substance exhibiting mammalian α1-antitrypsin or inhibitor of serine protease activity, either alone or in combination with one or more anti-inflammatory compounds or immunomodulatory agents; and a pharmaceutically acceptable carrier or excipient, wherein said mammalian α1-antitrypsin or inhibitor of serine protease activity substance is sufficient to inhibit or ameliorate the bacterial disease or indication, mycobacterial disease or indication, or anthrax infection of the host.

In one embodiment, the reduction or inhibition of pain and/or symptoms associated with one or more of each of the above-recited mycobacterial indications, bacterial infections or anthrax infections is on the order of about 10-20% reduction or inhibition. In another embodiment, the reduction or inhibition of pain is on the order of 30-40%. In another embodiment, the reduction or inhibition of pain is on the order of 50-60%. In yet another embodiment, the reduction or inhibition of the pain associated with each of the recited indications is on the order of 75-100%. It is intended herein that the ranges recited also include all those specific percentage amounts between the recited range. For example, the range of about 75 to 100% also encompasses 76 to 99%, 77 to 98%, etc, without actually reciting each specific range therewith.

Accordingly, the overall aspect of the present invention to provide compounds that exhibit inhibitory activity toward serine proteases. Thus, it should be recognized that this invention is applicable to the control of catalytic activity of serine proteases in any appropriate situation including, but not necessarily limited to, medicine, biology, agriculture, and microbial fermentation.

One aspect of the present invention is to provide clinically acceptable serine protease inhibitors with recognized utility and exhibiting relatively high activity at relatively low concentrations.

In one embodiment, the α1-antitrypsin used in the methods and compositions of the present invention comprises Aralast® (Baxter), Zemaira® (Aventis Behring), Prolastin® (Bayer), Aprotonin® or Trasylol® (Bayer Pharmaceutical Corporation) and Ulinistatin® (Ono Pharmaceuticals, Inc.), or any combination thereof.

The present invention provides methods for therapeutically or prophylactically treating bacterial infections in a subject.

The method for therapeutically treating bacterial or mycobacterial infections comprises the step of administering pharmaceutically effective amounts of a substance exhibiting mammalian α1-antitrypsin or inhibitor of serine protease activity or derivative thereof to the subject after occurrence of the bacterial or mycobacterial disease.

The method for prophylactically treating bacterial or mycobacterial infections comprises the step of administering pharmaceutically effective amounts of a substance exhibiting mammalian α1-antitrypsin or inhibitor of serine protease activity or derivative thereof to the subject prior to the occurrence of the bacterial or mycobacterial disease.

Either methodology inhibits the bacterial infection or the mycobacterial infection of macrophages.

For each of the above-recited methods of the present invention, the therapeutically effective amount of one or more substances exhibiting mammalian α1-antitrypsin or inhibitor of serine protease activity or a functional derivative thereof may be administered to a subject in need thereof in conjunction with a therapeutically effective amount of one or more anti-microbacterial drugs and/or inflammatory compounds and/or a therapeutically effective amount of one or more immunomodulatory agents.

In certain embodiments of the method of the present invention, the antiinflammatory compound or immunomodulatory drug comprises interferon; interferon derivatives comprising betaseron, .beta.-interferon; prostane derivatives comprising iloprost, cicaprost; glucocorticoids comprising cortisol, prednisolone, methylprednisolone, dexamethasone; immunsuppressives comprising cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives comprising ACTH and analogs thereof; soluble TNF-receptors; TNF-antibodies; soluble receptors of interleukines, other cytokines, T-cell-proteins; antibodies against receptors of interleukines, other cytokines, T-cell-proteins; and calcipotriols and analogues thereof taken either alone or in combination.

The present invention also relates to the combined use of the pharmaceutical composition exhibiting mammalian α1-antitrypsin or inhibitor of serine protease activity in combination with one or more antibacterial or antiviral compositions or any combination thereof for treating any one of the aforementioned bacterial or mycobacterial diseases, or any combination thereof.

In each of the above-recited methods, the mammalian α1-antitrypsin or inhibitor of serine protease activity substance may be part of a fusion polypeptide, wherein said fusion polypeptide comprises mammalian α1-antitrypsin or a substance with inhibitor of serine protease activity and an amino acid sequence heterologous to said mammalian α1-antitrypsin or inhibitor of serine protease activity substance.

In certain embodiments, the fusion polypeptide contemplated for use in the methods of the present invention comprise a human immunoglobin constant region, such as for example, a human IgG1 constant region, including a modified human IgG1 constant region wherein the IgG1 constant region does not bind the Fc receptor and/or does not initiate antibody-dependent cellular cytotoxicity (ADCC) reactions.

In yet other embodiments, the fusion polypeptide contemplated for use in the methods of the present invention can additionally comprise an amino acid sequence that is useful for identifying, tracking or purifying the fusion polypeptide, e.g., the fusion polypeptide can further comprise a FLAG or HIS tag sequence. The fusion polypeptide can additionally further comprise a proteolytic cleavage site which can be used to remove the heterologous amino acid sequence from the mammalian α1-antitrypsin or the substance with inhibitor of serine protease activity. In each of the above-recited compositions and methods of the invention the agent that inhibits the bacterial infection, mycobacterial infection of human monocyte-derived-macrophages or anthrax comprises α1-antitrypsin. In addition, peptides of interest are homologous and analogous peptides. While homologues are natural peptides with sequence homology, analogues will be peptidyl derivatives, e.g., aldehyde or ketone derivatives of such peptides. Typical examples of analogues are TLCK or TPCK. Without limiting to α1-antitrypsin and peptide derivatives of α1-antitrypsin, compounds like oxadiazole, thiadiazole, CE-2072, UT-77, and triazole peptoids are preferred.

In other embodiments, the agent that inhibits the bacterial infection, the mycobacterial infection of human monocyte-derived-macrophages and/or anthrax can also be an inhibitor of serine protease activity, an inhibitor of elastase, or an inhibitor of proteinase-3. The inhibitor of serine protease activity can include, but is not limited to, small organic molecules including naturally-occurring, synthetic, and biosynthetic molecules, small inorganic molecules including naturally-occurring and synthetic molecules, natural products including those produced by plants and fungi, peptides, variants of α1-antitrypsin, chemically modified peptides, and proteins. An inhibitor of serine protease activity has the capability of inhibiting the proteolytic activity of trypsin, elastase, kallikrein, and/or other serine proteases.

In one embodiment of the invention, the peptide can be protected or derivitized in various ways, e.g., N-terminal acylation, C-terminal amidation, cyclization, etc. In a specific embodiment, the N-terminus of the peptide is acetylated.

The peptides of interest are homologous and analogous peptides. While homologues are natural peptides with sequence homology, analogues will be peptidyl derivatives, e.g., aldehyde or ketone derivatives of such peptides. Without limiting to AAT and peptide derivatives of AAT, the compounds like oxadiazole, thiadiazole and triazole peptoids and substances comprising certain phenylenedialkanoate esters are preferred.

In each of the above-recited methods, the mammalian α1-antitrypsin or inhibitor of serine protease activity substance contemplated for use within the methods of the present invention further comprises a series of peptides comprising carboxyterminal amino acid peptides corresponding to AAT. These pentapeptides can be represented by a general formula (I): I-A-B-C-D-E-F-G-H-II, wherein I is Cys or absent; A is Ala, Gly; Val or absent; B is Ala, Gly, Val, Ser or absent; C is Ser, Thr or absent; D is Ser, Thr, Ans, Glu, Arg, Ile, Leu or absent; E is Ser, Thr, Asp or absent; F is Thr, Ser, Asn, Gln, Lys, Trp or absent; G is Tyr or absent; H is Thr, Gly, Met, Met(O), Cys, Thr or Gly; and II is Cys, an amide group, substituted amide group, an ester group or absent, wherein the peptides comprise at least 4 amino acids and physiologically acceptable salts thereof. Among this series of peptides, several are equally acceptable including FVFLM (SEQUENCE ID NO. 1), FVFAM (SEQUENCE ID NO. 2), FVALM (SEQUENCE ID NO. 3), FVFLA (SEQUENCE ID NO. 4), FLVFI (SEQUENCE ID NO. 5), FLMII (SEQUENCE ID NO. 6), FLFVL (SEQUENCE ID NO. 7), FLFVV (SEQUENCE ID NO. 8), FLFLI (SEQUENCE ID NO. 9), FLFFI (SEQUENCE ID NO. 10), FLMFI (SEQUENCE ID NO. 11), FMLLI (SEQUENCE ID NO. 12), FIIMI (SEQUENCE ID NO. 13), FLFCI (SEQUENCE ID NO. 14), FLFAV (SEQUENCE ID) NO. 15), FVYLI (SEQUENCE ID NO. 16), FAFLM (SEQUENCE ID NO. 17), AVFLM (SEQUENCE ID NO. 18), and any combination thereof.

In yet another embodiment, these peptides can be represented by a general formula (II): NT-X1-X2-X3-X4-X5-CT or a physiologically acceptable salt thereof, in which NT comprises an amino acid residue positioned at the peptide's N-terminal end, including C, an acetyl group, or a succinyl group, provided that NT can also be absent; X1 comprises an amino acid residue, including F or A; X2 comprises an amino acid residue, including C, V, L, M, I, A, C, or S; X3 comprises an amino acid residue, including F, A, V, M, L, I, Y, or C; X4 comprises an amino acid residue, including L, A, F, I, V, M, C, G, or S; X5 comprises an amino acid residue, including M, A, I, L, V, F, or G; and CT comprises an amino acid residue positioned at the peptide's C-terminal end, including C, an amide group, a substituted amide group, or an ester group, provided that CT can also be absent, and in which the amino acid residue can be either an L- or a D-stereoisomeric configuration. These peptides comprise at least 5 amino acids and physiologically acceptable salts thereof. Amino acids in the formula are abbreviated as 1-letter and corresponding 3-letter codes are as follow: Alanine is A or Ala; Arginine R or Arg, Asparagine N or Asn; Aspartic acid D or Asp; Cysteine C or Cys; Glutamine Q or Gln; Glutamic acid E or Glu; Glycine G or Gly; Histidine H or His; Isoleucine I or Ile; Leucine L or Leu; Lysine K or Lys; Methionine M or Met; Phenylalanine F or Phe; Proline P or Pro; Serine S or Ser; Threonine T or Thr; Tryptophan W or Trp; Tyrosine Y or Tyr; and Valine V or Val.

In each of the above-recited methods, the mammalian α1-antitrypsin or inhibitor of serine protease activity substance contemplated for use within the methods of the present invention further comprises a series of peptides comprising amino acid peptides corresponding to portions or fragments of AAT. For example, and not by way of limitation, amino acid peptides corresponding to 10 amino acid fragments of AAT are specifically contemplated for use in the composition and methods of the present invention. In particular, amino acid peptides MPSSVSWGIL (SEQUENCE ID NO. 19); LAGLCCLVPV (SEQUENCE II) NO. 20) SLAEDPQGDA (SEQUENCE ID NO. 21); AQKTDTSHHD (SEQUENCE ID NO. 22) QDHPTFNKIT (SEQUENCE ID NO. 23); PNLAEFAFSL (SEQUENCE ID NO. 24); YRQLAHQSNS (SEQUENCE ID NO. 25); TNIFFSPVSI (SEQUENCE ID NO. 26); ATAFAMLSLG (SEQUENCE ID NO. 27); TKADTHDEIL (SEQUENCE ID NO. 28); EGLNFNLTEI (SEQUENCE ID NO. 29); PEAQIHEGFQ (SEQUENCE ID) NO. 30); ELLRTLNQPD (SEQUENCE ID NO. 31); SQLQLTTGNG (SEQUENCE ID NO. 32); LFLSEGLKLV (SEQUENCE ID NO. 33); DKFLEDVKKL (SEQUENCE ID NO. 34); YHSEAFTVNF (SEQUENCE ID NO. 35); GDHEEAKKQI (SEQUENCE ID NO. 36); NDYVEKGTQG (SEQUENCE ID NO. 37); KIVDLVKELD (SEQUENCE ID NO. 38); RDTVFALVNY (SEQUENCE ID NO. 39); IFFKGKWERP (SEQUENCE ID NO. 40); FEVKDTEDED (SEQUENCE ID NO. 41); FHVDQVTTVK (SEQUENCE ID NO. 42); VPMMKRLGMF (SEQUENCE ID NO. 43); NIQHCKKLSS (SEQUENCE ID NO. 44); WVLLMKYLGN (SEQUENCE ID NO. 45); ATAIFFLPDE (SEQUENCE ID NO. 46); GKLQHLENEL (SEQUENCE ID NO. 47); THDIITKFLE (SEQUENCE ED NO. 48); NEDRRSASLH (SEQUENCE ID NO. 49); LPKLSITGTY (SEQUENCE ID NO. 50); DLKSVLGQLG (SEQUENCE ID NO. 51); ITKVFSNGAD (SEQUENCE ID NO. 52); LSGVTEEAPL (SEQUENCE ID NO. 53); KLSKAVHKAV (SEQUENCE ID NO. 54); LTIDEKGTEA (SEQUENCE ID NO. 55); AGAMFLEAIP (SEQUENCE ID NO. 56); MSIPPEVKFN (SEQUENCE ID NO. 57); KPFVFLMIEQ (SEQUENCE ID NO. 58); NTKSPLFMGK (SEQUENCE ID NO. 59); VVNPTQK (SEQUENCE ID NO. 60), or any combination thereof. It is specifically intended that the AAT peptides recited contemplated for use in the compositions and methods of the present invention are also intended to include any and all of those specific AAT peptides other than the 10 amino acid AAT peptides of SEQ ID NO. 1 depicted supra. For example, while AAT peptides amino acids 1-10, amino acids 11-20, amino acids 21-30, etc of SEQ ID NO. 1 have been enumerated herein, it is intended that the scope of the compositions and methods of use of same specifically include all of the possible combinations of AAT peptides such as amino acids 2-12, amino acid 3-13, 4-14, etc. of SEQ ID NO. 1, as well as any and all AAT peptide fragments corresponding to select amino acids of SEQ ID NO. 1, without actually reciting each specific AAT peptide of SEQ ID NO. 1 therewith. Thus, by way of illustration, and not by way of limitation, Applicants are herein entitled to possession of compositions based upon any and all AAT peptide variants based upon the amino acid sequence depicted in SEQ ID NO. 1 and use of such compositions in the methods of the present invention.

The AAT and similarly active compounds contemplated for use in the compositions and methods of the present invention may be identified by a series of assays wherein a compound (AAT) will exhibit inhibitory activity versus control in an assay. One of these assays comprises blocking infection of human monocyte derived macrophages in an in vitro model of infection as described in detail in Example 1 of the detailed description of this disclosure.

In one embodiment, with respect to the use of the compositions and methods of the present invention to prevent or ameliorate a symptom caused by either *Bacillus anthracis, Corynebacterium diptheriae*, or *Pseudomonas aeruginosa*, specifically excluded within the scope of the present invention are those furin endoprotease inhibitors comprising an α1-antitrypsin variant having an amino acid sequence comprising the amino acids of the native α1-antitrypsin molecule, except that the sequence at position 355-358 of the native protein (-Ala-11e-Pro-Met-) is changed to the novel sequence -Arg-X-X-Arg-, wherein X is any amino acid, at positions 355-358 of the native α1-antitrypsin amino acid sequence as disclosed in U.S. Pat. Nos. 5,604,201 and 6,022,855.

Also specifically excluded within the scope of the compositions and methods of the present invention to prevent or ameliorate a symptom caused by either *Bacillus anthracis, Corynebacterium diptheriae*, or *Pseudomonas aeruginosa* are those α1-antitrypsin Portland variants wherein the amino acid sequence at positions 355-358 of the α1-antitrypsin amino acid Portland sequence is -Arg-11e-Pro-Arg- as disclosed in U.S. Pat. Nos. 5,604,201 and 6,022,855.

Also specifically excluded within the scope of the compositions and methods of the present invention to prevent or ameliorate a symptom caused by either *Bacillus anthracis, Corynebacterium diptheriae*, or *Pseudomonas aeruginosa* are peptides having amino acid sequences of about 4 to about 100 amino acids in length comprising the amino acid sequence -Arg-Xaa-Xaa-Arg-, wherein each Xaa is any amino acid as is disclosed in U.S. Pat. Nos. 5,604,201 and 6,022,855.

In yet another embodiment, with respect to the use of the compositions and methods of the present invention to prevent or ameliorate a symptom of anthrax, specifically excluded within the scope of the present invention are those furin endoprotease inhibitors comprising HexArg as disclosed in Miroslav S. Sarac et al. (Infection and Immunity, January 2004, p. 602-605, Vol. 72, No. 1 Protection against Anthrax Toxemia by Hexa-D-Arginine In Vitro and In Vivo).

The invention further provides pharmaceutical compositions comprising such agents.

The preferred doses for administration can be anywhere in a range between about 10 ng and about 10 mg per ml or mg of the formulation. The therapeutically effective amount of AAT peptides or drugs that have similar activities as AAT or peptides drug can be also measured in molar concentrations and may range between about 1 nM and about 10 mM. The formulation is also contemplated in combination with a pharmaceutically or cosmetically acceptable carrier. The precise doses can be established by well known routine clinical trials without undue experimentation.

In one aspect of the invention, the pharmaceutical compositions of the present invention are administered orally, systemically, via an implant, intravenously, topically, intrathecally, intracranially, intraventricularly, by inhalation or nasally.

In certain embodiments of the methods of the present invention, the subject or mammal is a human.

In other embodiments of the methods of the present invention, the subject or mammal is a veterinary and/or a domesticated mammal.

There has been thus outlined, rather broadly, the important features of the invention in order that a detailed description thereof that follows can be better understood, and in order that the present contribution can be better appreciated. There are additional features of the invention that will be described hereinafter.

In this respect, before explaining at least one embodiment of the invention in detail, it is to be understood that the invention is not limited in its application to the details as set forth in the following description and figures. The present invention is capable of other embodiments and of being practiced and carried out in various ways. Additionally, it is to be understood that the terminology and phraseology employed herein are for the purpose of description and should not be regarded as limiting.

As such, those skilled in the art will appreciate that the conception, upon which this disclosure is based, can readily be used as a basis for designing other methods for carrying out the several features and advantages of the present invention. It is important, therefore, that the claims be regarded as including such equivalent constructions insofar as they do not depart from the spirit and scope of the present invention.

DETAILED DESCRIPTION OF THE INVENTION

Standard Methods

Figure 1:
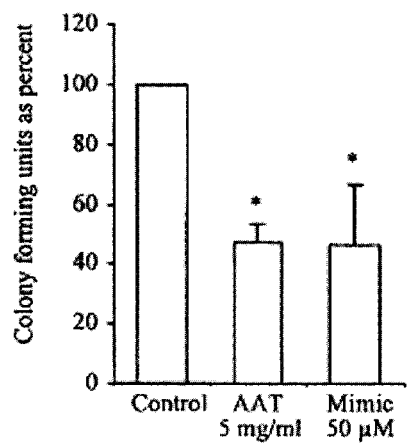
FIG. 1 illustrates the effect of α-1-antitrypsin (AAT) and AAT mimic on *mycobacterium avium* complex (mac) infection of human monocyte-derived macrophages (n=4).

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Therapeutic Methods

The present invention provides methods for treating mycobacterial infections comprising administering to a subject in need thereof of a therapeutically effective amount of a composition comprising an effective amount of a substance exhibiting mammalian α1-antitrypsin or inhibitor of serine protease activity or a functional derivative thereof; and a pharmaceutically acceptable excipient.

According to the methods of the present invention, mycobacterial infection of macrophages is inhibited to obtain important therapeutic benefits.

Therefore, administration of a dosage of the invention composition, i.e., α1-antitrypsin, or a fragment, derivative or analog thereof, can be beneficial for the treatment of mycobacterial diseases or disorders. In a preferred aspect, the agent is an analog of α1-antitrypsin that can cross the blood brain barrier, which would allow for intravenous or oral administration. Many strategies are available for crossing the blood brain barrier, including but not limited to, increasing the hydrophobic nature of a molecule; introducing the molecule as a conjugate to a carrier, such as transferrin, targeted to a receptor in the blood brain barrier; and the like. In another embodiment, the agent can be administered intracranially or, more directly, intraventricularly. In yet another embodiment, the agent can be administered by way of inhalation or nasally.

In a further embodiment, the methods and compositions of the invention are useful in the therapeutic treatment of mycobacterial diseases or disorders of the immune system. In a yet further embodiment, diseases can be prevented by the timely administration of the agent of the invention as a prophylactic, prior to onset of symptoms, or signs, or prior to onset of severe symptoms or signs of a mycobacterial disease. Thus, a patient at risk for a particular mycobacterial disease can be treated with serine protease inhibitors, for example, (Benzyloxycarbonyl)-L-Valyl-N-[1-(3-(5-(3-Trifluoromethylbenzyl)-1,2,4-ox-adiazolyl)carbonyl)-2-(S)-Methylpropyl]-L-Prolinamide; as a precautionary measure.

The effective dose of the agent of the invention, and the appropriate treatment regime, can vary with the indication and patient condition, and the nature of the molecule itself, e.g., its in vivo half life and level of activity. These parameters are readily addressed by one of ordinary skill in the art and can be determined by routine experimentation.

The preferred doses for administration can be anywhere in a range between about 0.01 mg and about 20 mg per ml of biologic fluid of treated patient. The therapeutically effective amount of α1-antitrypsin, peptides, or drugs that have similar activities as α1-antitrypsin or peptides can be also measured in molar concentrations and can range between about 1 nM to about 2 mM.

Serine Protease Inhibitors

It is to be understood that the present invention is not limited to the examples described herein, and other serine proteases known in the art can be used within the limitations of the invention. For example, one skilled in the art can easily adopt inhibitors as described in WO 98/24806, which discloses substituted oxadiazole, thiadiazole and triazole as serine protease inhibitors. U.S. Pat. No. 5,874,585 discloses substituted heterocyclic compounds useful as inhibitors of serine proteases; including: (benzyloxycarbonyl)-L-valyl-N-[1-(3-(5-(3-trifluoro-methylbenzyl)-1,2,4-oxa diazolyl)carbonyl)-2-(S)-methylpropyl]-L-prolinami-debenzyloxycarbonyl)-L-valyl-N-[1-(3-(5-(2-phenylethyl)-1,2,4-oxadiazolyl-)carbonyl)-2-(S)-methylpropyl]-L-prolinamide; (benzyloxycarbonyl)-L-valyl-N-[1-(3-(5-(2-methoxybenzyl)-1,2,4-oxadiazolyl)carbonyl)-2-(S)-methylpropy-1]-L-prolinamide; (benzyloxycarbonyl)-L-valyl-N-[1-(3-(5-(trifluoromethyl)- -1,2,4-oxadiazolyl)carbonyl)-2-(S)-methylpropyl]-L-prolinamide; (benzyloxycarbonyl)-L-valyl-N-[1-(3-(5-(methyl)-1,2,4-oxadiazolyl)carbonyl)-2-(S)-Methylpropyl]-L-Prolinamide; (Benzyloxycarbonyl)-L-Valyl-N-[1-(3-(5-(difluoromethyl)-1,2,4-oxadiazolyl)carbonyl)-2-(S)-Methylpropyl]-L-Prolinamide; (Benzyloxycarbonyl)-L-Valyl-N-[1-(3-(5-(benzyl)-1,2,4-oxadiazolyl-)carbonyl)-2-(S)-Methylpropyl]-L-Prolinamide; (Benzyloxycarbonyl)-L-Valyl-N-[1-(3-(5-(3-methoxybenzyl)-1,2,4-oxadiazolyl)carbonyl)-2-(S)-Methylpropy-1]-L-Prolinamide; (Benzyloxycarbonyl)-L-Valyl-N-[1-(3-(5-(2,6-difluorobenzyl)-1,2,4-oxadiazolyl)carbonyl)-2-(S)-Methylpropyl]-L-Prolinamide; (Benzyloxycarbonyl)-L-Valyl-N-[1-(3-(5-(trans-styryl)-1,2,4-oxadiazolyl)carbonyl)-2-(S)-Methylpropyl]-L-Prolinamide; (Benzyloxycarbonyl)-L-Valyl-N-[1-(3-(5-(trans-4-Trifluoro methylstyryl)-1,2,4-oxadiazolyl)carbonyl)-2-(S-)-Methylpropyl]-L-Prolinamide; (Benzyloxycarbonyl)-L-Valyl-N-[1-(3-(5-(trans-4-Methoxystyryl)-1,2,4-oxadiazolyl)carbonyl)-2-(S)-Methylpropyl]-L-Prolinamide; (Benzyloxycarbonyl)-L-Valyl-N-[1-(3-(5-(3-Thienylmethyl)-1,2,4-ox-adiazolyl)carbonyl)-2-(S)-Methylpropyl]-L-Prolinamide; (Benzyloxycarbonyl)-L-Valyl-N-[1-(3-(5-(Phenyl)-1,2,4-oxadiazolyl)carbony-1)-2-(S)-methylpropyl]-L-prolinamide; and (Benzyloxycarbonyl)-L-Valyl-N-[1- -(3-(5-(3-Phenylpropyl)-1,2,4-oxadiazolyl)-carbonyl)-2-(S)-Methylpropyl]-L-Prolinamide. U.S. Pat. No. 5,216,022 teaches other small molecules useful for the practice of this invention, including: Benzyloxycarbonyl-L-valyl-N-[1-(2-[5-(3-methylbenzyl)-1,3,4-oxadiazolyl]carbonyl)-2-(S)-methylpropyl-]-L-prolinamide (also known as CE-2072), Benzyloxycarbonyl-L-valyl-N-[1-(2- -(3-methylbenzyl)-1,3,4-oxadiazolyl]carbonyl)-2-(S)-methylpropyl]-L-prolinamide; Benzyloxycarbonyl-L-valyl-N-[-(2-(5-(methyl)-1,3,4-oxadiazoly]carbonyl)-2-(S)-methylpropyl]-L-prolinamide; Benzyloxycarbonyl-L-valyl-N-[1-(2- -(5-(3-trifluoromethylbenzyl)-1,3,4-oxadiazolyl]carbonyl)-2-(S)-methylpropyl]-L-prolinamide; (Benzyloxycarbonyl)-L-valyl-N-[1-(2-(5-(4-Dimethylamino benzyl)-1,3,4-oxadiazolyl]carbonyl)-2-(S)-methylpropyl]-L-prolinamide; Benzyloxycarbonyl-L-valyl-N-[1-(2-(5-(1-napthylenyl)-1,3,4-oxadiazolyl]carbonyl)-2-(S)-methylpropyl]-L-prolinamide; (Benzyloxycarbonyl)-L-valyl-[1- -(3-(5-(3,4-methylenedioxybenzyl)-1,2,4-oxadiazolyl)carbonyl)-2-(S)-methylpropyl]-L-prolinamide; Benzyloxycarbonyl-L-valyl-N-[1-(3-(5-(3,5-dimethyl-benzyl)-1,2,4-oxadiazolyl)carbonyl)-2-(S)-methylpropyl]-L-prolinamide; (Benzyloxycarbonyl)-L-valyl-N-[1-(3-(5-(3,5-dimethoxybenzyl)-1,2,4-oxadiazolyl)carbonyl)-2-(S)-methylpropyl]-L-prolinamide; (Benzyloxycarbonyl)-L-v-alyl-N-[1-(3-(5-(3,5-ditrifluoromethylbenzyl)-1,2,4-oxadiazolyl]carbonyl)-2-(S)-methylpropyl]-L-prolinamide; (Benzyloxycarbonyl)-L-valyl-N-[1-(3-(5-(3-methylbenzyl)-1,2,4-oxadiazolyl]carbonyl)-2-(S)-methylpropyl]-L-prolinamide; (Benzyloxycarbonyl)-L-valyl-N-[1-(3-(5-(biphenylmethine)-1,2,4-oxadiazolyl]carbonyl)-2-(S)-methylpropyl]-L-prolinamide; (Benzyloxycarbonyl)-L-valyl-N-[1-(3-(5-(4-phenylbenzyl)-1,2,4-oxadiazolyl-]carbonyl)-2-(S)-methylpropyl]-L-prolinamide; (Benzyloxycarbonyl)-L-valyl-N-[1-(3-(5-(3-phenylbenzyl)-1,2,4-oxadiazolyl]carbonyl)-2-(S)-methylpropyl-]-L-prolinamide; (Benzyloxycarbonyl)-L-valyl-N-[1-(3-(5-(3-phenoxybenzyl)-1,2,4-oxadiazolyl]carbonyl)-2-(S)-methylpropyl]-L-prolinamide; (Benzyloxycarbonyl)-L-valyl-N-[1-(3-(5-(cyclohexylmethylene)-1,2,4-oxadiazolyl]carbonyl)-2-(S)-methylpropyl]-L-prolinamide; (Benzyloxycarbonyl)-L-v-alyl-N-[1-(3-(5-(3-trifluoromethyldimethylmethylene)-1,2,4-oxadiazolyl]carbonyl)-2-(S)-methylpropyl]-L-prolinamide; (Benzyloxycarbonyl)-L-valyl-N-[1-(3-(5-(1-napthylmethylene)-1,2,4-oxadiazolyl]carbonyl)-2-(S)-methylpropyl-]-L-prolinamide; (Benzyloxycarbonyl)-L-valyl-N-[1-(3-(5-(3-pyridylmethyl)-1,2,4-oxadiazolyl]carbonyl)-2-(S)-methylpropyl]-L-prolinamide; (Benzyloxycarbonyl)-L-valyl-N-[1-(3-(5-(3,5-diphenylbenzyl)-1,2,4-oxadiazolyl]carbonyl)-2-(S)-methylpropyl]-L-prolinamide; (Benzyloxycarbonyl)-L-valyl-N-[1-(3-(5-(4-dimethylaminobenzyl)-1,2,4-oxadiazolyl]carbonyl)-2-(S)-methylpropyl]-L-prolinamide; 2-(5-[(Benzyloxycarbonyl)amino]-6-oxo-2-(4-fluorophenyl)-1,6-dihydro-1-pyrimidinyl]-N-[1-(3-(5-(3-trifluoromethylbenzyl)- -1,2,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(3-(5- -(3-trifluoromethylbenzyl)-1,2,4-oxadiazolyl]carbonyl)-2-(S)-methylpropyl]-acetamide; 2-[5-[(Benzyloxycarbonyl)amino]-6-oxo-2-(4-fluorophenyl)-1,6-dihydro-1-pyrimidinyl]-N-[1-(2-(5-(3-methylbenzyl)-1,3,4-oxadiazolyl]carbonyl)-(S)-2-methylpropyl]acetamide; 2-(5-Amino-6-oxo-2-(4-fluorophenyl)-1,6-dihydro-1-pyrimidinyl]-N-[1-(2-(5-(3-methylbenzyl)-1,3,4-oxadiazolyl]carbonyl)-2-methylpropyl]acetamide; (Pyrrole-2-carbonyl)-N-(benzyl)glycyl-N-[1-(-2-(5-(3-methylbenzyl)-1,3,4-oxadiazolyl]carbonyl)-2-(S)-methylpropyl]amide-; (Pyrrole-2-carbonyl)-N-(benzyl)glycyl-N-[1-(3-(5-(3-trifluoromethylbenzyl)]-1,2,4-oxadiazolyl)-(S)-methylpropyl]amide; (2S,5S)-5-Amino-1,2,4,5,6,7- -hexahydroazepino-[3,2,1]-indole-4-one-carbonyl-N-[1-(2-(5-(3-methylbenzyl-)-1,3,4-oxadiazolyl]carbonyl)-(R,S)-2-methylpropyl]amide; BTD-[1-(2-(5-(3-methylbenzyl)-1,3,4-oxadiazolyl]carbonyl)-2-(S)-methylpropyl]amide; (R,S)-3-Amino-2-oxo-5-phenyl-1,4,-benzodiazepine-N-[1-(2-(5-(3-methylbenzyl)-1,3,4-oxadiazolyl]carbonyl)-2-(S)-methylpropyl]acetamide; (Benzyloxycarbonyl)-L-valyl-2-L-(2,3-dihydro-1H-indole)-N-[1-(2-(5-(3-methylbenzyl)-1,3,4-oxadiazolyl]carbonyl)-2-(S)-methylpropyl]amide; (Benzyloxycarbonyl)-L-valyl-2-L-(2,3-dihydro-1H-indole)-N-[1-(3-(5-(3-trifluoromethylbenzyl)-1,2,4-oxadiazolyl]carbonyl)-2-(S)-methylpropyl]amide; Acetyl-2-L-(2,3-dihydro-1H-indole)-N-[1-(2-(5-(3-methylbenzyl)-1,3,4-oxadiazolyl]carbonyl)-2-(S)-methylpropyl]amide; 3-(S)-(Benzyloxycarbonyl)amino-)-.epsilon.-lactam-N-[1-(2-(5-(3-methylbenzyl)-1,3,4-oxadiazolyl]carbonyl-)-2-(S)-methylpropyl]acetamide; 3-(S)-(Amino)-.epsilon.-lactam-N-[1-(2-(5-(3-methylbenzyl)-1,3,4-oxadiazolyl]carbonyl)-2-(S)-methylpropyl]acetamide trifluoroacetic acid salt; 3-(S)-[(4-morpholino carbonyl-butanoyl)amino]-.epsilon.-lactam-N-[1-(2-(5-(3-methylbenzyl)-1,3,4-oxadiazolyl]carbonyl)-2- -(R,S)- methylpropyl]acetamide; 6-[4-Fluorophenyl]-.epsilon.-lactam-N-[1-(2- -(5-(3-methylbenzyl)-1,3,4-oxadiazolyl]carbonyl)-2-(S)-methylpropyl]acetamide; 2-(2-(R,S)-Phenyl-4-oxothiazolidin-3-yl]-N-[1-(2-(5-(3-methylbenzyl)-1,3,4-oxadiazolyl]carbonyl)-2-(S)-methylpropyl]acetamide; 2-(2-(R,S)-phenyl-4-oxothiazolidin-3-yl]-N-[1-(2-(5-(3-methylbenzyl)-1,3,-4-oxadiazolyl]hydroxymethyl)-2-(S)-methylpropyl]acetamide; 2-(2-(R,S)-Benzyl-4-oxothiazolidin-3-yl]-N-[1-(2-(5-(3-methylbenzyl)-1,3,-4-oxadiazolyl]carbonyl)-2-(S)-methylpropyl]-acetamide; 2-(2-(R,S)-Benzyl-4-oxothiazolidin-3-yl oxide]-N-[1-(3-(5-(3-trifluoromethylbenzyl)-1,2,4-oxadiazolyl]carbonyl)-2-(R,S,)-methylpropyl]acetamide; (1-Benzoyl-3,8-quinazolinedione)-N-[1-(2-(5-(3-methylbenzyl)-1,3,4-oxadiazolyl]carbonyl)-2-(S)-methylpropyl]acetamide; (1-Benzoyl-3,6-piperazinedione)-N-[1-(2-(5-(3-methylbenzyl)-1,3,4-oxadiazolyl]carbonyl)-2-(S)-methylpropyl]acetamide; (1-Phenyl-3,6-piperazinedione)-N-[1-(2-(5-(3-methylbenzyl)-1,3,4-oxadiazolyl]carbonyl)-2-(S)-methylpropyl] acetamide; [(1-Phenyl-3,6-piperazinedione)-N-[1-(3-(5-(3-trifluoromethylbenzyl)-1,2,-4-oxadiazolyl]carbonyl)]-2-(S)-methylpropyl]acetamide; 3-[(Benzyloxycarbonyl)amino]-quinolin-2-one-N-[1-(2-(5-(3-methylbenzyl)-1-,3,4-oxadiazolyl]carbonyl)-2-(S)-methylpropyl]acetamide; 3-[(Benzyloxycarbonyl)amino]-7-piperidinyl-quinolin-2-one-N-[1-(2-(5-(3-methylbenzyl)-1,3,4-oxadiazolyl]carbonyl)-2-(S)-methylpropyl]acetamide; 3-(Carbomethoxy-quinolin-2-one-N-[1-(2-(5-(3-methybenzyl)-1,3,4-oxadiazolyl]carbonyl)-2-(S)-methylpropyl]acetamide; 3-(Amino-quinolin-2-one)-N-[1-(-2-(5-(3-methylbenzyl)-1,3,4-oxadiazolyl]carbonyl)-2-(S)-methylpropyl]acetamide; 3-[(4-Morpholino)aceto]amino-quinolin-2-one-N-[1-(2-(5-(3-methylbenzyl)-1,3,4-oxadiazolyl]carbonyl)-2-(S)-methylpropyl]acetamide; 3,4-Dihydro-quinolin-2-one-N-[1-(2-(5-(3-methylbenzyl)-1,3,4-oxadiazolyl]-carbonyl)-2-(S)-methylpropyl]acetamide; 1-Acetyl-3-(4-fluorobenzylidene)$_p$-piperazine-2,5-dione-N-[1-(2-(5-(3-methylbenzyl)-1,3,4- oxadiazolyl]carbonyl-)-2-(S)-methylpropyl] acetamide; 1-Acetyl-3-(4-dimethylamino benzylidene) piperazine-2,5-dione-N-[1-(2-(5-(3-methylbenzyl)-1,3,4-oxadiazolyl]carbonyl)-2-(S)-methylpropyl]acetamide; 1-Acetyl-3-(4-carbomethoxy benzylidene)piperazine-2,5-dione-N-[1-(2-(5-(3-methylbenzyl)-1,3,4-oxadiazolyl]carbonyl)-2-(S)-methylpropyl]acetamide; 1-Acetyl-3-[(4-pyridyl)methylene]piperazine-2,5-dione-N-[1-(2-(5-(3-methylbenzyl)-1,3,4-oxadiazolyl]carbonyl)-2-(S)-methylpropyl]acetamide; 4-[1-Benzyl-3-(R)-benzyl-piperazine-1-2,5,-dione]-N-[1-(2-[5-(3-methylbenzyl)-1,3,4-oxadiazolyl]carbonyl)-2-methylpropyl]acetamide; 4-[1-Benzyl-3-(S)-benzyl piperazine-2,5,-dione]-N-[1-(2-(5-(3-methylbenzyl)-1,3,4-oxadiazolyl]carbonyl)-2-(S)-methylpropyl]acetamide; 4-[1-Benzyl-3-(R)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Benzyl-3-(S)-benzyl piperazine-2,5,-dione]-N-[1-(3-(5-(2-dimethylaminoethyl)-1,2,4-oxadiazolyl]carbonyl)-2-(S)-methylpropyl]acetamide; 4-[1-Methyl-3-(R,S)-phenylpiperazine-2,5,-dione]-N-[1-(3-(5-(3-trifluoromethylbenzyl)-1,2,4-oxadiazolyl]carbonyl)-2-(S)-methylpropyl]acetamide; 4-[1-Methyl-3-(R,S)-phenyl piperazine-2,5,-dione]-N-[1-(2-(5-(3-methylbenzyl)-1,3,4-oxadiazolyl]carbonyl)-2-(S)-methylpropyl]acetamide; 4-[1-(4-Morpholino ethyl)3-(R)-benzyl piperazine-2,5,-dione]-N-[1-(2-(5-(-3-methylbenzyl)-1,3,4-oxadiazolyl]carbonyl)-2-(S)-methylpropyl]acetamide; 5-(R,S)-Phenyl-2,4-imidazolidinedione-N-[1-(2-(5-(3-methylbenzyl)-1,3,4-oxadiazolyl]carbonyl)-2-(S)-methylpropyl]acetamide; 5-(R)-Benzyl-2,4-imidazolidinedione-N-[1-(2-(5-(3-methylbenzyl)-1,3,4-oxadiazolyl]carbonyl)-2-(S)-methylpropyl]acetamide; 5-(S)-Benzyl-2,4-imidazolidinedione-N-[1-(2-(5-(3- -methylbenzyl)-1,3,4-oxadiazolyl]carbonyl)-2-(S)-methylpropyl]acetamide; 5-(S)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 5-(R)-Benzyl-2,4-imidazolidinedione-N-[1-(3-(5-(3-trifluoromethylbenzyl)-1,2,4-oxadiazolyl]carbonyl)-2-(S)-methylpropyl]acetamide; 1-Benzyl-4-(R)-benzyl-2,5-imidazolidinedione-N-[1-(2-(5-(3-methylbenzyl)-1,3,4-oxadiazolyl]carbonyl)-2-(S)-methylpropyl]acetamide; and 1-Benzyl-4-(R)-benzyl-2,5-imidazolidinedione-N-[1-(3-(5-(3-trifluoromethyl-1 benzyl)-1,2,4-oxadiazolyl]carbonyl)-2-(S)-methylpropyl]acetamide among others.

Likewise, U.S. Pat. No. 5,869,455 discloses N-substituted derivatives; U.S. Pat. No. 5,861,380 protease inhibitors-keto and di-keto containing ring systems; U.S. Pat. No. 5,807,829 serine protease inhibitor-tripeptoid analogues; U.S. Pat. No. 5,801,148 serine protease inhibitors-proline analogues; U.S. Pat. No. 5,618,792 substituted heterocyclic compounds useful as inhibitors of serine proteases. These patents and PCT publications and others as listed infra are incorporated herein, in their entirety, by reference. Other equally advantageous molecules, which may be used instead of α1-antitrypsin or in combination with α1-antitrypsin are contemplated such as in WO 98/20034 disclosing serine protease inhibitors from fleas. Without limiting to this single reference one skilled in the art can easily and without undue experimentation adopt compounds such as in WO98/23565 which discloses aminoguanidine and alkoxyguanidine compounds useful for inhibiting serine proteases; WO98/50342 discloses bis-aminomethylcarbonyl compounds useful for treating cysteine and serine protease disorders; WO98/50420 cyclic and other amino acid derivatives useful for thrombin-related diseases; WO 97/21690 D-amino acid containing derivatives; WO 97/10231 ketomethylene group-containing inhibitors of serine and cysteine proteases; WO 97/03679 phosphorous containing inhibitors of serine and cysteine proteases; WO 98/21186 benzothiazo and related heterocyclic inhibitors of serine proteases; WO 98/22619 discloses a combination of inhibitors binding to P site of serine proteases with chelating site of divalent cations; WO 98/22098 a composition which inhibits conversion of pro-enzyme CPP32 subfamily including caspase 3 (CPP32/Yama/Apopain); WO 97/48706 pyrrolo-pyrazine-diones; WO 97/33996 human placental bikunin (recombinant) as serine protease inhibitor; WO 98/46597 complex amino acid containing molecule for treating viral infections and conditions disclosed hereinabove.

Other compounds having serine protease inhibitory activity are equally suitable and effective for use in the methods of the present invention, including but not limited to: tetrazole derivatives as disclosed in WO 97/24339; guanidinobenzoic acid derivatives as disclosed in WO 97/37969 and in a number of U.S. Pat. Nos. 4,283,418; 4,843,094; 4,310,533; 4,283,418; 4,224,342; 4,021,472; 5,376,655; 5,247,084; and 5,077,428; phenylsulfonylamide derivatives represented by general formula in WO 97/45402; novel sulfide, sulfoxide and sulfone derivatives represented by general formula in WO 97/49679; novel amidino derivatives represented by general formula in WO 99/41231; other amidino-phenol derivatives as disclosed in U.S. Pat. Nos. 5,432,178;

5,622,984; 5,614,555; 5,514,713; 5,110,602; 5,004,612; and 4,889,723 among many others.

Mycobacterial Diseases Addressed by the Invention

Specific mycobacterial diseases or disorders for which the therapeutic methods of inhibiting the mycobacterial infection of macrophages of the invention are beneficial include, but are not limited to, those mycobacterial diseases or disorders caused by mycobacteria from the genus *mycobacterium* that includes *M. tuberculosis, M. bovis, M. leprae, M. avium-intracellulare, M. chelonei* (also known as borstelense and abscessus), *M. africanum, M. marinium* (also known as balnei and platypoecilus), *M. buruli* (also known as ulcerans), *M. fortuitum* (also known as giae, minetti, and ranae), *M. haemophilum, M. intracellulare, M. kansasii* (also known as luciflavum), *M. littorale* (also known as xenopi), *M. malmoense, M. marianum* (also known as scrofulaceum and paraffinicum), *M. simiae, M. szulgai, M. ulcerans, M. avium* (also known as brunense), *M. flavascens, M. lepraemurium, M. microti*, and *M. paratuberculosis* (which is the causative agent for Johne's Disease, and a possible cause of Crohn's disease), *M. gordonae* (also known as aquae), *M. gastri, M. phlei* (also known as moelleri and as timothy *bacillus*), *M. nonchromogenicum, M. smegmatis, M. terrae, M. triviale*, and *M. vaccae*.

In another embodiment, the *mycobacterium* inhibited from infecting macrophages comprises a *mycobacterium* from the genus *mycobacterium* that includes non-tuberculosis mycobacteria that are divided into four groups comprising Runyon groups, selected from the group consisting of Group I (slow-growing photochromogens), Group II (slow-growing scotochromogens), Group III (slow-growing nonphotochromogens), and Group IV (rapidly-growing mycobacteria).

Bacillus Anthracis and Anthrax Toxin

Anthrax toxin, produced by the gram positive rod-shaped aerobic, spore-forming bacterium *Bacillus anthracis*, is the toxic virulence factor secreted by this organism. *B. anthraxis* is often considered for use as a biological weapon due to the potency of the secreted exotoxin, and to the capacity of the bacterium to form dormant spores which resist harsh environmental conditions. Sporulation enables ready transport and distribution of large quantities of toxin-producing bacteria. The toxin is actually a composite consisting of 3 separate secreted proteins from the bacterium. The 3 proteins are protective antigen (PA), lethal factor (LF), and edema factor (EF). While LF and EF directly damage cells and are thought to cause disease due to anthrax toxin exposure, the PA is the focus of this present disclosure. PA is crucial to the virulence of anthrax toxin, since the PA molecule is designed to import both LF and EF inside the membranes of cells. In the absence of PA-induced intracellular transport, anthrax toxin is unable to effect tissue destruction, since LF and EF only function from within the cell. The importance of PA in the function of anthrax toxin is underscored by the effective use of PA as the immunogen in anthrax vaccine. By generating an immune response against PA, the vaccine confers protection against full (3 component) anthrax toxin.

A closer examination of the interaction between PA and the host cells attacked by anthrax toxin is instructive. PA is first secreted by *B. anthracis* in a large and functionally inactive form. This inactive PA binds to a receptor on the surface of host cells. The PA receptor has recently been isolated and sequenced, and found to possess von Willebrand Factor-like regions. After docking on the surface of host cells, PA interacts with a protease present on the cell surface. The protease cuts (processes) the large and inactive PA molecule into a smaller and active remnant. The identity of this protease has been the focus of scant research effort, and it is poorly characterized. However, prior studies have shown that the protease has characteristics that suggest it is a host-derived serine protease. A possible serine protease candidate noted in the literature is furin (itself a serine protease), but other serine proteases, such as elastase, proteinase-3, or trypsin are possible alternatives. Once processed by the action of the cell-surface serine proteas(s), the activated PA molecules self-assemble into groups of 7 (heptamers) on the cell surface. These heptames function as the transport vehicle to deliver LF and EF inside of the cell. Once inside the cell, LF and EF initiate abnormalities in cell function.

A novel approach to nullify the action of anthrax toxin is to block access of the toxin to the interior of the cell. The present inventor has shown, in previous extensive laboratory studies (Leland Shapiro et al. Facet 2000 vol. 15: 115-122, and unpublished data of Dr. Leland Shapiro), that serine proteases residing on the cell surface can be neutralized by the action of several types of molecules which inhibit serine protease function. The most important natural, endogenous inhibitor of serine proteases is α-1-antitrypsin (AAT). It is noteworthy that AAT levels are reduced in lymphatics, and that anthrax toxin production and disease manifestations originate from within the lymphatics. It is possible that toxin production occurs in lymphatic tissues because the reduced amounts of AAT provide a microenvironment conducive to enhanced serine protease function. Such conditions are expected to augment production of activated anthrax toxin. Therefore, administering to the subject a pharmaceutically effective amount of a substance exhibiting mammalian α1-antitrypsin or inhibitor of serine protease activity serves to attenuate or abolish the activity of anthrax toxin by blocking the activity of the host-derived serine protease that resides on the cell surface. This will negate the cell-surface processing of inactive large PA into the active smaller PA remnant. Thus, by interfering with the host-derived serine protease's activity, this will disrupt the ability of heptameric PA63 to form the prepore and ultimately the pore. By disarming the anthrax toxin using this novel approach (See FIGS. 4A-4H) several advantages are obtained compared to alternative approaches, for example, and not by way of limitation:

1. Serine protease inhibition, as a strategy to treat anthrax infection, is highly likely to be impervious to bacterial mutation due to selective pressure. By choosing to target or inhibit the serine proteases of host cell origin, the target molecule is immutable.

2. Synthetic inhibitors of serine proteases (AAT-like mimics) can and have been developed (See, infra, CE-2072). Such a pharmaceutical agent may be formulated into a pill for oral consumption in the field or formulated as an inhaler to treat inhalation anthrax.

3. Commercially available agents already approved for alternate use in humans will work as a treatment for anthrax. These agents are currently used for indications other than anthrax toxicity, and include injectable AAT, plasma preparations, aprotinin and others (American J. Of Resp Critical Care Med 1998, VII 158: 49-59). One possible instantiation of this invention may be of immediate practical application Inhibitors of serine proteases have been delivered to patients by inhalation. Since the most lethal form of anthrax infection is pulmonary invasion, an inhaled agent (natural AAT or a synthetic AAT-like mimic/or other inhibitor of serine protease) may be especially useful due to elevated local concentrations, ease of drug delivery, and lack of side effects (since administration is not systemic). This mode of focused drug delivery may augment serine protease inhibitor activity within the pulmonary and mediastinal lymphatics, which are the principle sites where anthrax is thought to initiate fulminant disease.

4. By neutralizing the anthrax toxin, the direct cause of disease is disrupted in infected individuals. Antibiotics, on the other hand, do not target toxin activity, and cannot affect toxin produced prior to destruction of the bacteria. This invention specifically contemplates inhibiting host cell serine proteases in conjunction with administration of one or more anti-bacterial antibiotics. Antibiotics will stop further toxin production by preventing the growth of bacteria and/or killing the bacterial source of toxin.

5. This approach to anthrax therapy is likely to be safe. There is an extensive clinical experience using injectable AAT to treat patients with genetic AAT deficiency. No long-term untoward effects have been detected to date (American J. Of Resp Critical Care Med 1998, VII 158: 49-59; Wencker et al. Chest 2001 119:737-744). Moreover, a small molecule inhibitor of host serine protease has been administered to patients with Kawasaki's Disease (Ulinistatin, Ono pharmaceuticals), with an excellent safety and tolerability record. In addition, inhibition of host serine proteases to treat anthrax infection will only require a short treatment course, thus minimizing any potential concerns with long term exposure to AAT or AAT-like mimics/or other inhibitors of serine protease.

6. Soluble anthrax receptors (Bradley et al. Nature 2001 vol. 414), bacteriophage lysis of anthrax organisms (Schuch et al. Nature 2002 vol. 418 884-889), dominant negative mutant anthrax toxin components (Sellman er al. Science 2001 VI. 292: 695-697) and polyvalent inhibitors (Mourez et al Nature Biotech 2001 Vol. 19,:958-961) may also be used in conjunction with the anthrax-based methods of the present invention.

Thus, in view of the above, the present invention provides methods for preventing a symptom of anthrax in a subject suspected of having been exposed to or thought to be at risk for exposure to *Bacillus anthracis* comprising administering to the subject a pharmaceutically effective amount of a substance exhibiting mammalian α1-antitrypsin or inhibitor of serine protease activity. The present invention also provides a method for ameliorating a symptom of anthrax in a subject in need of said amelioration comprising administering to the subject a pharmaceutically effective amount of a substance exhibiting mammalian α1-antitrypsin or inhibitor of serine protease activity.

In each of the above-recited methods, the clinical symptoms of anthrax can be inhibited or prevented by administration of a substance exhibiting mammalian α1-antitrypsin or inhibitor of serine protease activity.

Clinical Symptoms of Anthrax

Anthrax occurs as three general clinical entities: i) inhalation, ii) cutaneous, and iii) gastrointestinal forms.

i) Inhalation anthrax is the deadliest form of the disease, and it is the one most likely to be involved in a bioweapons altercation or accident. Usually, an infected person inhales anthrax spores serendipitously, or during a bioweapons attack. Following a 1-6 day incubation period, a biphasic illness ensues. Initially, there is non-specific malaise/fever/dry cough/myalgias, and chest pains. The second phase occurs 2-3 days after the first phase, and consists of progression of the constitutional non-specific findings listed above, an addition to ventilatory compromise, sweating, widening of the mediastimum on radiographic studies, and edema of the neck and chest. This stage of illness is characterized by a necrotizing mediastinal lymphadenitis. This second stage of disease can rapidly progress to shock and death within 2 days, and mortality rates of up to 80% have been reported. The mechanism of death in animal models appears to be enhanced production of pro-inflammatory cytokines, especially IL-1. It is of note, referable to the instant invention disclosure, that lymph tissue is deficient in serine protease inhibitor activity compared to other body tissues. The implication is that anthrax toxin is selectively activated in regions of the body (lymphatics) where there is an imbalance in serine protease/anti-serine protease function that favors serine protease activity. A preferred embodiment for using the instant invention to treat inhalation anthrax is to deliver large amounts of a serine protease inhibitor (natural or synthetic) by inhalation. This will result in a shift in the serine protease/serine protease inhibitor balance in pulmonary and mediastinal lymphatic tissues toward antiprotease activity. This will result in blockade of the cell-surface processing event that is required for activity of anthrax toxin.

ii) Cutaneous anthrax is the commonest form (>95%) of anthrax infection in humans.

Upon exposure to anthrax spores, regions of denuded skin (cuts, abrasions, etc.), present an environment that enables anthrax organisms to emerge from the spore state, to grow and replicate, and produce anthrax toxin. Within 1 week, the area of anthrax inoculation develops a painless papule. Vesicles then form on or near the papule over the ensuing 1-2 days, followed shortly by development of fever and malaise, and a non-pitting edema surrounding the skin lesion that is due to toxin activity. The original lesion (often now a vesicle) ruptures to form necrotic ulceration and enlargement—this results in formation of the eschar that characterizes cutaneous anthrax infection. In the absence of therapy, this disease carries a 20% morality. For those who recover, the eschar sloughs off in 1-2 weeks. A preferred embodiment of the instant invention for the treatment of cutaneous anthrax is to administer a serine protease inhibitor (natural or synthetic) in a topical/cream preparation. Parenteral serine protease inhibitor therapy can also be co-administered in the event that systemic symptoms emerge, or such parenteral therapy can be administered prophylactically for anthrax that appears clinically to be localized to the skin.

iii) Gastrointestinal anthrax appears after ingestion of anthrax spores. After 2-5 days, one develops nausea/vomiting/fever, and abdominal pain. Bloody diarrhea rapidly ensues, and an "acute abdomen" manifests. The pathology within the abdomen includes mucosal ulcerations. Also, hemorrhagic mesenteric lymphadenitis develops, and this is again consistent with selective activation of the anthrax toxin in serine protease-inhibitor deficient microenvironments. This disease carries a mortality rate of 50%.

Isolated Proteins for Use in the Compositions and Methods of the Invention

One aspect of the invention pertains to isolated proteins, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

Recombinant unmodified and mutant variants of α.sub.1-antitrypsin produced by genetic engineering methods are also known (U.S. Pat. No. 4,711,848). The nucleotide sequence of human α1-antitrypsin and other human α1-antitrypsin variants has been disclosed in international published application No. WO 86/00,337, the entire contents of which are incorporated herein by reference. This nucleotide sequence may be used as starting material to generate all of the AAT amino acid variants and amino acid fragments depicted herein, using recombinant DNA techniques and methods known to those of skill in the art.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence shown in any of SEQ ID NOS: 1, 2, 3, 4, 5, 6, 7; 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60. Other useful proteins are substantially identical (e.g., at least about 45%, preferably 55%, 65%, 75%, 85%, 95%, or 99%) to any of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions).times.100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the CGC sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. For a further description of FASTA parameters, see http://bioweb.pasteur.fr/docs/Man/man/fasta.1.html#sect2, the contents of which are incorporated herein by reference.

The percent identity between two sequences can be determined using techniques similar to those described above, with or without allowing gaps. In calculating percent identity, only exact matches are counted.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phase display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu Rev. Biochem. 53:323; Itakura et al. (1984) Science 198: 1056; Ike et al. (1983) Nucleic Acid Res. 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with 51 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60, and encompasses an epitope of the protein such that an antibody raised against the peptide forms a specific immune complex with the protein.

Fusion Proteins for Use in the Compositions and Methods of the Invention

In each of the aforementioned aspects and embodiments of the invention, fusion polypeptides are also specifically contemplated herein.

In one embodiment, fusion polypeptides of the invention are produced by recombinant DNA techniques. Alternative to recombinant expression, a fusion polypeptide of the invention can be synthesized chemically using standard peptide synthesis techniques. The present invention also provides compositions that comprise a fusion polypeptide of the invention and a pharmaceutically acceptable carrier, excipient or diluent.

In each of the above-recited methods, the mammalian α1-antitrypsin or inhibitor of serine protease activity substance may be part of a fusion polypeptide, wherein said fusion polypeptide comprises mammalian α1-antitrypsin or inhibitor of serine protease activity substance and an amino acid sequence heterologous to said mammalian α1-antitrypsin or inhibitor of serine protease activity substance.

Among the particular fusion polypeptides of the invention are, for example, fusion polyeptides that comprise the amino acid sequence of the α1-antitrypsin depicted below in SEQ ID NO:63.

```
  1          01         01         01         01        0
MPSSVSWGIL LAGLCCLVPV SLAEDPQGDA AQKTDTSHHD QDHPTFNKIT

PNLAEFAFSL YRQLAHQSNS TNIFFSPVSI ATAFAMLSLG TKADTHDEIL 100

EGLNFNLTEI PEAQJHEGFQ ELLRTLNQPD SQLQLTTGNG LFLSEGLKLV

DKFLEDVKKL YHSEAFTVNF GDHEEAKKQI NDYVEKGTQG KIVDLVKELD 200
```

-continued

```
RDTVFALVNY IFFKGKWERP FEVKDTEDED FHVDQVTTVK VPMMKRLGMF

NIQHCKKLSS WVLLMKYLGN ATALFFLPDE GKLQHLENEL THDIITKYLE    300

NEDRRSASLH LPKLSITGTY DLKSVLGQLG ITKVFSNGAD LSGVTEEAPL

KLSKAVHKAV LTIDEKGTEA AGAMFLEAIP MSIPPEVKFN KPFVFLMIEQ    400

NTKSPLFMGK VVNPTQK                                       417
```

The fusion polypeptides of the invention can be such that the heterologous amino acid sequence comprises a human immunoglobulin constant region, such as a human IgG1 constant region, including a modified human IgG1 constant region wherein the IgG1 constant region does not bind Fc receptor and/or does not initiate antibody-dependent cellular cytotoxicity (ADCC) reactions.

In particular, in one embodiment the fusion protein comprises a heterologous sequence that is a sequence derived from a member of the immunoglobulin protein family, for example, comprise an immunoglobulin constant region, e.g., a human immunoglobulin constant region such as a human IgG1 constant region. The fusion protein can, for example, comprise a portion of a mammalian α1-antitrypsin or inhibitor of serine protease activity polypeptide fused with the amino-terminus or the carboxyl-terminus of an immunoglobulin constant region, as disclosed, e.g., in U.S. Pat. No. 5,714,147, U.S. Pat. No. 5,116,964, U.S. Pat. No. 5,514,582, and U.S. Pat. No. 5,455,165. In those embodiments in which all or part of a polypeptide of the invention is fused with sequences derived from a member of the immunoglobulin protein family, the FcR region of the immunoglobulin may be either wild-type or mutated. In certain embodiments, it is desirable to utilize an immunoglobulin fusion protein that does not interact with a Fc receptor and does not initiate ADCC reactions. In such instances, the immunoglobulin heterologous sequence of the fusion protein can be mutated to inhibit such reactions. See, e.g., U.S. Pat. No. 5,985,279 and WO 98/06248.

The heterologous amino acid sequence of the fusion polypeptides utilized as part of the present invention can also comprise an amino acid sequence useful for identifying, tracking or purifying the fusion polypeptide, e.g., can comprise a FLAG or a His tag sequence. The fusion polypeptide can further comprise an amino acid sequence containing a proteolytic cleavage site which can, for example, be useful for removing the heterologous amino acid sequence from the α1-antitrypsin or inhibitor of serine protease derivative or mimic sequence of the fusion polypeptide.

In particular, the heterologous amino acid sequence of the fusion polypeptides of the present invention can also comprise an amino acid sequence useful for identifying, tracking or purifying the fusion polypeptide, e.g., can comprise a FLAG (see, e.g., Hoop, T. P. et al., Bio/Technology 6, 1204-1210 (1988); Prickett, K. S. et al., BioTechniques 7, 580-589 (1989)) or a His tag (Van Reeth, T. et al., BioTechniques 25, 898-904 (1998)) sequence. The fusion polypeptide can further comprise an amino acid sequence containing a proteolytic cleavage site which can, for example, be useful for removing the heterologous amino acid sequence from the mammalian α1-antitrypsin or inhibitor of serine protease activity polypeptide sequence of the fusion polypeptide.

In yet another embodiment, the mammalian α1-antitrypsin or inhibitor of serine protease-like activity polypeptide fusion protein comprises a GST fusion protein in which the mammalian α1-antitrypsin or inhibitor of serine protease activity polypeptide of the invention is fused to the C-terminus of GST sequences. Such a fusion protein can facilitate the purification of a recombinant polypeptide of the invention. In those embodiments in which a GST, FLAG or HisTag fusion constructs is employed in the construction of the mammalian α1-antitrypsin or inhibitor of serine protease activity polypeptide fusion proteins, proteolytic cleavage sites may be optionally introduced at the junction of the fusion moiety and the mammalian α1-antitrypsin or inhibitor of serine protease activity polypeptide to enable separation of the mammalian α1-antitrypsin or inhibitor of serine protease activity polypeptide from the fusion moiety subsequent to purification of the mammalian α1-antitrypsin or inhibitor of serine protease activity polypeptide. Such enzymes, and their cognate recognition sequences, include, for example, without limitation, Factor Xa, thrombin and enterokinase. Typical fusion expression vectors include pGEX (Pharmacia Biotech Inc.; Smith and Johnson (1988) Gene 67:31-40), pMAL (New England Biolabs, Beverly, Mass.) and pRIT5 (Pharmacia, Piscataway, N.J.) which may be used to fuse glutathione S-transferase (GST), maltose E binding protein, or protein A, respectively, to the target mammalian α1-antitrypsin or inhibitor of serine protease activity polypeptide protein.

Expression vectors can routinely be designed for expression of a fusion polypeptide of the invention in prokaryotic (e.g., E. coli) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion E. coli expression vectors include pTrc (Amann et al., (1988) Gene 69:301-315) and pET lid (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET lid vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in E. coli is to express the protein in a host bacterium with an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerivisae include pYepSec1 (Baldari et al. (1987) EMBO J. 6:229-234), pMFa (Kurjan and Herskowitz, (1982) Cell 30:933-943), PJRY88 (Schultz et al. (1987) Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell. Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the alpha-fetoprotein promoter (Campes and Tilghman (1989) Genes Dev. 3:537-546).

A host cell can be any prokaryotic (e.g., E. coli) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

Combination Therapies for Treating Mycobacterial Diseases and Anthrax Using the Methods of the Invention In each of the aforementioned aspects and embodiments of the invention, combination therapies other than those enumerated above are also specifically contemplated herein. In particular, the compositions of the present invention may be administered with one or more macrolide or non-macrolide antibiotics, anti-bacterial agents, anti-fungicides, anti-viral agents, and anti-parasitic agents, anti-inflammatory or immunomodulatory drugs or agents.

Examples of macrolide antibiotics that may be used in combination with the composition of the present invention include, inter alia, the following synthetic, semi-synthetic or naturally occurring microlidic antibiotic compounds: methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the derivatives of these compounds. Thus, erythromycin and compounds derived from erythromycin belong to the general class of antibiotics known as "macrolides." Examples of preferred erythromycin and erythromycin-like compounds include: erythromycin, clarithromycin, azithromycin, and troleandomycin.

Additional antibiotics, other than the macrolidic antibiotics described above, which are suitable for use in the methods of the present invention include, for example, any molecule that tends to prevent, inhibit or destroy life and as such, and as used herein, includes anti-bacterial agents, anti-fungicides, anti-viral agents, and anti-parasitic agents. These agents may be isolated from an organism that produces the agent or procured from a commercial source (e.g., pharmaceutical company, such as Eli Lilly, Indianapolis, Ind.; Sigma, St. Louis, Mo.).

For example, the anti-TB antibiotic isoniazid (isonicotinic acid hydrazide) is frequently effective, but isoniazid often causes severe, sometimes fatal, hepatitis. The risk of hepatitis increases with the patient's age. Additionally, isoniazid causes peripheral neuropathy in some recipients in a dose-related fashion. Rifampin, another antibiotic used to treat TB, must be used in conjunction with another drug such as isoniazid. This requirement for combination therapy with rifampin applies to the initial treatment as well as the retreatment of pulmonary TB.

Usually, isoniazid, rifampin, ethambutol and ethionamide are given orally. Streptomycin is typically given intramuscularly. Amikacin is given intramuscularly or intravenously. Clofazimine, which is also used to treat leprosy, is given orally.

Amikacin is a semisynthetic aminoglycoside antibiotic derived from Kanamycin A. For its preparation see U.S. Pat. No. 3,781,268. For a review see Kerridge, Pharmacological and Biochemical Properties of Drug Substances 1:125-153, M. E. Goldberg, ed. (1977). Amikacin is usually administered intramuscularly or intravenously. For additional information including clinical pharmacology, indications, side effects and dosages, see the Physicians Desk Reference, 42 ed. (1988) at pages 744-746 (hereinafter, PDR).

Clofazimine is an antibacterial agent also known as LAMPRENE® For its preparation, see Barry, et al., Nature 179:1013 (1957). For a review see Karat, et al., Brit. Med. J. 3:175 (1971). Clofazimine is generally given orally. For additional information including clinical pharmacology, precautions and dosages, see the PDR at page 982.

Ethionamide is an antibacterial agent also known as AMIDAZINE® and TRECATOR® See British Patent No. 800,250. This drug is typically given orally. For further information including precautions and dosages, see the PDR at page 2310.

Ciprofloxacin is a broad spectrum synthetic antibacterial agent for oral usage. It is also known as CIPRO® It is typically given in total daily dosages of 500 to 1,000 milligrams which is usually given in 2 equal doses in 24 hours. For further information see the PDR (1989) at pages 1441-1443. other member of this fluoroquinolone class of antibiotics include ofloxacin, levofloxacin, troveofloxacin, pefloxacin, gatifloxacin, and moxifloxacin.

Other examples of anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, oxazalidinones, and fluoroquinolones. Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefmetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Anti-fungal agents include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents include, but are not limited to, valganciclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

In another aspect, in the method of the present invention, one may, for example, supplement the composition by administration of a therapeutically effective amount of one or more an anti-inflammatory or immunomodulatory drugs or agents. By "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or antigen presenting cells (APC), or by acting upon components outside the immune system which, in turn, stimulate, suppress, or modulate the immune system, e.g., hormones, receptor agonists or antagonists, and neurotransmitters; immunomodulators can be, e.g., immunosuppressants or immunostimulants. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, e.g., betaseron, .beta.-interferon; prostane derivatives, e.g., compounds disclosed in PCT/DE93/0013, e.g., iloprost, cicaprost; glucocorticoid, e.g., cortisol, prednisolone, methylprednisolone, dexamethasone; immunsuppressives, e.g., cyclosporine A, FK-506, methoxsalene, thalidomide, sulfasalazine, azathioprine, methotrexate; lipoxygenase inhibitors, e.g., zileutone, MK-886, WY-50295, SC-45662, SC-41661A, BI-L-357; leukotriene antagonists, e.g., compounds disclosed in DE 40091171 German patent application P 42 42 390.2; WO 9201675; SC-41930; SC-50605; SC-51146; LY 255283 (D. K. Herron et al., FASEB J. 2: Abstr. 4729, 1988); LY 223982 (D. M. Gapinski et al. J. Med. Chem. 33: 2798-2813, 1990); U-75302 and analogs, e.g., described by J. Morris et al., Tetrahedron Lett. 29: 143-146, 1988, C. E. Burgos et al., Tetrahedron Lett. 30: 5081-5084, 1989; B. M. Taylor et al., Prostaglandins 42: 211-224, 1991; compounds disclosed in U.S. Pat. No. 5,019,573; ONO-LB-457 and analogs, e.g., described by K. Kishikawa et al., Adv. Prostagl. Thombox. Leukotriene Res. 21: 407-410, 1990; M. Konno et al., Adv. Prostagl. Thrombox. Leukotriene Res. 21: 411-414, 1990; WF-11605 and analogs, e.g., disclosed in U.S. Pat. No. 4,963,583; compounds disclosed in WO 9118601, WO 9118879; WO 9118880, WO 9118883, antiinflammatory substances, e.g., NPC 16570, NPC 17923 described by L. Noronha-Blab. et al., Gastroenterology 102 (Suppl.): A 672, 1992; NPC 15669 and analogs described by R. M. Burch et al., Proc. Nat. Acad. Sci. USA 88: 355-359, 1991; S. Pou et al., Biochem. Pharmacol. 45: 2123-2127, 1993; peptide derivatives, e.g., ACTH and analogs; soluble TNF-receptors; TNF-antibodies; soluble receptors of interleukines, other cytokines, T-cell-proteins; antibodies against receptors of interleukins, other cytokines, and T-cell-proteins.

The therapeutic agents of the instant invention may be used for the treatment of animal subjects or patients, and more preferably, mammals, including humans, as well as mammals such as non-human primates, dogs, cats, horses, cows, pigs, guinea pigs, and rodents.

Modes of Administration

Modes of administration of the various therapeutic agents used in the invention are exemplified below. However, the agents can be delivered by any of a variety of routes including: by injection (e.g., subcutaneous, intramuscular, intravenous, intraarterial, intraperitoneal), by continuous intravenous infusion, cutaenously, dermally, transdermally, orally (e.g., tablet, pill, liquid medicine), by implanted osmotic pumps (e.g., Alza Corp.), by suppository or aerosol spray.

The peptide-based serine protease inhibitors may be prepared by any suitable synthesis method such as originally described by Merrifield, J. Am. Chem. Soc., 85, p 2149 (1963). Synthetic peptides which exhibit inhibitory activity toward serine proteases and methods for preparing and using same are disclosed for example in U.S. Pat. Nos. 4,829,052, 5,157,019 to Glover; U.S. Pat. No. 5,420,110 to Miller; U.S. Pat. No. 4,963,654 Katunuma as incorporated herein by reference.

Those skilled in the art of biochemical synthesis will recognize that for commercial-scale quantities of peptides, such peptides are preferably prepared using recombinant DNA techniques, synthetic techniques, or chemical derivatization of biologically or chemically synthesized peptides.

The compounds of the present invention are used as therapeutic agents in the treatment of a physiological (especially pathological) condition caused in whole or part, by excessive serine protease activity. The peptides may be administered as free peptides or pharmaceutically acceptable salts thereof. The terms used herein conform to those found in Budavari, Susan (Editor), "The Merck Index" An Encyclopedia of Chemicals, Drugs, and Biologicals; Merck & Co., Inc. The term "pharmaceutically acceptable salt" refers to those acid addition salts or metal complexes of the peptides which do not significantly or adversely affect the therapeutic properties (e.g. efficacy, toxicity, etc.) of the peptides. The peptides should be administered to individuals as a pharmaceutical composition, which, in most cases, will comprise the peptide and/or pharmaceutical salts thereof with a pharmaceutically acceptable carrier. The term "pharmaceutically acceptable carrier" refers to those solid and liquid carriers, which do not significantly or adversely affect the therapeutic properties of the peptides.

The pharmaceutical compositions containing peptides of the present invention may be administered to individuals, particularly humans, either intravenously, subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally and direct injection into an airway, such as through a tracheotomy, tracheostomy, endotracheal tube, or metered dose or continuous inhaler. In addition, osmotic pumps may be used for administration. The necessary dosage will vary with the particular condition being treated, method of administration and rate of clearance of the molecule from the body.

Although the compounds described herein and/or their derivatives may be administered as the pure chemicals, it is preferable to present the active ingredient as a pharmaceutical composition. The invention thus further provides the use of a pharmaceutical composition comprising one or more compounds and/or a pharmaceutically acceptable salt thereof, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

Pharmaceutical compositions include those suitable for oral or parenteral (including intramuscular, subcutaneous, cutaneous, inhaled and intravenous) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical compositions suitable for oral administration may be presented as discrete unit dosage forms such as hard or soft gelatin capsules, cachets or tablets, each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., e.g., with enteric coatings.

Oral liquid preparations may be in the form of, for example, aqueous or oily suspension, solutions, emulsions, syrups or elixirs, or may be presented as a dry product for constitution with water or another suitable vehicle before use. Such liquid preparations may contain conventional additives such as suspending agents, emulsifying agents, non-aqueous vehicles (which may include edible oils), or preservative. The compounds may also be formulated for parenteral administration (e.g., by injection, for example, bolus injection or continuous infusion) and may be presented in unit dose form in ampoules, pre-filled syringes, small bolus infusion containers or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be selected, ultimately, at the discretion of the attending physician.

A pharmaceutical composition of the invention contains an appropriate pharmaceutically acceptable carrier as defined supra. These compositions can take the form of solutions, suspensions, tablets, pills, capsules, powders, sustained-release formulations and the like. Suitable pharmaceutical carriers are described in Remington's Pharmaceutical Sciences 1990, pp. 1519-1675, Gennaro, A. R., ed., Mack Publishing Company, Easton, Pa. The serine protease inhibitor molecules of the invention can be administered in liposomes or polymers (see, Langer, R. Nature 1998, 392, 5). Such compositions will contain an effective therapeutic amount of the active compound together with a suitable amount of carrier so as to provide the form for proper administration to the subject.

In general, the compound is conveniently administered in unit dosage form; for example, containing 5 to 2000 mg, conveniently 10 to 1000 mg, most conveniently, 50 to 500 mg of active ingredient per unit dosage form.

Desirable blood levels may be maintained by continuous infusion to provide about 0.01-5.0 mg/kg/hr or by intermittent infusions containing about 0.4-20 mg/kg of the active ingredient(s). Buffers, preservatives, antioxidants and the like can be incorporated as required.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular pharmaceutical compound or analogue thereof of the present invention, the route of administration, the severity of the condition being treated, and the condition and prior medical history of the patient being treated. However, it is within the skill of the art to start doses of the pharmaceutical compound at levels lower than required to achieve the desired therapeutic effect and to gradually increase the dosage until the desired effect is achieved.

The pharmaceutical compositions of the present invention can be used in both veterinary medicine and human therapy. The magnitude of a prophylactic or therapeutic dose of the pharmaceutical composition of the invention in the acute or chronic management of pain associated with above-mentioned diseases or indications will vary with the severity of the condition to be treated and the route of administration. The dose, and perhaps the dose frequency, will also vary according to the age, body weight, and response of the individual patient. In general, the total daily dose range of the pharmaceutical composition of this invention is generally between about 1 to about 100 mg, preferably about 1 to about 20 mg, and more preferably about 1 to about 10 mg of active compound per kilogram of body weight per day are administered to a mammalian patient. If desired, the effective daily dose may be divided into multiple doses for purposes of administration, e.g. two to four separate doses per day.

Alternatively, the total daily dose range of the active ingredient of this invention should be sufficient to increase the serum concentration of the proease inhibitor by 10-100 micromolar.

It is intended herein that by recitation of such specified ranges, the ranges cited also include all those dose range amounts between the recited range. For example, in the range about 1 and 100, it is intended to encompass 2 to 99, 3-98, etc, without actually reciting each specific range. The actual preferred amounts of the active ingredient will vary with each case, according to the species of mammal, the nature and severity of the particular affliction being treated, and the method of administration.

It is also understood that doses within those ranges, but not explicitly stated, such as 30 mg, 50 mg, 75 mg, etc. are encompassed by the stated ranges, as are amounts slightly outside the stated range limits.

The actual preferred amounts of the active ingredient will vary with each case, according to the species of mammal, the nature and severity of the particular affliction being treated, and the method of administration.

In general, the pharmaceutical compositions of the present invention are periodically administered to an individual patient as necessary to improve symptoms of the particular disease being treated. The length of time during which the compositions are administered and the total dosage will necessarily vary with each case, according to the nature and severity of the particular affliction being treated and the physical condition of the subject or patient receiving such treatment.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know, with no more than routine experimentation, how and when to interrupt, adjust, or terminate therapy in conjunction with individual patient response.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

EXAMPLES

The following specific examples are provided to better assist the reader in the various aspects of practicing the present invention. As these specific examples are merely illustrative, nothing in the following descriptions should be construed as limiting the invention in any way. Such limitations are, or course, defined solely by the accompanying claims.

Example One

Effect of α1-Antitrypsin on *Mycobacterium Avium* Complex (Mac) Infection of Human Monocyte-Derived Macrophages 1. TB or MAC organisms were suspended at a concentration of one Mcfarland standard. One McFarland is defined as a degree of turbidity of organisms suspended in liquid that matches that of a standard aliquot. A sample turbidity that is equivalent to that of the one McFarland standard represents about $10^7$ bacilli/ml. The optimal duration of a test culture is approximately 10-12 days of bacilli grown in Middlebrook 7H9 broth (=*mycobacterium* medium).

2. Infecting the cells. The cells infected were human monocyte-derived macrophages (MDM). MDM were isolated from human peripheral blood mononuclear cells (PBMC) that were obtained from heparinized blood from healthy volunteers by centrifuging the heparinized blood over a ficol-hypaque cushion. The isolated PBMC were aliquoted into polystyrene tissue culture plates and the monocytes are allowed to adhere ×2 hrs ($0.5 \times 10^6$ PBMC were added to each well, of which approximately 10-20% are monocytes). Experiments were performed in plates without or with sterile round glass coverslips in the bottoms of the wells (see a. below). Only the monocytic population within the PBMC will adhere to the plates under these conditions. The wells were then washed (to remove the non-adhering lymphocytes) and incubated in fresh medium ×10-12 days (medium=RPMI+10% fetal calf serum+100 units/ml of penicillin G), which allows maturation of the monocytes into macrophages. The volume of medium in each well was 1.0 ml. The medium was then removed from each well of MDM, and the wells were replenished with either medium alone (control), with AAT, or with ala-ala-pro-val-chloromethyl ketone (an AAT-like synthetic serine protease inhibitor)(Bachem, Inc.), and the wells were incubated for 3.0 hr. Then, the MDM in each well were infected with MAC (strain *Mycobacterium avium* 9141) or TB (strain H37RV) at a ratio of mycobacterial bacilli/cell of $1 \times 10^6$. After a 1.0 hr incubation (to allow the mycobacteria to bind to the MDM surfaces), the supenatants were removed and saved for cytokine assays. The wells were then washed twice (with a 1:1 solution of RPMI and saline), Two independent assays were then used to quantify mycobacterial infection of the human monocyte-derived macrophages:

a. Direct Observation and Counting of the Number of Infected Cells in Each Well

For these experiments, the mycobacteria-infected MDM were cultured in wells of a polystyrene tissue culture plate that had sterile round glass cover slips inserted into the bottoms of the wells. Since the MDMs were originally seeded onto these cover slips, the MDMs adhered to the cover slip surfaces. After incubation with MAC or TB, the wells were washed twice (as stated above) and then fixed ×1 hr using glutaraldehyde. The mycobacteria were then stained using a mycobacterial stain (Zeihl-Nielsson) without injuring the cells. The number of infected cells was quantified optically and the data expressed as a percent of the total number of MDM in each well.

b. Colony Counts

After the infected cells were washed twice (see above), the cells in parallel wells that did not contain cover slips were lysed using 1.0 ml of lysing buffer per well for 5.0 min (0.25% sDKF lysis buffer).

After the infected MDM were lysed (see above), the lysate fluid was diluted 1:1 with 1.0 ml of 7H9 medium. The mycobacterial suspension was diluted serially 1:10 into 1% (vol/vol) 7H9 medium and sterile water. The diluted mycobacterial suspensions were vortexed and then 0.5 ml of the suspension from each aliquot was plated onto mycobacteria medium (solid 7H9 medium). This mycobacteria-containing fluid was then cultured. The plates were incubated for 10-12 days for MAC and for 21-24 days for Tuberculosis, and the number of mycobacterial colonies counted.

Results:
Tuberculosis

DIRECT OBSERVATION DATA

| | Control MDM (no AAT)[a] | ATT (5.0 mg/ml)-exposed MDM |
|---|---|---|
| Experiment 1 | 20% | 4% |
| Experiment 2 | 17% | 6% |

[a]percent of cells infected with m. tuberculosis.

Colony Count Data

In a separate experiment, we cultured the cell-associated TB to independently confirm the inhibitory AAT effect. The TB counts per ml were $1.6 \times 10^5$ per ml in the control MDM cultures and $0.57 \times 10^5$ per ml in the AAT-exposed cultures, an inhibitory effect of 64% due to the presence of AAT.

*Mycobacterium Avium* Complex

We used the related mycobacterial organisms known as *mycobacterium avium* complex (MAC). MAC is important because it is a leading cause of infectious disease in AIDS patients. It is also a difficult problem in normal people who contract this infection; it is very difficult to treat, and sometimes impossible to treat with current antimicrobial drugs. Using AAT or an AAT-like molecule may represent a novel means of therapy in these infections.

Direct Observation Data

| | Control MDM (no AAT)[a] | ATT (5.0 mg/ml)-exposed MDM |
|---|---|---|
| Experiment 1 | 17% | 10% | a. [a]percent of cells infected with m. tuberculosis.

Colony Count Data

FIG. 1 shows the results of 4 separate experiments that demonstrate that AAT significantly blocks infection of MDM with MAC with a mean effect of approximately 55% inhibition. These experiments were conducted as described above. The AAT mimic refers to ala-ala-pro-val-chloromethyl ketone (an AAT-like synthetic serine protease inhibitor)(Supplier: Bachem). The AAT mimic results confirm the AAT data using an independent species, and provide proof that the concept of serine protease inhibition to treat mycobacterial infections extends to small molecule inhibitors that make attractive drug candidates.

Figure 2:
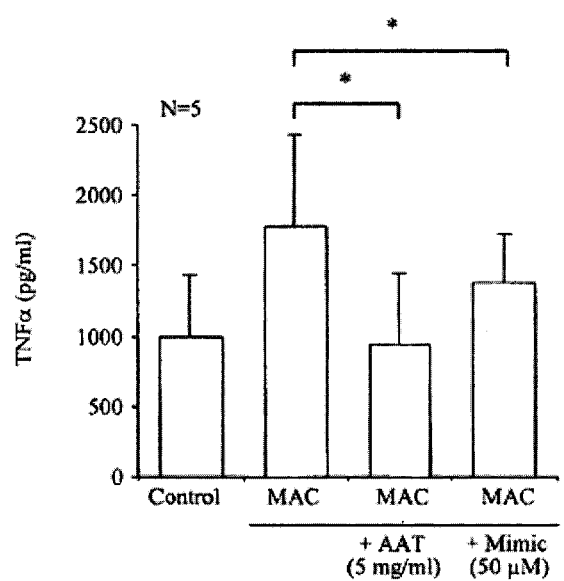
FIG. 2 illustrates the effect of α-1-antitrypsin (AAT) and AAT mimic on *mycobacterium avium* complex (mac)-induced TNFα in human monocyte-derived macrophages.
Figure 3:
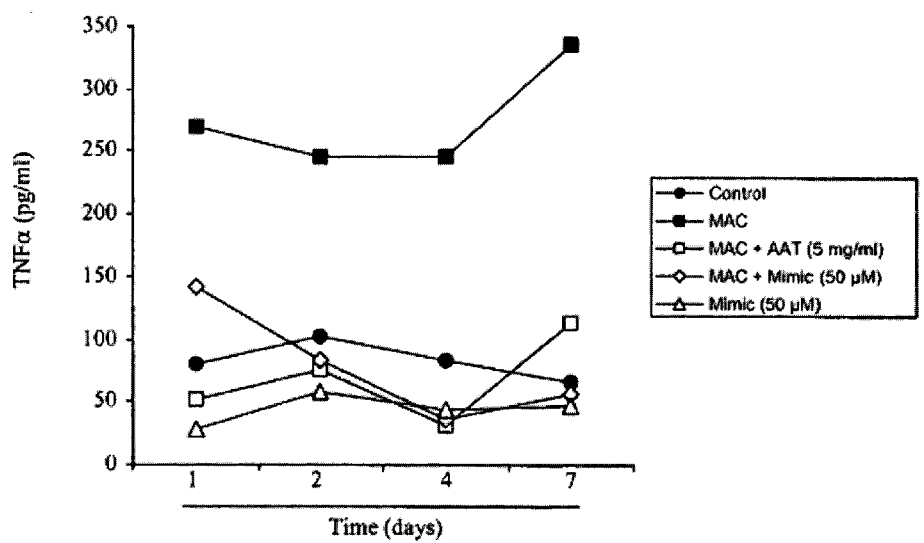
FIG. 3 illustrates the effect of α-1-antitrypsin (AAT) and aat mimic on *mycobacterium avium* complex (mac)-induced TNFα in human monocyte-derived macrophages: time-course experiment (n=1).
Figure 4:
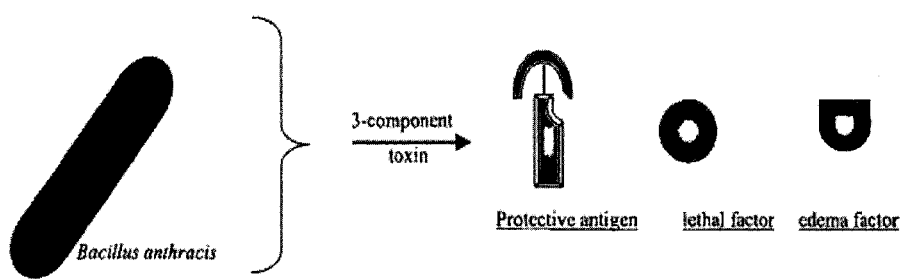
FIGS. 4A-4H illustrate the *bacillus anthracis* toxin mechanism and the method by which serine protease inhibitors neutralize the toxin.
Figure 4:
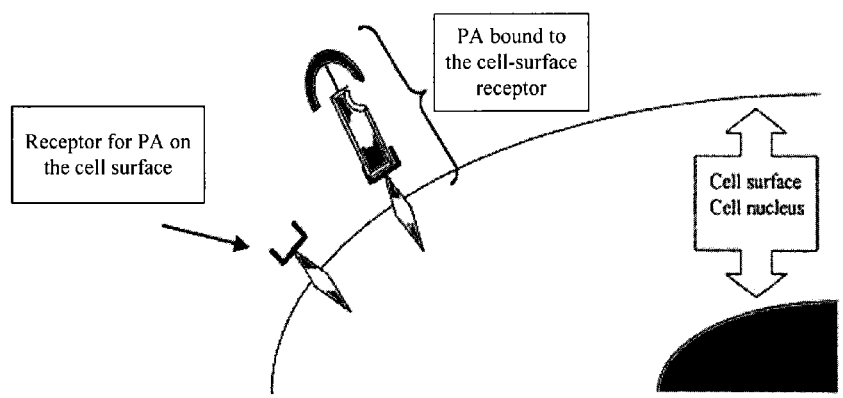
Figure 4:
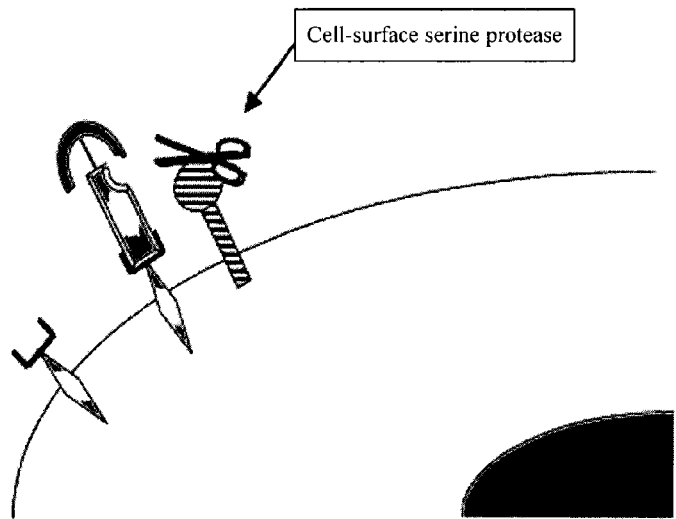
Figure 4:
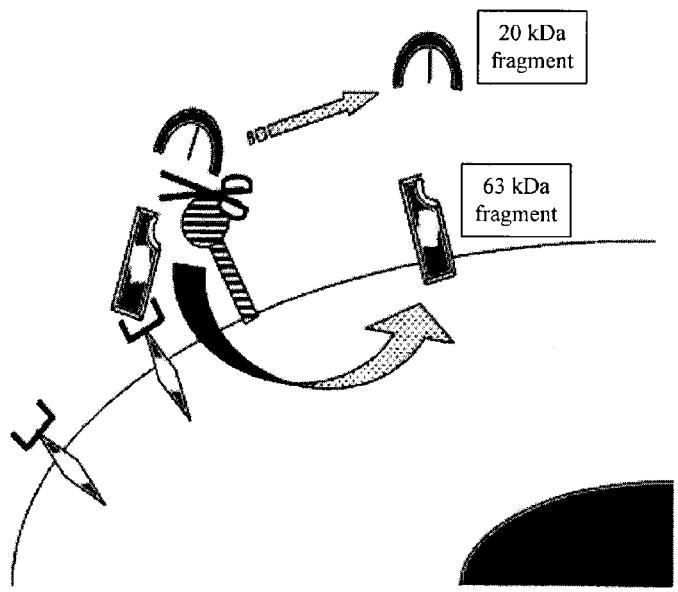
Figure 4:
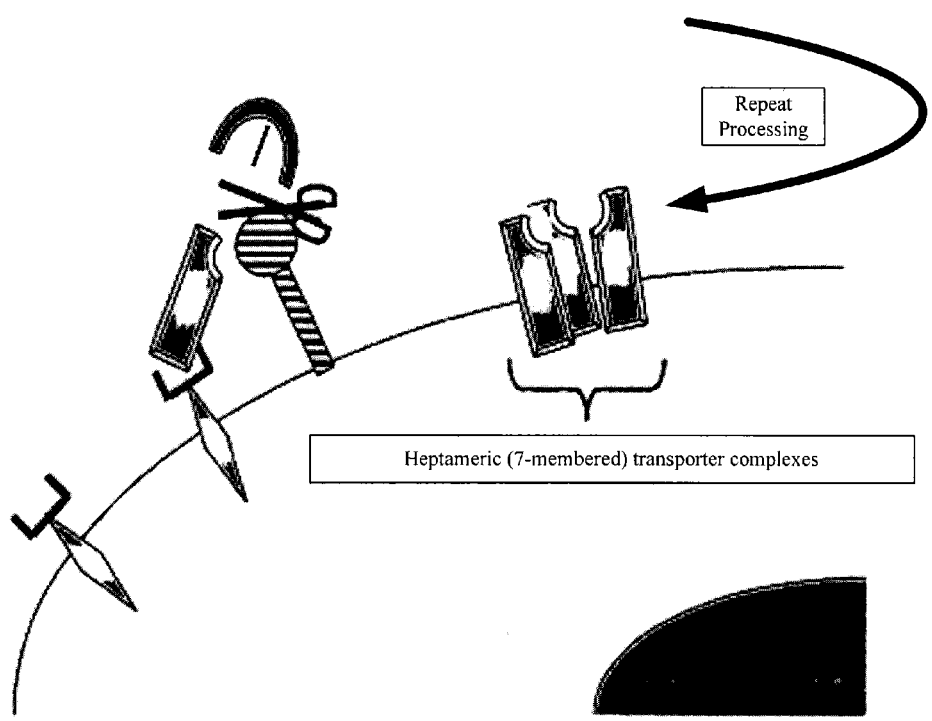
Figure 4:
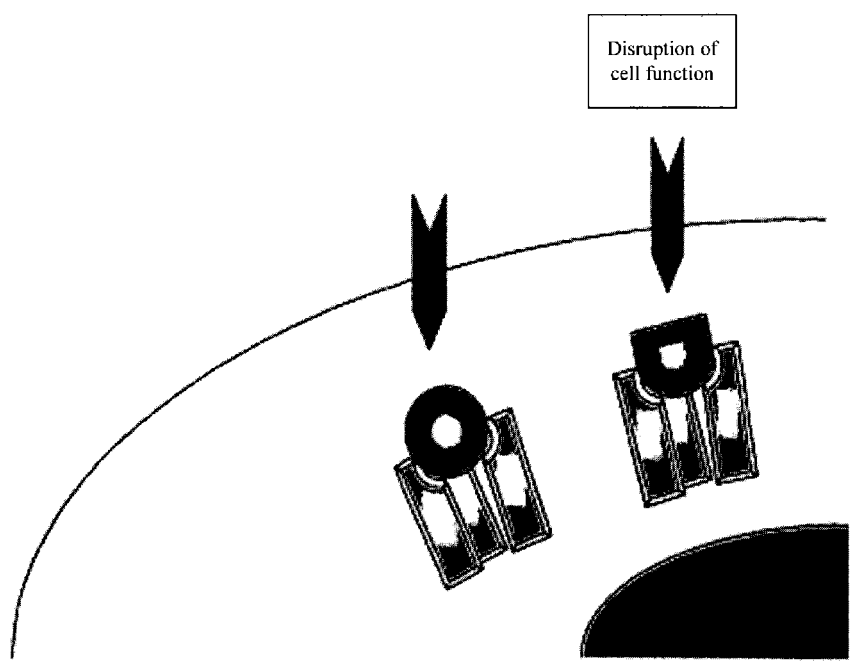
Figure 4:
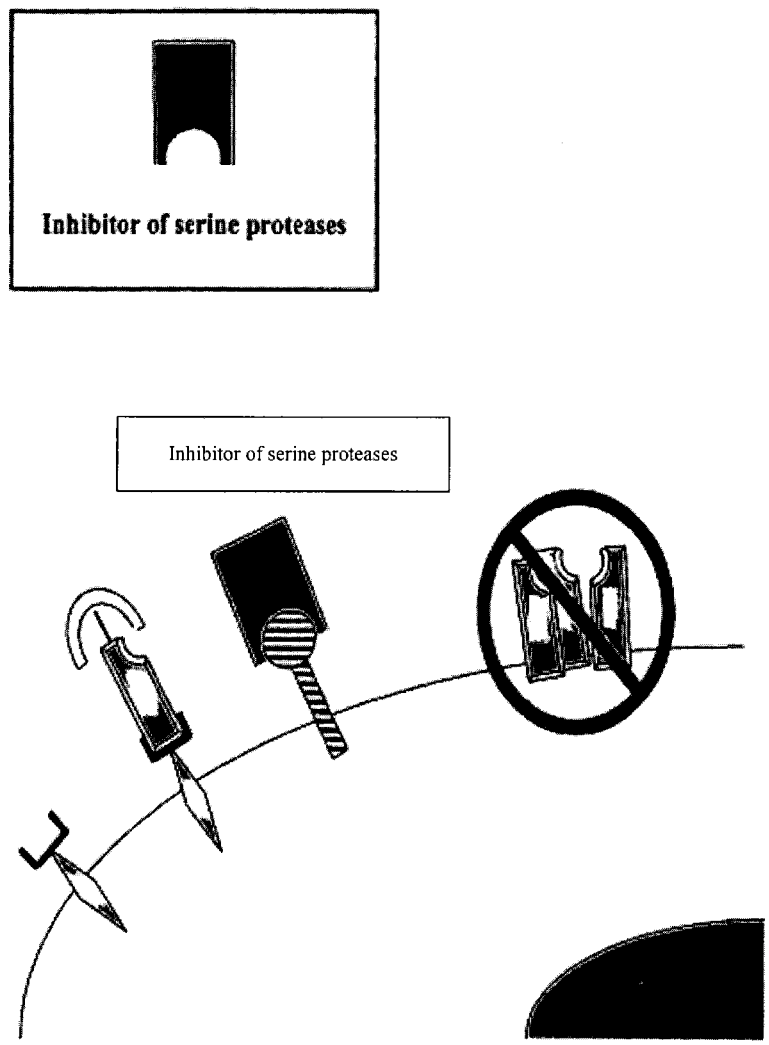

In the same cultures depicted above, we measured the concentration of the pro-inflammatory cytokine TNFα. As shown in FIG. 2 and FIG. 3, AAT and the AAT mimic both significantly inhibited the production of TNFα in the MDM cultures by up to 100%. The blockade of pro-inflammatory cytokine production may represent an additional mechanism by which serine protease inhibitors block infection with TB and with MAC.

Example Two

Clinical Study in MAC Infection

The data described above in vitro using MAC have been supplemented with a clinical study. In this clinical investigation, AAT phenotypes (alternative forms of the AAT protein) were assessed in patients with documented lung infection with MAC and who had lung disease. These patients were compared to a control group consisting of patients with the lung disease bronchiectasis (in order to show that the presence of lung disease alone did not account for the presence of MAC infection).

| N = 134 subjects | MAC Infection (lungs) | Bronchiectasis (lung disease) | P-value |
|---|---|---|---|
| Sex- | | | |
| Male | 8.97% | 23.21% | |
| Female | 91.3% | 76.79% | |
| Age (mean) | 64.5 yrs | 64.0 yrs | |
| ATT phenotype (% abnormal)- | | | 0.006 |
| YES | 27.7% | 5.3% | |
| NO | 72.3% | 94.7% | |

Note in this table that that for the control (bronchiectasis) group, the proportion of patients with abnormal AAT molecules is 5.3%. This is in marked contrast to the case in the MAC.quadrature.infected group, where the proportion is 27.7%, a 5.2 fold increase. The MAC.quadrature.infected patients were 5.2 times as likely as the control group to harbor an abnormal form of AAT. This establishes a clinical link between abnormal AAT molecules and infection with MAC. Thus, the inhibitory role of normal AAT that we discovered in vitro is borne out in patients.

Example Three

Effect of α-1-Antitrypsin on Stimulated Interleukin-1 Beta Production in Whole Human Blood Design: Venipuncture was performed on 3 healthy volunteers using a 21-gauge needle, and the venous blood was aspirated into a heparinized tube. Blood was then aliquoted into 6 milliliter polypropylene tubes and diluted 1:4 with sterile RPMI tissue culture medium alone (Control), diluted 1:4 in medium containing heat-killed *Staphylococcus epidermidis* at a final concentration of 1:1000 as a stimulus (Staph), or into tubes containing *Staphylococcus epidermidis* and α-1-antitrypsin (AAT, Aralast® from Baxter). All cultures were then incubated .times.24 hrs at 37.degree. C./5% CO.sub.2). Following incubation, the samples were centrifuged .times.1,500 g, and the supernatants collected. Supernatants were assayed for interleukin-1 beta concentration using a validated electrochemiluminescence apparatus that quantifies cytokine proteins.

Figure 5:
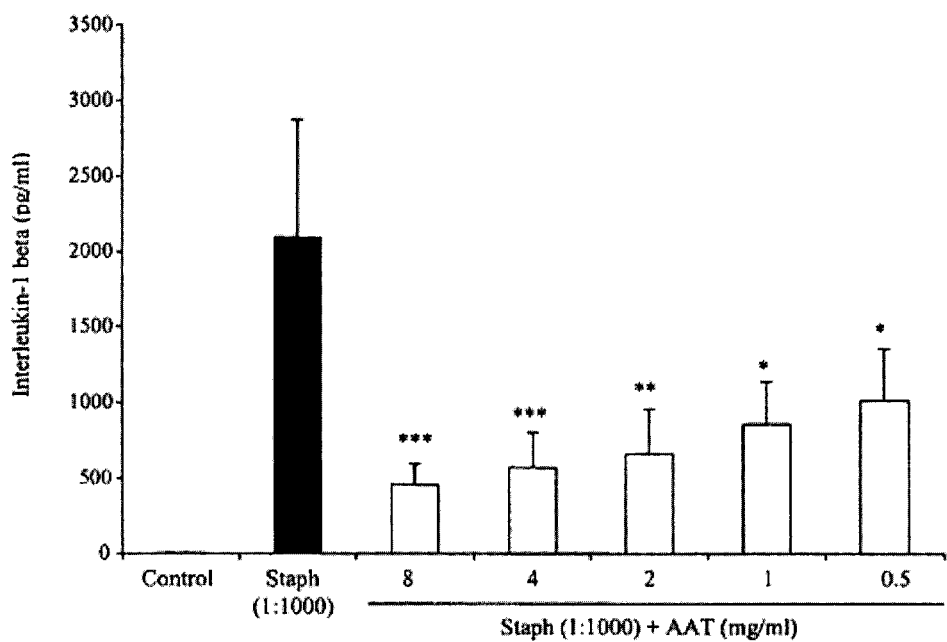
FIG. 5 illustrates the effect of α-1-antitrypsin on stimulated interleukin-1 beta production in whole human blood.

Results:

The data are presented as the mean.+-.SEM interleukin-1 beta production, and the values are shown on the vertical axis. As shown, AAT significantly inhibited *Staph*-stimulated inteleukin-1 beta production dose-dependently, and the inhibition was observed at all concentrations tested (See FIG. 5).

Discussion:

The inventors have shown herein for the first time that AAT blocks IL-1 beta production as an example of proinflammatory cytokine production. IL-1 beta is crucial for development of the symptoms and/or manefestations of anthrax disease. The results presented in this example supplement the already supposed mechanism by which AAT may be used as a therapeutic agent to cure anthrax by blocking the production of the active toxin.

Example Four

In outpatient pneumonias, it is known that gram-positive organisms predominate whereas in the intensive care unit (ICU), gram-negative pneumonias are disproportionately incident.

The pathogenesis of pneumonia involves colonization followed by micro-aspiration. Persons in the ICU become colonized with gram-negative rods. Therefore, it is apparent to physicians that only sick persons in the ICU become colonized with gram-negative rods. Processed fibronectin is an important receptor for gram-negative bacilli in vivo.

One means of treating patients with gram-negative pneumonias would be to block gram-negative rod colonization. For example, in health, unprocessed fibronectin is not a receptor for gram negative bacteria. During illness, secretions become rich in serine proteases. Serine proteases process (proteolize) fibronectin. Processed fibronectin is a receptor for gram negative bacteria. This results in colonization. The use of serine protease inhibitors like α-1 antitrypsin or any of the functional derivatives thereof as disclosed in this application can be used by one of ordinary skill in the art to block gram-negative rod colonization and therefore treat Gram-negative pneumonias. Thus, serine protease inhibitors like AAT can be adminstered topically using topical formulations including, for example, but not limited to, liquid, cream, aerosol, etc., to block colonizqtion of the epithelium by Gram negative rods. Representative examples of publications providing non-limiting examples of Gram negative bacilli that may treated using the compositions of the present invention may be found in Charlotte L. Barey-Morel et al. The Journal of Infectious Diseases VI 155, No. 4 (1987); W. G. Johanson et al. Annals of Internal Medicine 77: 701-706 (1972); W. G. Johanson et al. The New England Journal of Medicine Vol 281 No. 21 (1969); James J. Rahal et al. JAMA Vol. 214 No. 4 (1970), the entire texts of each of which are incorporated by reference.

In a similar fashion serine protease inhibitors like AAT could be administered topically using topical formulations including, for example, but not limited to, liquid, cream, aerosol, etc., to treat bacterial infections caused by Gram positive organisms.

Likewise, in a similar fashion serine protease inhibitors like AAT could be administered topically using topical formulations including, for example, but not limited to, liquid, cream, aerosol, etc., to treat bacterial infections caused by mycobacteria. For the proposed mechanism of action for atypical mycobacteria, please refer to Examples 1 and 2 supra.

Throughout this application various publications and patents are referenced. The disclosures of these publications and patents in their entireties are hereby incorporated by reference into this application in order to more fully describe the state of the art to which this invention pertains.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed:

1. A pharmaceutical composition of a fusion polypeptide construct comprising:
   a first polypeptide comprising mammalian alpha-1 antitrypsin (AAT), wherein the first polypeptide comprising mammalian ATT is represented by SEQ ID NO:69 or SEQ ID NO:79, a second polypeptide comprising an IgG1 Fc, an immunoglobulin constant region; and
   a pharmaceutically acceptable excipient thereof.

2. A pharmaceutical composition of a fusion polypeptide construct:
   wherein the construct comprises a fusion polypeptide represented by SEQ ID NO: 75, SEQ ID NO: 87, SEQ ID NO: 85 or SEQ ID NO: 89 and a pharmaceutically acceptable excipient thereof.

3. A pharmaceutical composition of a fusion polypeptide construct:
   wherein the construct comprises a fusion polypeptide represented by SEQ ID NO: 71, SEQ ID NO: 73, SEQ ID NO: 81 or SEQ ID NO: 83 and a pharmaceutically acceptable excipient thereof.

4. An isolated preparation of expressed inclusion bodies comprising the construct of claim 1.

5. The pharmaceutical composition of claim 1, wherein the composition is formulated for inhalation, intranasal, intravenous, intramolecular or subcutaneous administration.

6. An isolated preparation of expressed inclusion bodies comprising the construct of claim.

7. The pharmaceutical composition of claim 2, wherein the composition is formulated for inhalation, intranasal, intravenous, intramuscular or subcutaneous administration.

8. An isolated preparation of expressed inclusion bodies comprising the construct of claim 3.

9. The pharmaceutical composition of claim 3, wherein the composition is formulated for inhalation, intranasal, intravenous, intramuscular or subcutaneous administration.

* * * * *

UNITED STATES PATENT AND TRADEMARK OFFICE
CERTIFICATE OF CORRECTION

Page 1 of 1

PATENT NO. : 9,499,606 B2
APPLICATION NO. : 13/958443
DATED : November 22, 2016
INVENTOR(S) : L. Shapiro et al.

It is certified that error appears in the above-identified patent and that said Letters Patent is hereby corrected as shown below:

In Column 126, Line 49, in Claim 6, insert --1-- after the word "claim."

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 89

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Phe Val Phe Leu Met
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Ala Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3
```

```
Phe Val Ala Leu Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Phe Leu Ala
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Leu Val Phe Ile
1               5

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Phe Leu Met Ile Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Phe Leu Phe Val Leu
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Val
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Leu Ile
```

```
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Phe Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Met Phe Ile
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Phe Met Leu Leu Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Ile Ile Met Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Leu Phe Cys Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Ala Val
1               5
```

```
<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Val Tyr Leu Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Ala Phe Leu Met
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

<400> SEQUENCE: 18

Ala Val Phe Leu Met
1               5

<210> SEQ ID NO 19
<211> LENGTH: 10
<212> TYPE: PRT
<213> ORGANISM: Homo sapiens

<400> SEQUENCE: 19

Met Pro Ser Ser Val Ser Trp Gly Ile Leu
1               5                   10

<210> SEQ ID NO 20
<211> LENGTH: 10
<212> TYPE: PRT
<213> ORGANISM: Homo sapiens

<400> SEQUENCE: 20

Leu Ala Gly Leu Cys Cys Leu Val Pro Val
1               5                   10

<210> SEQ ID NO 21
<211> LENGTH: 10
<212> TYPE: PRT
<213> ORGANISM: Homo sapiens

<400> SEQUENCE: 21

Ser Leu Ala Glu Asp Pro Gln Gly Asp Ala
1               5                   10

<210> SEQ ID NO 22
<211> LENGTH: 10
<212> TYPE: PRT
<213> ORGANISM: Homo sapiens
```

<400> SEQUENCE: 22

Ala Gln Lys Thr Asp Thr Ser His His Asp
1               5                   10

<210> SEQ ID NO 23
<211> LENGTH: 10
<212> TYPE: PRT
<213> ORGANISM: Homo sapiens

<400> SEQUENCE: 23

Gln Asp His Pro Thr Phe Asn Lys Ile Thr
1               5                   10

<210> SEQ ID NO 24
<211> LENGTH: 10
<212> TYPE: PRT
<213> ORGANISM: Homo sapiens

<400> SEQUENCE: 24

Pro Asn Leu Ala Glu Phe Ala Phe Ser Leu
1               5                   10

<210> SEQ ID NO 25
<211> LENGTH: 10
<212> TYPE: PRT
<213> ORGANISM: Homo sapiens

<400> SEQUENCE: 25

Tyr Arg Gln Leu Ala His Gln Ser Asn Ser
1               5                   10

<210> SEQ ID NO 26
<211> LENGTH: 10
<212> TYPE: PRT
<213> ORGANISM: Homo sapiens

<400> SEQUENCE: 26

Thr Asn Ile Phe Phe Ser Pro Val Ser Ile
1               5                   10

<210> SEQ ID NO 27
<211> LENGTH: 10
<212> TYPE: PRT
<213> ORGANISM: Homo sapiens

<400> SEQUENCE: 27

Ala Thr Ala Phe Ala Met Leu Ser Leu Gly
1               5                   10

<210> SEQ ID NO 28
<211> LENGTH: 10
<212> TYPE: PRT
<213> ORGANISM: Homo sapiens

<400> SEQUENCE: 28

Thr Lys Ala Asp Thr His Asp Glu Ile Leu
1               5                   10

<210> SEQ ID NO 29
<211> LENGTH: 10
<212> TYPE: PRT
<213> ORGANISM: Homo sapiens

<400> SEQUENCE: 29

```
Glu Gly Leu Asn Phe Asn Leu Thr Glu Ile
1               5                   10
```

<210> SEQ ID NO 30
<211> LENGTH: 10
<212> TYPE: PRT
<213> ORGANISM: Homo sapiens

<400> SEQUENCE: 30

```
Pro Glu Ala Gln Ile His Glu Gly Phe Gln
1               5                   10
```

<210> SEQ ID NO 31
<211> LENGTH: 10
<212> TYPE: PRT
<213> ORGANISM: Homo sapiens

<400> SEQUENCE: 31

```
Glu Leu Leu Arg Thr Leu Asn Gln Pro Asp
1               5                   10
```

<210> SEQ ID NO 32
<211> LENGTH: 10
<212> TYPE: PRT
<213> ORGANISM: Homo sapiens

<400> SEQUENCE: 32

```
Ser Gln Leu Gln Leu Thr Thr Gly Asn Gly
1               5                   10
```

<210> SEQ ID NO 33
<211> LENGTH: 10
<212> TYPE: PRT
<213> ORGANISM: Homo sapiens

<400> SEQUENCE: 33

```
Leu Phe Leu Ser Glu Gly Leu Lys Leu Val
1               5                   10
```

<210> SEQ ID NO 34
<211> LENGTH: 10
<212> TYPE: PRT
<213> ORGANISM: Homo sapiens

<400> SEQUENCE: 34

```
Asp Lys Phe Leu Glu Asp Val Lys Lys Leu
1               5                   10
```

<210> SEQ ID NO 35
<211> LENGTH: 10
<212> TYPE: PRT
<213> ORGANISM: Homo sapiens

<400> SEQUENCE: 35

```
Tyr His Ser Glu Ala Phe Thr Val Asn Phe
1               5                   10
```

<210> SEQ ID NO 36
<211> LENGTH: 10
<212> TYPE: PRT
<213> ORGANISM: Homo sapiens

<400> SEQUENCE: 36

```
Gly Asp His Glu Glu Ala Lys Lys Gln Ile
1               5                   10
```

<210> SEQ ID NO 37
<211> LENGTH: 10
<212> TYPE: PRT
<213> ORGANISM: Homo sapiens

<400> SEQUENCE: 37

Asn Asp Tyr Val Glu Lys Gly Thr Gln Gly
1               5                   10

<210> SEQ ID NO 38
<211> LENGTH: 10
<212> TYPE: PRT
<213> ORGANISM: Homo sapiens

<400> SEQUENCE: 38

Lys Ile Val Asp Leu Val Lys Glu Leu Asp
1               5                   10

<210> SEQ ID NO 39
<211> LENGTH: 10
<212> TYPE: PRT
<213> ORGANISM: Homo sapiens

<400> SEQUENCE: 39

Arg Asp Thr Val Phe Ala Leu Val Asn Tyr
1               5                   10

<210> SEQ ID NO 40
<211> LENGTH: 10
<212> TYPE: PRT
<213> ORGANISM: Homo sapiens

<400> SEQUENCE: 40

Ile Phe Phe Lys Gly Lys Trp Glu Arg Pro
1               5                   10

<210> SEQ ID NO 41
<211> LENGTH: 10
<212> TYPE: PRT
<213> ORGANISM: Homo sapiens

<400> SEQUENCE: 41

Phe Glu Val Lys Asp Thr Glu Asp Glu Asp
1               5                   10

<210> SEQ ID NO 42
<211> LENGTH: 10
<212> TYPE: PRT
<213> ORGANISM: Homo sapiens

<400> SEQUENCE: 42

Phe His Val Asp Gln Val Thr Thr Val Lys
1               5                   10

<210> SEQ ID NO 43
<211> LENGTH: 10
<212> TYPE: PRT
<213> ORGANISM: Homo sapiens

<400> SEQUENCE: 43

Val Pro Met Met Lys Arg Leu Gly Met Phe
1               5                   10

```
<210> SEQ ID NO 44
<211> LENGTH: 10
<212> TYPE: PRT
<213> ORGANISM: Homo sapiens

<400> SEQUENCE: 44

Asn Ile Gln His Cys Lys Lys Leu Ser Ser
1               5                   10

<210> SEQ ID NO 45
<211> LENGTH: 10
<212> TYPE: PRT
<213> ORGANISM: Homo sapiens

<400> SEQUENCE: 45

Trp Val Leu Leu Met Lys Tyr Leu Gly Asn
1               5                   10

<210> SEQ ID NO 46
<211> LENGTH: 10
<212> TYPE: PRT
<213> ORGANISM: Homo sapiens

<400> SEQUENCE: 46

Ala Thr Ala Ile Phe Phe Leu Pro Asp Glu
1               5                   10

<210> SEQ ID NO 47
<211> LENGTH: 10
<212> TYPE: PRT
<213> ORGANISM: Homo sapiens

<400> SEQUENCE: 47

Gly Lys Leu Gln His Leu Glu Asn Glu Leu
1               5                   10

<210> SEQ ID NO 48
<211> LENGTH: 10
<212> TYPE: PRT
<213> ORGANISM: Homo sapiens

<400> SEQUENCE: 48

Thr His Asp Ile Ile Thr Lys Phe Leu Glu
1               5                   10

<210> SEQ ID NO 49
<211> LENGTH: 10
<212> TYPE: PRT
<213> ORGANISM: Homo sapiens

<400> SEQUENCE: 49

Asn Glu Asp Arg Arg Ser Ala Ser Leu His
1               5                   10

<210> SEQ ID NO 50
<211> LENGTH: 10
<212> TYPE: PRT
<213> ORGANISM: Homo sapiens

<400> SEQUENCE: 50

Leu Pro Lys Leu Ser Ile Thr Gly Thr Tyr
1               5                   10

<210> SEQ ID NO 51
<211> LENGTH: 10
```

```
<212> TYPE: PRT
<213> ORGANISM: Homo sapiens

<400> SEQUENCE: 51

Asp Leu Lys Ser Val Leu Gly Gln Leu Gly
1               5                   10

<210> SEQ ID NO 52
<211> LENGTH: 10
<212> TYPE: PRT
<213> ORGANISM: Homo sapiens

<400> SEQUENCE: 52

Ile Thr Lys Val Phe Ser Asn Gly Ala Asp
1               5                   10

<210> SEQ ID NO 53
<211> LENGTH: 10
<212> TYPE: PRT
<213> ORGANISM: Homo sapiens

<400> SEQUENCE: 53

Leu Ser Gly Val Thr Glu Glu Ala Pro Leu
1               5                   10

<210> SEQ ID NO 54
<211> LENGTH: 10
<212> TYPE: PRT
<213> ORGANISM: Homo sapiens

<400> SEQUENCE: 54

Lys Leu Ser Lys Ala Val His Lys Ala Val
1               5                   10

<210> SEQ ID NO 55
<211> LENGTH: 10
<212> TYPE: PRT
<213> ORGANISM: Homo sapiens

<400> SEQUENCE: 55

Leu Thr Ile Asp Glu Lys Gly Thr Glu Ala
1               5                   10

<210> SEQ ID NO 56
<211> LENGTH: 10
<212> TYPE: PRT
<213> ORGANISM: Homo sapiens

<400> SEQUENCE: 56

Ala Gly Ala Met Phe Leu Glu Ala Ile Pro
1               5                   10

<210> SEQ ID NO 57
<211> LENGTH: 10
<212> TYPE: PRT
<213> ORGANISM: Homo sapiens

<400> SEQUENCE: 57

Met Ser Ile Pro Pro Glu Val Lys Phe Asn
1               5                   10

<210> SEQ ID NO 58
<211> LENGTH: 10
<212> TYPE: PRT
<213> ORGANISM: Homo sapiens
```

<400> SEQUENCE: 58

Lys Pro Phe Val Phe Leu Met Ile Glu Gln
1               5                   10

<210> SEQ ID NO 59
<211> LENGTH: 10
<212> TYPE: PRT
<213> ORGANISM: Homo sapiens

<400> SEQUENCE: 59

Asn Thr Lys Ser Pro Leu Phe Met Gly Lys
1               5                   10

<210> SEQ ID NO 60
<211> LENGTH: 7
<212> TYPE: PRT
<213> ORGANISM: Homo sapiens

<400> SEQUENCE: 60

Val Val Asn Pro Thr Gln Lys
1               5

<210> SEQ ID NO 61
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: native sequence

<400> SEQUENCE: 61

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
        50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
                145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

-continued

```
His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
        340                 345                 350

Leu Glu Ala Ile Pro Met Ser Ile Pro Pro Glu Val Lys Phe Asn Lys
    355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 62
<211> LENGTH: 394
<212> TYPE: PRT
<213> ORGANISM: Homo sapiens
<220> FEATURE:
<221> NAME/KEY: MISC_FEATURE
<222> LOCATION: (355)..(358)
<223> OTHER INFORMATION: novel sequence
<220> FEATURE:
<221> NAME/KEY: MISC_FEATURE
<222> LOCATION: (356)..(357)
<223> OTHER INFORMATION: Xaa = any amino acid

<400> SEQUENCE: 62

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
            85                  90                  95

Gln Glu Leu Leu Arg Thr Leu Asn Gln Pro Asp Ser Gln Leu Gln Leu
        100                 105                 110

Thr Thr Gly Asn Gly Leu Phe Leu Ser Glu Gly Leu Lys Leu Val Asp
    115                 120                 125

Lys Phe Leu Glu Asp Val Lys Lys Leu Tyr His Ser Glu Ala Phe Thr
130                 135                 140
```

Val Asn Phe Gly Asp His Glu Glu Ala Lys Lys Gln Ile Asn Asp Tyr
145                 150                 155                 160

Val Glu Lys Gly Thr Gln Gly Lys Ile Val Asp Leu Val Lys Glu Leu
            165                 170                 175

Asp Arg Asp Thr Val Phe Ala Leu Val Asn Tyr Ile Phe Phe Lys Gly
        180                 185                 190

Lys Trp Glu Arg Pro Phe Glu Val Lys Asp Thr Glu Asp Glu Asp Phe
    195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
        340                 345                 350

Leu Glu Arg Xaa Xaa Arg Ser Ile Pro Pro Glu Val Lys Phe Asn Lys
    355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 63
<211> LENGTH: 417
<212> TYPE: PRT
<213> ORGANISM: Homo sapiens

<400> SEQUENCE: 63

Met Pro Ser Ser Val Ser Trp Gly Ile Leu Leu Ala Gly Leu Cys Cys
1               5                   10                  15

Leu Val Pro Val Ser Leu Ala Glu Asp Pro Gln Gly Asp Ala Ala Gln
            20                  25                  30

Lys Thr Asp Thr Ser His His Asp Gln Asp His Pro Thr Phe Asn Lys
        35                  40                  45

Ile Thr Pro Asn Leu Ala Glu Phe Ala Phe Ser Leu Tyr Arg Gln Leu
    50                  55                  60

Ala His Gln Ser Asn Ser Thr Asn Ile Phe Phe Ser Pro Val Ser Ile
65                  70                  75                  80

Ala Thr Ala Phe Ala Asn Leu Ser Leu Gly Thr Lys Ala Asp Thr His
            85                  90                  95

Asp Glu Ile Leu Glu Gly Leu Asn Phe Asn Leu Thr Glu Ile Pro Glu
        100                 105                 110

Ala Gln Ile His Glu Gly Phe Gln Glu Leu Leu Arg Thr Leu Asn Gln
    115                 120                 125

Pro Asp Ser Gln Leu Gln Leu Thr Thr Gly Asn Gly Leu Phe Leu Ser
    130                 135                 140

Glu Gly Leu Lys Leu Val Asp Lys Phe Leu Glu Asp Val Lys Lys Leu
145                 150                 155                 160

Tyr His Ser Glu Ala Phe Thr Val Asn Phe Gly Asp His Glu Glu Ala
                165                 170                 175

Lys Lys Gln Ile Asn Asp Tyr Val Lys Gly Thr Gln Gly Lys Ile
            180                 185                 190

Val Asp Leu Val Lys Glu Leu Asp Arg Asp Thr Val Phe Ala Leu Val
        195                 200                 205

Asn Tyr Ile Phe Phe Lys Gly Lys Trp Glu Arg Pro Phe Glu Val Lys
210                 215                 220

Asp Thr Glu Asp Glu Asp Phe His Val Asp Gln Val Thr Thr Val Lys
225                 230                 235                 240

Val Pro Met Met Lys Arg Leu Gly Met Phe Asn Ile Gln His Cys Lys
                245                 250                 255

Lys Leu Ser Ser Trp Val Leu Leu Met Lys Tyr Leu Gly Asn Ala Thr
            260                 265                 270

Ala Ile Phe Phe Leu Pro Asp Glu Gly Lys Leu Gln His Leu Glu Asn
        275                 280                 285

Glu Leu Thr His Asp Ile Ile Thr Lys Phe Leu Glu Asn Glu Asp Arg
290                 295                 300

Arg Ser Ala Ser Leu His Leu Pro Lys Leu Ser Ile Thr Gly Thr Tyr
305                 310                 315                 320

Asp Leu Lys Ser Val Leu Gly Gln Leu Gly Ile Thr Lys Val Phe Ser
                325                 330                 335

Asn Gly Ala Asp Leu Ser Gly Val Thr Glu Glu Ala Pro Leu Lys Leu
            340                 345                 350

Ser Lys Ala Val His Lys Ala Val Leu Thr Ile Asp Glu Lys Gly Thr
        355                 360                 365

Glu Ala Ala Gly Ala Met Phe Leu Glu Ala Ile Pro Met Ser Ile Pro
370                 375                 380

Pro Glu Val Lys Phe Asn Lys Pro Phe Val Phe Leu Met Ile Glu Gln
385                 390                 395                 400

Asn Thr Lys Ser Pro Leu Phe Met Gly Lys Val Val Asn Pro Thr Gln
                405                 410                 415

Lys

<210> SEQ ID NO 64
<211> LENGTH: 699
<212> TYPE: DNA
<213> ORGANISM: Artificial Sequence
<220> FEATURE:
<223> OTHER INFORMATION: derived from IgG1, FC

<400> SEQUENCE: 64
gagcccaaat cttgtgacaa aactcacaca tgcccaccgt gcccagcacc tgaactcctg     60
gggggaccgt cagtcttcct cttccccca aaacccaagg acaccctcat gatctcccgg    120 accccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagcccctcc cagcccccat cgagaaaacc    360

| atctccaaag ccaaagggca gccccgagaa ccacaggtgt acaccctgcc cccatcccgg | 420 |
| gatgagctga ccaagaacca ggtcagcctg acctgcctgg tcaaaggctt ctatcccagc | 480 |
| gacatcgccg tggagtggga gagcaatggg cagccggaga acaactacaa gaccacgcct | 540 |
| cccgtgctgg actccgacgg ctccttcttc ctctacagca agctcaccgt ggacaagagc | 600 |
| aggtggcagc aggggaacgt cttctcatgc tccgtgatgc atgaggctct gcacaaccac | 660 |
| tacacgcaga gagcctctc cctgtctccg ggtaaatga | 699 |

```
<210> SEQ ID NO 65
<211> LENGTH: 232
<212> TYPE: PRT
<213> ORGANISM: Artificial Sequence
<220> FEATURE:
<223> OTHER INFORMATION: derived from IgG1, Fc

<400> SEQUENCE: 65
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

```
<210> SEQ ID NO 66
<211> LENGTH: 1257
<212> TYPE: DNA
<213> ORGANISM: Human AAT

<400> SEQUENCE: 66
```

| atgccgtctt ctgtctcgtg gggcatcctc ctgctggcag gcctgtgctg cctggtccct | 60 |
| gtctccctgg ctgaggatcc ccagggagat gctgcccaga agacagatac atcccaccac | 120 |

-continued

```
gatcaggatc acccaacctt caacaagatc accccaacc tggctgagtt cgccttcagc    180
ctataccgcc agctggcaca ccagtccaac agcaccaata tcttcttctc cccagtgagc    240
atcgctacag ccttttgcaat gctctccctg gggaccaagg ctgacactca cgatgaaatc    300
ctggagggcc tgaatttcaa cctcacggag attccggagg ctcagatcca tgaaggcttc    360
caggaactcc tccgtaccct caaccagcca gacagccagc tccagctgac caccggcaat    420
ggcctgttcc tcagcgaggg cctgaagcta gtggataagt ttttggagga tgttaaaaag    480
ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagttttttgc tctggtgaat acatcttct ttaaaggcaa atgggagaga    660
ccctttgaag tcaaggacac cgaggaagag gacttccacg tggaccaggt gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga gagcgtcct gggtcaactg gcatcacta ggtcttcag caatggggct    1020 gacctctccg ggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200 caaaatacca agtctcccct cttcatggga aagtggtga atcccaccca aaaatga    1257
```

<210> SEQ ID NO 67
<211> LENGTH: 418
<212> TYPE: PRT
<213> ORGANISM: Human AAT

<400> SEQUENCE: 67

```
Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175
```

```
Ala Lys Lys Gln Ile Asn Asp Tyr Val Glu Lys Gly Thr Gln Gly Lys
                180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
        210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
        275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
        355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 68
<211> LENGTH: 1185
<212> TYPE: DNA
<213> ORGANISM: Human AAT

<400> SEQUENCE: 68
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
tttgcaatgc tctccctggg gaccaaggct gacactcacg atgaaatcct ggagggcctg     240
aatttcaacc tcacggagat tccggaggct cagatccatg aaggcttcca ggaactcctc     300
cgtaccctca accagccaga cagccagctc agctgaccca ccgcaatgg cctgttcctc     360
agcgagggcc tgaagctagt ggataagttt ttggaggatg ttaaaaagtt gtaccactca     420
gaagccttca ctgtcaactt cggggacacc gaagaggcca agaaacagat caacgattac     480
gtggagaagg gtactcaagg gaaaattgtg gatttggtca aggagcttga cagagacaca     540
gttttttgctc tggtgaatta catcttcttt aaaggcaaat gggagagacc ctttgaagtc     600
aaggacaccg aggaagagga cttccacgtg gaccaggtga ccaccgtgaa ggtgcctatg     660
atgaagcgtt taggcatgtt taacatccag cactgtaaga agctgtccag ctgggtgctg     720
```

```
ctgatgaaat acctgggcaa tgccaccgcc atcttcttcc tgcctgatga ggggaaacta    780
cagcacctgg aaaatgaact cacccacgat atcatcacca agttcctgga aaatgaagac    840
agaaggtctg ccagcttaca tttacccaaa ctgtccatta ctggaaccta tgatctgaag    900
agcgtcctgg gtcaactggg catcactaag gtcttcagca atggggctga cctctccggg    960
gtcacagagg aggcaccccet gaagctctcc aaggccgtgc ataaggctgt gctgaccatc   1020
gacgagaaag ggactgaagc tgctggggcc atgttttag aggccatacc catgtctatc    1080
ccccccgagg tcaagttcaa caaaccettt gtcttcttaa tgattgaaca aaataccaag    1140
tctcccctct tcatgggaaa agtggtgaat cccacccaaa aatga                   1185
```

<210> SEQ ID NO 69
<211> LENGTH: 394
<212> TYPE: PRT
<213> ORGANISM: Human AAT

<400> SEQUENCE: 69

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
```

```
                290             295             300
Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 70
<211> LENGTH: 1959
<212> TYPE: DNA
<213> ORGANISM: Artificial Sequence
<220> FEATURE:
<223> OTHER INFORMATION: AAT-FC

<400> SEQUENCE: 70
atgccgtctt ctgtctcgtg gggcatcctc ctgctggcag gcctgtgctg cctggtccct       60
gtctccctgg ctgaggatcc ccagggagat gctgcccaga gacagatac atcccaccac      120 gatcaggatc acccaacctt caacaagatc accccaacc tggctgagtt cgccttcagc      180
ctataccgcc agctggcaca ccagtccaac agcaccaata tcttcttctc cccagtgagc      240
atcgctacag cctttgcaat gctctccctg ggaccaagg ctgacactca cgatgaaatc      300
ctggagggcc tgaatttcaa cctcacggag attccggagg ctcagatcca tgaaggcttc      360
caggaactcc tccgtaccct caaccagcca gacagccagc tccagctgac caccggcaat      420
ggcctgttcc tcagcgaggg cctgaagcta gtggataagt ttttggagga tgttaaaaag      480
ttgtaccact cagaagcctt cactgtcaac ttcggggaca ccgaagaggc caagaaacag      540
atcaacgatt acgtggagaa gggtactcaa gggaaaattg tggatttggt caaggagctt      600
gacagagaca cagttttgc tctggtgaat acatcttct ttaaaggcaa atgggagaga      660 cccttttgaag tcaaggacac cgaggaagag acttccacg tggaccaggt gaccaccgtg      720
aaggtgccta tgatgaagcg tttaggcatg tttaacatcc agcactgtaa gaagctgtcc      780
agctgggtgc tgctgatgaa atacctgggc aatgccaccg ccatcttctt cctgcctgat      840
gaggggaaac tacagcacct ggaaaatgaa ctcacccacg atatcatcac caagttcctg      900
gaaaatgaag acagaaggtc tgccagctta catttaccca aactgtccat tactggaacc      960
tatgatctga gagcgtcct gggtcaactg ggcatcacta aggtcttcag caatgggct     1020 gacctctccg ggtcacaga ggaggcaccc tgaagctct ccaaggccgt gcataaggct     1080
gtgctgacca tcgacgagaa agggactgaa gctgctgggg ccatgttttt agaggccata     1140
cccatgtcta tccccccga ggtcaagttc aacaaaccct tgtcttcttc aatgattgaa     1200
caaaatacca agtctcccct cttcatggga aagtggtga atcccaccca aaaaacgcgt     1260
gagcccaaat cttgtgacaa aactcacaca tgcccaccgt gcccagcacc tgaactcctg     1320
gggggaccgt cagtcttcct cttccccca aaacccaagg acaccctcat gatctcccgg     1380 accccctgagg tcacatgcgt ggtggtggac gtgagccacg aagaccctga ggtcaagttc     1440
aactggtacg tggacggcgt ggaggtgcat aatgccaaga caaagccgcg ggaggagcag     1500
```

```
tacaacagca cgtaccgtgt ggtcagcgtc ctcaccgtcc tgcaccagga ctggctgaat    1560
ggcaaggagt acaagtgcaa ggtctccaac aaagccctcc cagccccat cgagaaaacc    1620 atctccaaag ccaaagggca gccccgagaa ccacaggtgt acaccctgcc cccatcccgg    1680
gatgagctga ccaagaacca ggtcagcctg acctgcctgg tcaaaggctt ctatcccagc    1740
gacatcgccg tggagtggga gagcaatggg cagccggaga caactacaa gaccacgcct     1800 cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggtaaatga                          1959
```

<210> SEQ ID NO 71
<211> LENGTH: 652
<212> TYPE: PRT
<213> ORGANISM: Artificial Sequence
<220> FEATURE:
<223> OTHER INFORMATION: AAT-Fc

<400> SEQUENCE: 71

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
```

```
                        275                 280                 285
        Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
    305                 310                 315                 320

Tyr Asp Leu Lys Ser Val Leu Gly Gln Leu Gly Ile Thr Lys Val Phe
                        325                 330                 335

Ser Asn Gly Ala Asp Leu Ser Gly Val Thr Glu Glu Ala Pro Leu Lys
                    340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
        370                 375                 380

Pro Pro Glu Val Lys Phe Asn Lys Pro Phe Val Phe Leu Met Ile Glu
    385                 390                 395                 400

Gln Asn Thr Lys Ser Pro Leu Phe Met Gly Lys Val Val Asn Pro Thr
                        405                 410                 415

Gln Lys Thr Arg Glu Pro Lys Ser Cys Asp Lys Thr His Thr Cys Pro
                    420                 425                 430

Pro Cys Pro Ala Pro Glu Leu Leu Gly Gly Pro Ser Val Phe Leu Phe
                435                 440                 445

Pro Pro Lys Pro Lys Asp Thr Leu Met Ile Ser Arg Thr Pro Glu Val
        450                 455                 460

Thr Cys Val Val Val Asp Val Ser His Glu Asp Pro Glu Val Lys Phe
    465                 470                 475                 480

Asn Trp Tyr Val Asp Gly Val Glu Val His Asn Ala Lys Thr Lys Pro
                        485                 490                 495

Arg Glu Glu Gln Tyr Asn Ser Thr Tyr Arg Val Val Ser Val Leu Thr
                    500                 505                 510

Val Leu His Gln Asp Trp Leu Asn Gly Lys Glu Tyr Lys Cys Lys Val
                515                 520                 525

Ser Asn Lys Ala Leu Pro Ala Pro Ile Glu Lys Thr Ile Ser Lys Ala
        530                 535                 540

Lys Gly Gln Pro Arg Glu Pro Gln Val Tyr Thr Leu Pro Pro Ser Arg
    545                 550                 555                 560

Asp Glu Leu Thr Lys Asn Gln Val Ser Leu Thr Cys Leu Val Lys Gly
                        565                 570                 575

Phe Tyr Pro Ser Asp Ile Ala Val Glu Trp Glu Ser Asn Gly Gln Pro
                    580                 585                 590

Glu Asn Asn Tyr Lys Thr Thr Pro Pro Val Leu Asp Ser Asp Gly Ser
                595                 600                 605

Phe Phe Leu Tyr Ser Lys Leu Thr Val Asp Lys Ser Arg Trp Gln Gln
        610                 615                 620

Gly Asn Val Phe Ser Cys Ser Val Met His Glu Ala Leu His Asn His
    625                 630                 635                 640

Tyr Thr Gln Lys Ser Leu Ser Leu Ser Pro Gly Lys
                        645                 650

<210> SEQ ID NO 72
<211> LENGTH: 1953
<212> TYPE: DNA
<213> ORGANISM: Artificial Sequence
<220> FEATURE:
<223> OTHER INFORMATION: AAT-Fc
```

<400> SEQUENCE: 72

```
atgccgtctt ctgtctcgtg gggcatcctc ctgctggcag gcctgtgctg cctggtccct      60
gtctccctgg ctgaggatcc ccagggagat gctgcccaga agacagatac atcccaccac     120
gatcaggatc acccaacctt caacaagatc acccccaacc tggctgagtt cgccttcagc     180
ctataccgcc agctggcaca ccagtccaac agcaccaata tcttcttctc cccagtgagc     240
atcgctacag cctttgcaat gctctccctg gggaccaagg ctgacactca cgatgaaatc     300
ctggagggcc tgaatttcaa cctcacggag attccggagg ctcagatcca tgaaggcttc     360
caggaactcc tccgtaccct caaccagcca gacagccagc tccagctgac caccggcaat     420
ggcctgttcc tcagcgaggg cctgaagcta gtggataagt ttttggagga tgttaaaaag     480
ttgtaccact cagaagcctt cactgtcaac ttcggggaca ccgaagaggc caagaaacag     540
atcaacgatt acgtggagaa gggtactcaa gggaaaattg tggatttggt caaggagctt     600
gacagagaca cagttttgc tctggtgaat tacatcttct ttaaaggcaa atgggagaga     660
cccttgaag tcaaggacac cgaggaagag gacttccacg tggaccaggt gaccaccgtg     720
aaggtgccta tgatgaagcg tttaggcatg tttaacatcc agcactgtaa gaagctgtcc     780
agctgggtgc tgctgatgaa atacctgggc aatgccaccg ccatcttctt cctgcctgat     840
gaggggaaac tacagcacct ggaaaatgaa ctcacccacg atatcatcac caagttcctg     900
gaaaatgaag acagaaggtc tgccagctta catttaccca aactgtccat tactggaacc     960
tatgatctga gagcgtcct gggtcaactg gcatcacta aggtcttcag caatggggct    1020
gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct tgtcttctt aatgattgaa    1200
caaaatacca gtctcccct cttcatggga aagtggtga atcccaccca aaagagccc     1260
aaatcttgtg acaaaactca cacatgccca ccgtgcccag cacctgaact cctgggggga    1320
ccgtcagtct tcctcttccc cccaaaaccc aaggacaccc tcatgatctc ccggacccct    1380
gaggtcacat gcgtggtggt ggacgtgagc acgaagacc ctgaggtcaa gttcaactgg    1440
tacgtggacg gcgtggaggt gcataatgcc aagacaaagc cgcgggagga gcagtacaac    1500
agcacgtacc gtgtggtcag cgtcctcacc gtcctgcacc aggactggct gaatggcaag    1560
gagtacaagt gcaaggtctc caacaaagcc ctcccagccc ccatcgagaa aaccatctcc    1620
aaagccaaag gcagccccg agaaccacag gtgtacaccc tgcccccatc ccgggatgag    1680
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacacg    1920
cagaagagcc tctccctgtc tccgggtaaa tga                                 1953
```

<210> SEQ ID NO 73
<211> LENGTH: 650
<212> TYPE: PRT
<213> ORGANISM: Artificial Sequence
<220> FEATURE:
<223> OTHER INFORMATION: AAT-Fc

<400> SEQUENCE: 73

Met Pro Ser Ser Val Ser Trp Gly Ile Leu Leu Leu Ala Gly Leu Cys

```
1               5                    10                   15
Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
                35                  40                  45

Lys Ile Thr Pro Asn Leu Ala Glu Phe Ala Phe Ser Leu Tyr Arg Gln
                50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
                100                 105                 110

Glu Ala Gln Ile His Glu Gly Phe Gln Glu Leu Leu Arg Thr Leu Asn
                115                 120                 125

Gln Pro Asp Ser Gln Leu Gln Leu Thr Thr Gly Asn Gly Leu Phe Leu
                130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
                195                 200                 205

Val Asn Tyr Ile Phe Phe Lys Gly Lys Trp Glu Arg Pro Phe Glu Val
                210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
                290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
                370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Glu Pro Lys Ser Cys Asp Lys Thr His Thr Cys Pro Pro Cys
                420                 425                 430
```

Pro Ala Pro Glu Leu Leu Gly Gly Pro Ser Val Phe Leu Phe Pro Pro
           435                 440                 445

Lys Pro Lys Asp Thr Leu Met Ile Ser Arg Thr Pro Glu Val Thr Cys
    450                 455                 460

Val Val Val Asp Val Ser His Glu Asp Pro Glu Val Lys Phe Asn Trp
465                 470                 475                 480

Tyr Val Asp Gly Val Glu Val His Asn Ala Lys Thr Lys Pro Arg Glu
                485                 490                 495

Glu Gln Tyr Asn Ser Thr Tyr Arg Val Val Ser Val Leu Thr Val Leu
            500                 505                 510

His Gln Asp Trp Leu Asn Gly Lys Glu Tyr Lys Cys Lys Val Ser Asn
        515                 520                 525

Lys Ala Leu Pro Ala Pro Ile Glu Lys Thr Ile Ser Lys Ala Lys Gly
    530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
                565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Lys Leu Thr Val Asp Lys Ser Arg Trp Gln Gln Gly Asn
    610                 615                 620

Val Phe Ser Cys Ser Val Met His Glu Ala Leu His Asn His Tyr Thr
625                 630                 635                 640

Gln Lys Ser Leu Ser Leu Ser Pro Gly Lys
                645                 650

<210> SEQ ID NO 74
<211> LENGTH: 1881
<212> TYPE: DNA
<213> ORGANISM: Artificial Sequence
<220> FEATURE:
<223> OTHER INFORMATION: AAT-Fc

<400> SEQUENCE: 74
gaggatcccc agggagatgc tgcccagaag acagatacat cccaccacga tcaggatcac     60
ccaaccttca acaagatcac ccccaacctg gctgagttcg ccttcagcct ataccgccag    120
ctggcacacc agtccaacag caccaatatc ttcttctccc cagtgagcat cgctacagcc    180
tttgcaatgc tctccctggg gaccaaggct gacactcacg atgaaatcct gggggcctg     240 aatttcaacc tcacggagat tccggaggct cagatccatg aaggcttcca ggaactcctc    300
cgtaccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca agaaacagat caacgattac    480
gtggagaagg gtactcaagg gaaaattgtg gatttggtca aggagcttga cagagacaca    540 gttttttgctc tggtgaatta catcttcttt aaaggcaaat gggagagacc ctttgaagtc    600
aaggacaccg aggaagagga cttccacgtg gaccaggtga ccaccgtgaa ggtgcctatg    660
atgaagcgtt taggcatgtt taacatccag cactgtaaga gctgtccag ctgggtgctg    720 ctgatgaaat acctgggcaa tgccaccgcc atcttcttcc tgcctgatga ggggaaacta    780

```
cagcacctgg aaaatgaact cacccacgat atcatcacca agttcctgga aaatgaagac    840
agaaggtctg ccagcttaca tttacccaaa ctgtccatta ctggaaccta tgatctgaag    900
agcgtcctgg gtcaactggg catcactaag gtcttcagca atggggctga cctctccggg    960
gtcacagagg aggcacccct gaagctctcc aaggccgtgc ataaggctgt gctgaccatc   1020
gacgagaaag ggactgaagc tgctggggcc atgttttag aggccatacc catgtctatc    1080
ccccccgagg tcaagttcaa caaacccttt gtcttcttaa tgattgaaca aaataccaag   1140
tctcccctct tcatgggaaa agtggtgaat cccacccaaa aagagcccaa atcttgtgac   1200
aaaactcaca catgcccacc gtgcccagca cctgaactcc tggggggacc gtcagtcttc   1260
ctcttccccc caaaacccaa ggacaccctc atgatctccc ggacccctga ggtcacatgc   1320
gtggtggtgg acgtgagcca cgaagaccct gaggtcaagt tcaactggta cgtggacggc   1380
gtggaggtgc ataatgccaa gacaaagccg cgggaggagc agtacaacag cacgtaccgt   1440
gtggtcagcg tcctcaccgt cctgcaccag gactggctga atggcaagga gtacaagtgc   1500
aaggtctcca acaaagccct cccagccccc atcgagaaaa ccatctccaa agccaaaggg   1560
cagccccgag aaccacaggt gtacaccctg cccccatccc gggatgagct gaccaagaac   1620
caggtcagcc tgacctgcct ggtcaaaggc ttctatccca gcgacatcgc cgtggagtgg   1680
gagagcaatg ggcagccgga gaacaactac aagaccacgc ctcccgtgct ggactccgac   1740
ggctccttct tcctctacag caagctcacc gtggacaaga gcaggtggca gcaggggaac   1800
gtcttctcat gctccgtgat gcatgaggct ctgcacaacc actacacgca gaagagcctc   1860
tccctgtctc cgggtaaatg a                                             1881

<210> SEQ ID NO 75
<211> LENGTH: 626
<212> TYPE: PRT
<213> ORGANISM: Artificial Sequence
<220> FEATURE:
<223> OTHER INFORMATION: AAT-Fc

<400> SEQUENCE: 75

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
```

```
            165                 170                 175
Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
            290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
            370                 375                 380

Met Gly Lys Val Val Asn Pro Thr Gln Lys Glu Pro Lys Ser Cys Asp
385                 390                 395                 400

Lys Thr His Thr Cys Pro Pro Cys Pro Ala Pro Glu Leu Leu Gly Gly
            405                 410                 415

Pro Ser Val Phe Leu Phe Pro Pro Lys Pro Lys Asp Thr Leu Met Ile
            420                 425                 430

Ser Arg Thr Pro Glu Val Thr Cys Val Val Val Asp Val Ser His Glu
            435                 440                 445

Asp Pro Glu Val Lys Phe Asn Trp Tyr Val Asp Gly Val Glu Val His
450                 455                 460

Asn Ala Lys Thr Lys Pro Arg Glu Glu Gln Tyr Asn Ser Thr Tyr Arg
465                 470                 475                 480

Val Val Ser Val Leu Thr Val Leu His Gln Asp Trp Leu Asn Gly Lys
            485                 490                 495

Glu Tyr Lys Cys Lys Val Ser Asn Lys Ala Leu Pro Ala Pro Ile Glu
            500                 505                 510

Lys Thr Ile Ser Lys Ala Lys Gly Gln Pro Arg Glu Pro Gln Val Tyr
            515                 520                 525

Thr Leu Pro Pro Ser Arg Asp Glu Leu Thr Lys Asn Gln Val Ser Leu
            530                 535                 540

Thr Cys Leu Val Lys Gly Phe Tyr Pro Ser Asp Ile Ala Val Glu Trp
545                 550                 555                 560

Glu Ser Asn Gly Gln Pro Glu Asn Asn Tyr Lys Thr Thr Pro Pro Val
            565                 570                 575

Leu Asp Ser Asp Gly Ser Phe Phe Leu Tyr Ser Lys Leu Thr Val Asp
            580                 585                 590
```

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
            610                 615                 620

Gly Lys
625

<210> SEQ ID NO 76
<211> LENGTH: 1257
<212> TYPE: DNA
<213> ORGANISM: Human AAT

<400> SEQUENCE: 76

```
atgccgtctt ctgtctcgtg gggcatcctc ctgctggcag gcctgtgctg cctggtccct    60
gtctccctgg ctgaggatcc ccagggagat gctgcccaga gacagatac atcccaccac   120
gatcaggatc acccaacctt caacaagatc accccaacc tggctgagtt cgccttcagc   180
ctataccgcc agctggcaca ccagtccaac agcaccaata tcttcttctc cccagtgagc   240
atcgctacag cctttgcaat gctctccctg ggaccaagg ctgacactca cgatgaaatc   300
ctggagggcc tgaatttcaa cctcacggag attccgagg ctcagatcca tgaaggcttc   360
caggaactcc tccgtaccct caaccagcca gacagccagc tccagctgac accggcaat   420
ggcctgttcc tcagcgaggg cctgaagcta gtggataagt ttttggagga tgttaaaaag   480
ttgtaccact cagaagcctt cactgtcaac ttcggggaca ccgaagaggc caagaaacag   540
atcaacgatt acgtggagaa gggtactcaa gggaaaattg tggatttggt caaggagctt   600
gacagagaca cagttttgc tctggtgaat tacatcttct ttaaaggcaa atgggagaga   660
ccctttgaag tcaaggacac cgaggaagag gacttccacg tggaccaggc gaccaccgtg   720
aaggtgccta tgatgaagcg tttaggcatg tttaacatcc agcactgtaa gaagctgtcc   780
agctgggtgc tgctgatgaa ataccctggg aatgccaccg ccatcttctt cctgcctgat   840
gaggggaaac tacagcacct ggaaaatgaa ctcacccacg atatcatcac caagttcctg   900
gaaaatgaag acagaaggtc tgccagctta catttaccca aactgtccat tactggaacc   960
tatgatctga gagcgtcct gggtcaactg gcatcacta aggtcttcag caatggggct  1020
gacctctccg ggtcacaga ggaggcaccc ctgaagctct ccaaggccgt gcataaggct  1080
gtgctgacca tcgacgagaa agggactgaa gctgctgggg ccatgttttt agaggccata  1140
cccatgtcta tcccccccga ggtcaagttc aacaaaccct tgtcttcttt aatgattgaa  1200
caaaatacca agtctcccct cttcatggga aagtggtga atcccaccca aaaatga     1257
```

<210> SEQ ID NO 77
<211> LENGTH: 418
<212> TYPE: PRT
<213> ORGANISM: Human AAT

<400> SEQUENCE: 77

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
            130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
            370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 78
<211> LENGTH: 1185
<212> TYPE: DNA
<213> ORGANISM: Human AAT

<400> SEQUENCE: 78
gaggatcccc agggagatgc tgcccagaag acagatacat cccaccacga tcaggatcac    60

```
ccaaccttca acaagatcac ccccaacctg gctgagttcg ccttcagcct ataccgccag    120
ctggcacacc agtccaacag caccaatatc ttcttctccc cagtgagcat cgctacagcc    180
tttgcaatgc tctccctggg gaccaaggct gacactcacg atgaaatcct ggagggcctg    240
aatttcaacc tcacggagat tccggaggct cagatccatg aaggcttcca ggaactcctc    300
cgtaccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca agaaacagat caacgattac    480
gtggagaagg gtactcaagg gaaaattgtg gatttggtca aggagcttga cagagacaca    540 gttttgctc tggtgaatta catcttcttt aaaggcaaat gggagagacc ctttgaagtc    600
aaggacaccg aggaagagga cttccacgtg gaccaggcga ccaccgtgaa ggtgcctatg    660
atgaagcgtt taggcatgtt taacatccag cactgtaaga agctgtccag ctgggtgctg    720
ctgatgaaat acctgggcaa tgccaccgcc atcttcttcc tgcctgatga ggggaaacta    780
cagcacctgg aaaatgaact cacccacgat atcatcacca gttcctgga aaatgaagac    840 agaaggtctg ccagcttaca tttacccaaa ctgtccatta ctggaaccta tgatctgaag    900
agcgtcctgg tcaactggg catcactaag gtcttcagca tggggctga cctctccggg    960 gtcacagagg aggcacccct gaagctctcc aaggccgtgc ataaggctgt gctgaccatc   1020
gacgagaaag ggactgaagc tgctggggcc atgtttttag aggccatacc catgtctatc   1080
ccccccgagg tcaagttcaa caaaccctt gtcttcttaa tgattgaaca aaataccaag   1140 tctccctct tcatgggaaa agtggtgaat cccacccaaa aatga                   1185

<210> SEQ ID NO 79
<211> LENGTH: 394
<212> TYPE: PRT
<213> ORGANISM: Human AAT

<400> SEQUENCE: 79

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175
```

Asp Arg Asp Thr Val Phe Ala Leu Val Asn Tyr Ile Phe Lys Gly
            180                 185                 190

Lys Trp Glu Arg Pro Phe Glu Val Lys Asp Thr Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 80
<211> LENGTH: 1959
<212> TYPE: DNA
<213> ORGANISM: Artificial Sequence
<220> FEATURE:
<223> OTHER INFORMATION: AAT-Fc

<400> SEQUENCE: 80
atgccgtctt ctgtctcgtg gggcatcctc ctgctggcag gcctgtgctg cctggtccct     60
gtctccctgg ctgaggatcc ccagggagat gctgcccaga gacagataca tcccaccac    120 gatcaggatc acccaacctt caacaagatc accccaacc tggctgagtt cgccttcagc    180
ctataccgcc agctggcaca ccagtccaac agcaccaata tcttcttctc cccagtgagc    240
atcgctacag cctttgcaat gctctccctg gggaccaagg ctgacactca cgatgaaatc    300
ctggagggcc tgaatttcaa cctcacggag attccggagg ctcagatcca tgaaggcttc    360
caggaactcc tccgtaccct caaccagcca gacagccagc tccagctgac caccggcaat    420
ggcctgttcc tcagcgaggg cctgaagcta gtggataagt tttggagga tgttaaaaag    480 ttgtaccact cagaagcctt cactgtcaac ttcggggaca ccgaagaggc caagaaacag    540
atcaacgatt acgtggagaa gggtactcaa gggaaaattg tggatttggt caaggagctt    600
gacagagaca cagttttgc tctggtgaat acatcttct ttaaaggcaa atgggagaga    660
ccctttgaag tcaaggacac cgaggaagag gacttccacg tggaccaggc gaccaccgtg    720
aaggtgccta tgatgaagcg tttaggcatg tttaacatcc agcactgtaa gaagctgtcc    780
agctgggtgc tgctgatgaa atacctgggc aatgccaccg ccatcttctt cctgcctgat    840

-continued

```
gaggggaaac tacagcacct ggaaaatgaa ctcacccacg atatcatcac caagttcctg    900
gaaaatgaag acagaaggtc tgccagctta catttaccca aactgtccat tactggaacc    960
tatgatctga agagcgtcct gggtcaactg gcatcacta aggtcttcag caatggggct    1020
gacctctccg gggtcacaga ggaggcaccc ctgaagctct ccaaggccgt gcataaggct    1080
gtgctgacca tcgacgagaa agggactgaa gctgctgggg ccatgttttt agaggccata    1140
cccatgtcta tccccccga ggtcaagttc aacaaaccct ttgtcttctt aatgattgaa    1200
caaaatacca agtctcccct cttcatggga aaagtggtga atcccaccca aaaaacgcgt    1260
gagcccaaat cttgtgacaa aactcacaca tgcccaccgt gcccagcacc tgaactcctg    1320
gggggaccgt cagtcttcct cttccccca aacccaagg acaccctcat gatctcccgg    1380
acccctgagg tcacatgcgt ggtggtggac gtgagccacg aagaccctga ggtcaagttc    1440
aactggtacg tggacggcgt ggaggtgcat aatgccaaga caaagccgcg ggaggagcag    1500
tacaacagca cgtaccgtgt ggtcagcgtc ctcaccgtcc tgcaccagga ctggctgaat    1560
ggcaaggagt acaagtgcaa ggtctccaac aaagccctcc cagcccccat cgagaaaacc    1620
atctccaaag ccaaagggca gccccgagaa ccacaggtgt acaccctgcc cccatcccgg    1680
gatgagctga ccaagaacca ggtcagcctg acctgcctgg tcaaaggctt ctatcccagc    1740
gacatcgccg tggagtggga gagcaatggg cagccggaga acaactacaa gaccacgcct    1800
cccgtgctgg actccgacgg ctccttcttc ctctacagca agctcaccgt ggacaagagc    1860
aggtggcagc aggggaacgt cttctcatgc tccgtgatgc atgaggctct gcacaaccac    1920
tacacgcaga agagcctctc cctgtctccg ggtaaatga                           1959
```

<210> SEQ ID NO 81
<211> LENGTH: 652
<212> TYPE: PRT
<213> ORGANISM: Artificial Sequence
<220> FEATURE:
<223> OTHER INFORMATION: AAT-Fc

<400> SEQUENCE: 81

```
Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160
```

```
Leu Tyr His Ser Glu Ala Phe Thr Val Asn Phe Gly Asp Thr Glu
            165                 170                 175

Ala Lys Lys Gln Ile Asn Asp Tyr Val Glu Lys Gly Thr Gln Gly Lys
        180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Asp Phe His Val Asp Gln Ala Thr Thr Val
225                 230                 235                 240

Lys Val Pro Met Met Lys Arg Leu Gly Met Phe Asn Ile Gln His Cys
            245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
            290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
            325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
            405                 410                 415

Gln Lys Thr Arg Glu Pro Lys Ser Cys Asp Lys Thr His Thr Cys Pro
            420                 425                 430

Pro Cys Pro Ala Pro Glu Leu Leu Gly Gly Pro Ser Val Phe Leu Phe
            435                 440                 445

Pro Pro Lys Pro Lys Asp Thr Leu Met Ile Ser Arg Thr Pro Glu Val
            450                 455                 460

Thr Cys Val Val Val Asp Val Ser His Glu Asp Pro Glu Val Lys Phe
465                 470                 475                 480

Asn Trp Tyr Val Asp Gly Val Glu Val His Asn Ala Lys Thr Lys Pro
            485                 490                 495

Arg Glu Glu Gln Tyr Asn Ser Thr Tyr Arg Val Val Ser Val Leu Thr
            500                 505                 510

Val Leu His Gln Asp Trp Leu Asn Gly Lys Glu Tyr Lys Cys Lys Val
            515                 520                 525

Ser Asn Lys Ala Leu Pro Ala Pro Ile Glu Lys Thr Ile Ser Lys Ala
            530                 535                 540

Lys Gly Gln Pro Arg Glu Pro Gln Val Tyr Thr Leu Pro Pro Ser Arg
545                 550                 555                 560

Asp Glu Leu Thr Lys Asn Gln Val Ser Leu Thr Cys Leu Val Lys Gly
                    565                 570                 575

Phe Tyr Pro Ser Asp Ile Ala Val Glu Trp Glu Ser Asn Gly Gln Pro
```

Glu Asn Asn Tyr Lys Thr Thr Pro Pro Val Leu Asp Ser Asp Gly Ser
            580             585                 590
                595                 600                 605

Phe Phe Leu Tyr Ser Lys Leu Thr Val Asp Lys Ser Arg Trp Gln Gln
        610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650

<210> SEQ ID NO 82
<211> LENGTH: 1953
<212> TYPE: DNA
<213> ORGANISM: Artificial Sequence
<220> FEATURE:
<223> OTHER INFORMATION: AAT-Fc

<400> SEQUENCE: 82

| | |
|---|---|
| atgccgtctt ctgtctcgtg gggcatcctc ctgctggcag cctgtgctg cctggtccct | 60 |
| gtctccctgg ctgaggatcc ccagggagat gctgcccaga agacagatac atcccaccac | 120 |
| gatcaggatc acccaacctt caacaagatc accccaaccc tggctgagtt cgccttcagc | 180 |
| ctataccgcc agctggcaca ccagtccaac agcaccaata tcttcttctc cccagtgagc | 240 |
| atcgctacag cctttgcaat gctctccctg gggaccaagg ctgacactca cgatgaaatc | 300 |
| ctggagggcc tgaatttcaa cctcacggag attccggagg ctcagatcca tgaaggcttc | 360 |
| caggaactcc tccgtaccct caaccagcca gacagccagc tccagctgac caccggcaat | 420 |
| ggcctgttcc tcagcgaggg cctgaagcta gtggataagt ttttggagga tgttaaaaag | 480 |
| ttgtaccact cagaagcctt cactgtcaac ttcggggaca ccgaagaggc caagaaacag | 540 |
| atcaacgatt acgtggagaa gggtactcaa gggaaaattg tggatttggt caaggagctt | 600 |
| gacagagaca cagttttttgc tctggtgaat tacatcttct ttaaaggcaa atgggagaga | 660 |
| ccctttgaag tcaaggacac cgaggaagag gacttccacg tggaccaggc gaccaccgtg | 720 |
| aaggtgccta tgatgaagcg tttaggcatg tttaacatcc agcactgtaa gaagctgtcc | 780 |
| agctgggtgc tgctgatgaa atacctgggc aatgccaccg ccatcttctt cctgcctgat | 840 |
| gaggggaaac tacagcacct ggaaaatgaa ctcacccacg atatcatcac caagttcctg | 900 |
| gaaaatgaag acagaaggtc tgccagctta catttaccca aactgtccat tactggaacc | 960 |
| tatgatctga gagcgtcctg ggtcaactg gcatcacta aggtcttcag caatggggct | 1020 |
| gacctctccg ggtcacaga ggaggcaccc ctgaagctct ccaaggccgt gcataaggct | 1080 |
| gtgctgacca tcgacgagaa agggactgaa gctgctgggg ccatgttttt agaggccata | 1140 |
| cccatgtcta tccccccga ggtcaagttc aacaaaccct tgtcttcttt aatgattgaa | 1200 |
| caaaatacca gtctccccct cttcatggga aagtggtga atcccaccca aaaagagccc | 1260 |
| aaatcttgtg acaaaactca cacatgccca ccgtgcccag cacctgaact cctggggggga | 1320 |
| ccgtcagtct tcctcttccc cccaaaaccc aaggacaccc tcatgatctc ccggaccct | 1380 |
| gaggtcacat gcgtggtggt ggacgtgagc cacgaagacc ctgaggtcaa gttcaactgg | 1440 |
| tacgtggacg gcgtggaggt gcataatgcc aagacaaagc cgcgggagga gcagtacaac | 1500 |
| agcacgtacc gtgtggtcag cgtcctcacc gtcctgcacc aggactggct gaatggcaag | 1560 |
| gagtacaagt gcaaggtctc caacaaagcc ctcccagccc ccatcgagaa aaccatctcc | 1620 |
| aaagccaaag ggcagccccg agaaccacag gtgtacaccc tgcccccatc ccgggatgag | 1680 |

```
ctgaccaaga accaggtcag cctgacctgc ctggtcaaag gcttctatcc cagcgacatc    1740
gccgtggagt gggagagcaa tgggcagccg gagaacaact acaagaccac gcctcccgtg    1800
ctggactccg acggctcctt cttcctctac agcaagctca ccgtggacaa gagcaggtgg    1860
cagcagggga acgtcttctc atgctccgtg atgcatgagg ctctgcacaa ccactacacg    1920
cagaagagcc tctccctgtc tccgggtaaa tga                                1953

<210> SEQ ID NO 83
<211> LENGTH: 650
<212> TYPE: PRT
<213> ORGANISM: Artificial Sequence
<220> FEATURE:
<223> OTHER INFORMATION: AAT-Fc

<400> SEQUENCE: 83
```

Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Ala Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr

Tyr Asp Leu Lys Ser Val Leu Gly Gln Leu Gly Ile Thr Lys Val Phe
305                 310                 315                 320

Ser Asn Gly Ala Asp Leu Ser Gly Val Thr Glu Ala Pro Leu Lys
            325                 330                 335

Leu Ser Lys Ala Val His Lys Ala Val Leu Thr Ile Asp Glu Lys Gly
        340                 345                 350

Thr Glu Ala Ala Gly Ala Met Phe Leu Glu Ala Ile Pro Met Ser Ile
    355                 360                 365

Pro Pro Glu Val Lys Phe Asn Lys Pro Phe Val Phe Leu Met Ile Glu
370     375                 380

Gln Asn Thr Lys Ser Pro Leu Phe Met Gly Lys Val Val Asn Pro Thr
            385                 390                 395                 400

Gln Lys Glu Pro Lys Ser Cys Asp Lys Thr His Thr Cys Pro Pro Cys
        405                 410                 415

Pro Ala Pro Glu Leu Leu Gly Gly Pro Ser Val Phe Leu Phe Pro Pro
    420                 425                 430

Lys Pro Lys Asp Thr Leu Met Ile Ser Arg Thr Pro Glu Val Thr Cys
435                 440                 445

Val Val Val Asp Val Ser His Glu Asp Pro Glu Val Lys Phe Asn Trp
465                 450                 455                 460

Tyr Val Asp Gly Val Glu Val His Asn Ala Lys Thr Lys Pro Arg Glu
            485                 490                 495

Glu Gln Tyr Asn Ser Thr Tyr Arg Val Val Ser Val Leu Thr Val Leu
        500                 505                 510

His Gln Asp Trp Leu Asn Gly Lys Glu Tyr Lys Cys Lys Val Ser Asn
    515                 520                 525

Lys Ala Leu Pro Ala Pro Ile Glu Lys Thr Ile Ser Lys Ala Lys Gly
530                 535                 540

Gln Pro Arg Glu Pro Gln Val Tyr Thr Leu Pro Pro Ser Arg Asp Glu
545                 550                 555                 560

Leu Thr Lys Asn Gln Val Ser Leu Thr Cys Leu Val Lys Gly Phe Tyr
            565                 570                 575

Pro Ser Asp Ile Ala Val Glu Trp Glu Ser Asn Gly Gln Pro Glu Asn
        580                 585                 590

Asn Tyr Lys Thr Thr Pro Pro Val Leu Asp Ser Asp Gly Ser Phe Phe
    595                 600                 605

Leu Tyr Ser Lys Leu Thr Val Asp Lys Ser Arg Trp Gln Gln Gly Asn
610                 615                 620

Val Phe Ser Cys Ser Val Met His Glu Ala Leu His Asn His Tyr Thr
625                 630                 635                 640

Gln Lys Ser Leu Ser Leu Ser Pro Gly Lys
            645                 650

<210> SEQ ID NO 84
<211> LENGTH: 1881
<212> TYPE: DNA
<213> ORGANISM: Artificial Sequence
<220> FEATURE:
<223> OTHER INFORMATION: AAT-Fc

<400> SEQUENCE: 84
gaggatcccc agggagatgc tgcccagaag acagatacat cccaccacga tcaggatcac      60
ccaaccttca acaagatcac ccccaacctg gctgagttcg ccttcagcct ataccgccag     120

-continued

```
ctggcacacc agtccaacag caccaatatc ttcttctccc cagtgagcat cgctacagcc    180
tttgcaatgc tctccctggg gaccaaggct gacactcacg atgaaatcct ggagggcctg    240
aatttcaacc tcacggagat tccggaggct cagatccatg aaggcttcca ggaactcctc    300
cgtaccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca gaaacagat caacgattac    480
gtggagaagg gtactcaagg gaaaattgtg gatttggtca aggagcttga cagagacaca    540
gttttgctc tggtgaatta catcttcttt aaaggcaaat gggagagacc ctttgaagtc    600
aaggacaccg aggaagagga cttccacgtg gaccaggcga ccaccgtgaa ggtgcctatg    660
atgaagcgtt taggcatgtt taacatccag cactgtaaga gctgtccagc tgggtgctg    720
ctgatgaaat acctgggcaa tgccaccgcc atcttcttcc tgcctgatga ggggaaacta    780
cagcacctgg aaaatgaact cacccacgat atcatcacca gttcctgga aaatgaagac    840
agaaggtctg ccagcttaca tttacccaaa ctgtccatta ctggaaccta tgatctgaag    900
agcgtcctgg gtcaactggg catcactaag gtcttcagca atgggctga cctctccggg    960
gtcacagagg aggcaccct gaagctctcc aaggccgtgc ataaggctgt gctgaccatc   1020
gacgagaaag ggactgaagc tgctggggcc atgtttttag aggccatacc catgtctatc   1080
cccccgagg tcaagttcaa caaacccttt gtcttcttaa tgattgaaca aaataccaag   1140
tctcccctct tcatgggaaa agtggtgaat cccaccccaa agagcccaa atcttgtgac   1200
aaaactcaca catgcccacc gtgcccagca cctgaactcc tgggggacc gtcagtcttc   1260
ctcttccccc caaaacccaa ggacaccctc atgatctccc ggaccctga ggtcacatgc   1320
gtggtggtgg acgtgagcca cgaagaccct gaggtcaagt tcaactggta cgtggacggc   1380
gtggaggtgc ataatgccaa gacaaagccg cgggaggagc agtacaacag cacgtaccgt   1440
gtggtcagcg tcctcaccgt cctgcaccag gactggctga atggcaagga gtacaagtgc   1500
aaggtctcca acaaagccct cccagccccc atcgagaaaa ccatctccaa agccaaaggg   1560
cagccccgag aaccacaggt gtacaccctg cccccatccc gggatgagct gaccaagaac   1620
caggtcagcc tgacctgcct ggtcaaaggc ttctatccca gcgacatcgc cgtggagtgg   1680
gagagcaatg ggcagccgga gaacaactac aagaccacgc ctcccgtgct ggactccgac   1740
ggctccttct tcctctacag caagctcacc gtggacaaga gcaggtggca gcaggggaac   1800
gtcttctcat gctccgtgat gcatgaggct ctgcacaacc actacacgca gaagagcctc   1860
tccctgtctc cgggtaaatg a                                              1881
```

<210> SEQ ID NO 85
<211> LENGTH: 626
<212> TYPE: PRT
<213> ORGANISM: Artificial Sequence
<220> FEATURE:
<223> OTHER INFORMATION: AAT-Fc

<400> SEQUENCE: 85

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45
```

```
Asn Ile Phe Phe Ser Pro Val Ser Ile Ala Thr Ala Phe Ala Met Leu
 50                  55                  60
Ser Leu Gly Thr Lys Ala Asp Thr His Asp Glu Ile Leu Glu Gly Leu
 65                  70                  75                  80
Asn Phe Asn Leu Thr Glu Ile Pro Glu Ala Gln Ile His Glu Gly Phe
                 85                  90                  95
Gln Glu Leu Leu Arg Thr Leu Asn Gln Pro Asp Ser Gln Leu Gln Leu
                100                 105                 110
Thr Thr Gly Asn Gly Leu Phe Leu Ser Glu Gly Leu Lys Leu Val Asp
            115                 120                 125
Lys Phe Leu Glu Asp Val Lys Lys Leu Tyr His Ser Glu Ala Phe Thr
130                 135                 140
Val Asn Phe Gly Asp Thr Glu Glu Ala Lys Lys Gln Ile Asn Asp Tyr
145                 150                 155                 160
Val Glu Lys Gly Thr Gln Gly Lys Ile Val Asp Leu Val Lys Glu Leu
                165                 170                 175
Asp Arg Asp Thr Val Phe Ala Leu Val Asn Tyr Ile Phe Phe Lys Gly
            180                 185                 190
Lys Trp Glu Arg Pro Phe Glu Val Lys Asp Thr Glu Glu Glu Asp Phe
        195                 200                 205
His Val Asp Gln Ala Thr Thr Val Lys Val Pro Met Met Lys Arg Leu
210                 215                 220
Gly Met Phe Asn Ile Gln His Cys Lys Lys Leu Ser Ser Trp Val Leu
225                 230                 235                 240
Leu Met Lys Tyr Leu Gly Asn Ala Thr Ala Ile Phe Phe Leu Pro Asp
                245                 250                 255
Glu Gly Lys Leu Gln His Leu Glu Asn Glu Leu Thr His Asp Ile Ile
            260                 265                 270
Thr Lys Phe Leu Glu Asn Glu Asp Arg Arg Ser Ala Ser Leu His Leu
        275                 280                 285
Pro Lys Leu Ser Ile Thr Gly Thr Tyr Asp Leu Lys Ser Val Leu Gly
290                 295                 300
Gln Leu Gly Ile Thr Lys Val Phe Ser Asn Gly Ala Asp Leu Ser Gly
305                 310                 315                 320
Val Thr Glu Glu Ala Pro Leu Lys Leu Ser Lys Ala Val His Lys Ala
                325                 330                 335
Val Leu Thr Ile Asp Glu Lys Gly Thr Glu Ala Ala Gly Ala Met Phe
            340                 345                 350
Leu Glu Ala Ile Pro Met Ser Ile Pro Pro Glu Val Lys Phe Asn Lys
        355                 360                 365
Pro Phe Val Phe Leu Met Ile Glu Gln Asn Thr Lys Ser Pro Leu Phe
370                 375                 380
Met Gly Lys Val Val Asn Pro Thr Gln Lys Glu Pro Lys Ser Cys Asp
385                 390                 395                 400
Lys Thr His Thr Cys Pro Pro Cys Pro Ala Pro Glu Leu Leu Gly Gly
                405                 410                 415
Pro Ser Val Phe Leu Phe Pro Pro Lys Pro Lys Asp Thr Leu Met Ile
            420                 425                 430
Ser Arg Thr Pro Glu Val Thr Cys Val Val Val Asp Val Ser His Glu
        435                 440                 445
Asp Pro Glu Val Lys Phe Asn Trp Tyr Val Asp Gly Val Glu Val His
450                 455                 460
Asn Ala Lys Thr Lys Pro Arg Glu Glu Gln Tyr Asn Ser Thr Tyr Arg
```

Val Val Ser Val Leu Thr Val Leu His Gln Asp Trp Leu Asn Gly Lys
            465                 470                 475                 480

Glu Tyr Lys Cys Lys Val Ser Asn Lys Ala Leu Pro Ala Pro Ile Glu
            485                 490                 495

Lys Thr Ile Ser Lys Ala Lys Gly Gln Pro Arg Glu Pro Gln Val Tyr
            500                 505                 510

Thr Leu Pro Pro Ser Arg Asp Glu Leu Thr Lys Asn Gln Val Ser Leu
            515                 520                 525

Thr Cys Leu Val Lys Gly Phe Tyr Pro Ser Asp Ile Ala Val Glu Trp
530                 535                 540

545                 550                 555                 560

Glu Ser Asn Gly Gln Pro Glu Asn Asn Tyr Lys Thr Thr Pro Pro Val
            565                 570                 575

Leu Asp Ser Asp Gly Ser Phe Phe Leu Tyr Ser Lys Leu Thr Val Asp
            580                 585                 590

Lys Ser Arg Trp Gln Gln Gly Asn Val Phe Ser Cys Ser Val Met His
            595                 600                 605

Glu Ala Leu His Asn His Tyr Thr Gln Lys Ser Leu Ser Leu Ser Pro
            610                 615                 620

Gly Lys
625

<210> SEQ ID NO 86
<211> LENGTH: 1886
<212> TYPE: DNA
<213> ORGANISM: Artificial Sequence
<220> FEATURE:
<223> OTHER INFORMATION: AAT-Fc

<400> SEQUENCE: 86

```
gaggatcccc agggagatgc tgcccagaag acagatacat cccaccacga tcaggatcac     60
ccaaccttca acaagatcac ccccaacctg gctgagttcg ccttcagcct ataccgccag    120
ctggcacacc agtccaacag caccaatatc ttcttctccc cagtgagcat cgctacagcc    180
tttgcaatgc tctccctggg gaccaaggct gacactcacg atgaaatcct ggagggcctg    240
aatttcaacc tcacggagat tccggaggct cagatccatg aaggcttcca ggaactcctc    300
cgtaccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca gaaacagat caacgattac    480
gtggagaagg gtactcaagg gaaaattgtg gatttggtca aggagcttga cagagacaca    540
gttttttgctc tggtgaatta catcttcttt aaaggcaaat gggagagacc ctttgaagtc    600
aaggacaccg aggaagagga cttccacgtg gaccaggtga ccaccgtgaa ggtgcctatg    660
atgaagcgtt taggcatgtt taacatccag cactgtaaga gctgtccag ctgggtgctg    720
ctgatgaaat acctgggcaa tgccaccgcc atcttcttcc tgcctgatga ggggaaacta    780
cagcacctgg aaaatgaact cacccacgat atcatcacca gttcctgga aatgaagac    840
agaaggtctg ccagcttaca tttacccaaa ctgtccatta ctggaaccta tgatctgaag    900
agcgtcctgg gtcaactggg catcactaag gtcttcagca tggggctga cctctccggg    960
gtcacagagg aggcaccccct gaagctctcc aaggccgtgc ataaggctgt gctgaccatc   1020
gacgagaaag gactgaagc tgctggggcc atgtttttag aggccatacc catgtctatc   1080
ccccccgagg tcaagttcaa caaaccctttt gtcttcttaa tgattgaaca aaataccaag   1140
```

```
tctcccctct tcatgggaaa agtggtgaat cccacccaaa aaacgcgtga gcccaaatct    1200
tgtgacaaaa ctcacacatg cccaccgtgc ccagcacctg aactcctggg gggaccgtca    1260
gtcttcctct tccccccaaa acccaaggac accctcatga tctcccggac ccctgaggtc    1320
acatgcgtgg tggtggacgt gagccacgaa gaccctgagg tcaagttcaa ctggtacgtg    1380
gacggcgtgg aggtgcataa tgccaagaca aagccgcggg aggagcagac aacagcacgt    1440
accgtgtggt cagcgtcctc accgtcctgc accaggactg gctgaatggc aaggagtaca    1500
agtgcaaggt ctccaacaaa gccctcccag cccccatcga gaaaaccatc tccaaagcca    1560
aagggcagcc ccgagaacca caggtgtaca ccctgccccc atcccgggat gagctgacca    1620
agaaccaggt cagcctgacc tgcctggtca aaggcttcta tcccagcgac atcgccgtgg    1680
agtgggagag caatgggcag ccggagaaca actacaagac cacgcctccc gtgctggact    1740
ccgacggctc cttcttcctc tacagcaagc tcaccgtgga caagagcagg tggcagcagg    1800
ggaacgtctt ctcatgctcc gtgatgcatg aggctctgca caaccactac acgcagaaga    1860
gcctctccct gtctccgggt aaatga                                        1886
```

<210> SEQ ID NO 87
<211> LENGTH: 628
<212> TYPE: PRT
<213> ORGANISM: Artificial Sequence
<220> FEATURE:
<223> OTHER INFORMATION: AAT-Fc

<400> SEQUENCE: 87

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220
```

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
            245                 250                 255

Glu Gly Lys Leu Gln His Leu Glu Asn Glu Leu Thr His Asp Ile Ile
        260                 265                 270

Thr Lys Phe Leu Glu Asn Glu Asp Arg Arg Ser Ala Ser Leu His Leu
    275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
            325                 330                 335

Val Leu Thr Ile Asp Glu Lys Gly Thr Glu Ala Ala Gly Ala Met Phe
        340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Thr Arg Glu Pro Lys Ser
385                 390                 395                 400

Cys Asp Lys Thr His Thr Cys Pro Pro Cys Pro Ala Pro Glu Leu Leu
            405                 410                 415

Gly Gly Pro Ser Val Phe Leu Phe Pro Pro Lys Pro Lys Asp Thr Leu
        420                 425                 430

Met Ile Ser Arg Thr Pro Glu Val Thr Cys Val Val Val Asp Val Ser
            435                 440                 445

His Glu Asp Pro Glu Val Lys Phe Asn Trp Tyr Val Asp Gly Val Glu
        450                 455                 460

Val His Asn Ala Lys Thr Lys Pro Arg Glu Glu Gln Tyr Asn Ser Thr
465                 470                 475                 480

Tyr Arg Val Val Ser Val Leu Thr Val Leu His Gln Asp Trp Leu Asn
            485                 490                 495

Gly Lys Glu Tyr Lys Cys Lys Val Ser Asn Lys Ala Leu Pro Ala Pro
        500                 505                 510

Ile Glu Lys Thr Ile Ser Lys Ala Lys Gly Gln Pro Arg Glu Pro Gln
        515                 520                 525

Val Tyr Thr Leu Pro Pro Ser Arg Asp Glu Leu Thr Lys Asn Gln Val
    530                 535                 540

Ser Leu Thr Cys Leu Val Lys Gly Phe Tyr Pro Ser Asp Ile Ala Val
545                 550                 555                 560

Glu Trp Glu Ser Asn Gly Gln Pro Glu Asn Asn Tyr Lys Thr Thr Pro
            565                 570                 575

Pro Val Leu Asp Ser Asp Gly Ser Phe Phe Leu Tyr Ser Lys Leu Thr
        580                 585                 590

Val Asp Lys Ser Arg Trp Gln Gln Gly Asn Val Phe Ser Cys Ser Val
            595                 600                 605

Met His Glu Ala Leu His Asn His Tyr Thr Gln Lys Ser Leu Ser Leu
        610                 615                 620

Ser Pro Gly Lys
625

<210> SEQ ID NO 88
<211> LENGTH: 1886
<212> TYPE: DNA
<213> ORGANISM: Artificial Sequence
<220> FEATURE:
<223> OTHER INFORMATION: AAT-Fc

<400> SEQUENCE: 88

```
gaggatcccc agggagatgc tgcccagaag acagatacat cccaccacga tcaggatcac      60
ccaaccttca acaagatcac ccccaacctg gctgagttcg ccttcagcct ataccgccag     120
ctggcacacc agtccaacag caccaatatc ttcttctccc cagtgagcat cgctacagcc     180
tttgcaatgc tctccctggg gaccaaggct gacactcacg atgaaatcct ggagggcctg     240
aatttcaacc tcacggagat tccggaggct cagatccatg aaggcttcca ggaactcctc     300
cgtaccctca accagccaga cagccagctc agctgaccca ccggcaatgg cctgttcctc     360
agcgagggcc tgaagctagt ggataagttt ttggaggatg ttaaaaagtt gtaccactca     420
gaagccttca ctgtcaactt cggggacacc gaagaggcca gaaacagat caacgattac      480
gtggagaagg gtactcaagg gaaaattgtg gatttggtca aggagcttga cagagacaca     540
gttttgctc tggtgaatta catcttcttt aaaggcaaat gggagagacc ctttgaagtc      600
aaggacaccg aggaagagga cttccacgtg gaccaggcga ccaccgtgaa ggtgcctatg     660
atgaagcgtt taggcatgtt taacatccag cactgtaaga agctgtccag ctgggtgctg     720
ctgatgaaat acctgggcaa tgccaccgcc atcttcttcc tgcctgatga ggggaaacta     780
cagcacctgg aaaatgaact cacccacgat atcatcacca agttcctgga aaatgaagac     840
agaaggtctg ccagcttaca tttacccaaa ctgtccatta ctggaaccta tgatctgaag     900
agcgtcctgg tcaactggg catcactaag gtcttcagca atggggctga cctctccggg     960
gtcacagagg aggcacccct gaagctctcc aaggccgtgc ataaggctgt gctgaccatc    1020
gacgagaaag ggactgaagc tgctggggcc atgttttag aggccatacc catgtctatc     1080
cccccgagg tcaagttcaa caaacccttt gtcttcttaa tgattgaaca aataccaag     1140
tctcccctct tcatgggaaa agtggtgaat cccacccaaa aaacgcgtga gcccaaatct    1200
tgtgacaaaa ctcacacatg cccaccgtgc ccagcacctg aactcctggg gggaccgtca    1260
gtcttcctct tccccccaaa acccaaggac accctcatga tctcccggac ccctgaggtc    1320
acatgcgtgg tggtggacgt gagccacgaa gaccctgagg tcaagttcaa ctggtacgtg    1380
gacggcgtgg aggtgcataa tgccaagaca aagccgcggg aggagcagac aacagcacgt    1440
accgtgtggt cagcgtcctc accgtcctgc caggactgg ctgaatggc aaggagtaca     1500
agtgcaaggt ctccaacaaa gccctcccag cccccatcga gaaaaccatc tccaaagcca    1560
aagggcagcc ccgagaacca caggtgtaca ccctgccccc atcccgggat gagctgacca    1620
agaaccaggt cagcctgacc tgcctggtca aaggcttcta tcccagcgac atcgccgtgg    1680
agtgggagag caatgggcag ccggagaaca actacaagac cacgcctccc gtgctggact    1740
ccgacggctc cttcttcctc tacagcaagc tcaccgtgga caagagcagg tggcagcagg    1800
ggaacgtctt ctcatgctcc gtgatgcatg aggctctgca caaccactac acgcagaaga    1860
gcctctccct gtctccgggt aaatga                                         1886
```

<210> SEQ ID NO 89
<211> LENGTH: 628
<212> TYPE: PRT
<213> ORGANISM: Artificial Sequence
<220> FEATURE:

<223> OTHER INFORMATION: AAT-Fc

<400> SEQUENCE: 89

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Ala Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys Thr Arg Glu Pro Lys Ser
385                 390                 395                 400
```

-continued

```
Cys Asp Lys Thr His Thr Cys Pro Pro Cys Pro Ala Pro Glu Leu Leu
                405             410             415

Gly Gly Pro Ser Val Phe Leu Phe Pro Pro Lys Pro Lys Asp Thr Leu
            420             425             430

Met Ile Ser Arg Thr Pro Glu Val Thr Cys Val Val Val Asp Val Ser
        435             440             445

His Glu Asp Pro Glu Val Lys Phe Asn Trp Tyr Val Asp Gly Val Glu
    450             455             460

Val His Asn Ala Lys Thr Lys Pro Arg Glu Glu Gln Tyr Asn Ser Thr
465             470             475             480

Tyr Arg Val Val Ser Val Leu Thr Val Leu His Gln Asp Trp Leu Asn
            485             490             495

Gly Lys Glu Tyr Lys Cys Lys Val Ser Asn Lys Ala Leu Pro Ala Pro
                500             505             510

Ile Glu Lys Thr Ile Ser Lys Ala Lys Gly Gln Pro Arg Glu Pro Gln
            515             520             525

Val Tyr Thr Leu Pro Pro Ser Arg Asp Glu Leu Thr Lys Asn Gln Val
        530             535             540

Ser Leu Thr Cys Leu Val Lys Gly Phe Tyr Pro Ser Asp Ile Ala Val
545             550             555             560

Glu Trp Glu Ser Asn Gly Gln Pro Glu Asn Asn Tyr Lys Thr Thr Pro
                565             570             575

Pro Val Leu Asp Ser Asp Gly Ser Phe Phe Leu Tyr Ser Lys Leu Thr
            580             585             590

Val Asp Lys Ser Arg Trp Gln Gln Gly Asn Val Phe Ser Cys Ser Val
        595             600             605

Met His Glu Ala Leu His Asn His Tyr Thr Gln Lys Ser Leu Ser Leu
    610             615             620

Ser Pro Gly Lys
625
```